United States Patent
Liu et al.

(10) Patent No.: US 12,252,746 B2
(45) Date of Patent: Mar. 18, 2025

(54) ANTI-CD46 ANTIBODIES AND METHODS OF USE

(71) Applicant: The Regents of the University of California, Oakland, CA (US)

(72) Inventors: Bin Liu, San Francisco, CA (US); Daniel W. Sherbenou, Denver, CO (US); Blake T. Aftab, Thousand Oaks, CA (US); Yang Su, South San Francisco, CA (US); Christopher R. Behrens, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/815,514

(22) Filed: Jul. 27, 2022

(65) Prior Publication Data

US 2023/0383005 A1 Nov. 30, 2023

Related U.S. Application Data

(62) Division of application No. 16/348,135, filed as application No. PCT/US2017/061124 on Nov. 10, 2017, now Pat. No. 11,434,301.

(60) Provisional application No. 62/421,113, filed on Nov. 11, 2016.

(51) Int. Cl.
| | |
|---|---|
| *C12Q 1/6886* | (2018.01) |
| *A61K 39/00* | (2006.01) |
| *A61K 47/68* | (2017.01) |
| *A61P 35/00* | (2006.01) |
| *C07K 16/00* | (2006.01) |
| *C07K 16/28* | (2006.01) |
| *C07K 16/30* | (2006.01) |
| *G01N 33/574* | (2006.01) |

(52) U.S. Cl.
CPC ...... *C12Q 1/6886* (2013.01); *A61K 47/68031* (2023.08); *A61K 47/6809* (2017.08); *A61K 47/6813* (2017.08); *A61K 47/6849* (2017.08); *A61P 35/00* (2018.01); *C07K 16/00* (2013.01); *C07K 16/2818* (2013.01); *C07K 16/2827* (2013.01); *C07K 16/2896* (2013.01); *C07K 16/3069* (2013.01); *G01N 33/57492* (2013.01); *A61K 2039/505* (2013.01); *A61K 2039/55* (2013.01); *C07K 2317/24* (2013.01); *C07K 2317/77* (2013.01); *C12Q 2600/106* (2013.01); *C12Q 2600/112* (2013.01); *G01N 2800/52* (2013.01)

(58) Field of Classification Search
CPC ............ C07K 16/2896; C07K 16/2818; A61K 47/6803; A61K 47/6809
See application file for complete search history.

(56) References Cited

U.S. PATENT DOCUMENTS

| | | | |
|---|---|---|---|
| 7,378,504 | B2 | 5/2008 | Graziano et al. |
| 8,843,320 | B2 | 9/2014 | Shaughnessy et al. |
| 11,434,301 | B2 | 9/2022 | Liu et al. |
| 2012/0015906 | A1 | 1/2012 | Shaughnessy, Jr. et al. |
| 2014/0271685 | A1 | 9/2014 | Liu |
| 2019/0276553 | A1 | 9/2019 | Liu et al. |

FOREIGN PATENT DOCUMENTS

| | | |
|---|---|---|
| WO | WO-2012031273 A2 | 3/2012 |
| WO | WO-2016040683 A1 | 3/2016 |
| WO | WO-2018089807 A2 | 5/2018 |

OTHER PUBLICATIONS

Hanamura et al, Frequent gain of chromosome band 1q21 in plasma-cell dyscrasias detected by fluorescence in situ hybridization Blood, 2006, 108:1724-1732, Publication Date: May 16, 2006 (Year: 2006).*
Almagro & Fransson (2008) "Humanization of antibodies" Frontiers in Bioscience 13: 1619-33.
Biran et al. (2014) "Patients with newly diagnosed multiple myeloma and chromosome 1 amplification have poor outcomes despite the use of novel triplet regimens" American Journal of Hematology, 89(6): 616-620.
Carrasco et al. (2006) "High-resolution genomic profiles define distinct clinico-pathogenetic subgroups of multiple myeloma patients" Cancer Cell, 9: 313-325.
Chen et al. (2016) "The amplification of I q21 is an adverse prognostic factor in patients with multiple myeloma in a Chinese population" Onco Targets and Therapy, 9: 295-302.
European Extended Search Report dated May 26, 2020 issued in EP 17870330.2.
European Office Action dated May 6, 2021 issued in EP 17870330.2.
Hanamura (2021) "Gain/Amplification of Chromosome Arm 1q21 in Multiple Myeloma" Cancers, 13(2): 256 (16 pages).
Hanamura et al. (2006) "Frequent gain of chromosome band 1q21 in plasma-cell dyscrasias detected by fluorescence in situ hybridization" Blood 108(5): 1724-1732.

(Continued)

*Primary Examiner* — Peter J Reddig
*Assistant Examiner* — Cheng Lu
(74) *Attorney, Agent, or Firm* — Mintz, Levin, Cohn, Ferris, Glovsky and Popeo, P.C.

(57) ABSTRACT

Disclosed herein are methods of treating a subject having a cancer characterized by a modification at biomarker 1q21, which comprises administering to the subject a therapeutically effective amount of an anti-CD46 antibody.

10 Claims, 31 Drawing Sheets
(10 of 31 Drawing Sheet(s) Filed in Color)
Specification includes a Sequence Listing.

(56) References Cited

OTHER PUBLICATIONS

Nemec et al. (2010) "Gain of Iq21 Is an Unfavorable Genetic Prognostic Factor for Multiple Myeloma Patients Treated with High-Dose Chemotherapy" Biol Blood Marrow Transplant, 16: 548-554.

PCT International Preliminary Report on Patentability dated May 14, 2019 issued in PCT/US2017/061124.

PCT International Search Report and Written Opinion dated May 11, 2018 issued in PCT/US2017/061124.

Sawyer et al. (2009) "Evidence for a Novel Mechanism for Gene Amplification in Multiple Myeloma: 1q12 Pericentromeric Heterochromatin Mediates Breakage-Fusion-Bridge Cycles of a 1q12~23 Amplicon" Br. J. Haematology, 147(4): 484-494 [HHS Public Access—Author Manuscripts—PMC3738438—17 pages].

Schmidt et al. (2021) "Chromosome 1q21 abnormalities in multiple myeloma" Blood Cancer J. , 11: 83 (11 pages).

Sherbenou et al. (2016) "Antibody-drug conjugate targeting CD46 eliminates multiple myeloma cells" J Clin Invest., 126(12): 4640-4653, doi.org/10.1172/JCI85856.

Sherbenou et al. (2016) "CD46 Is Amplified in High-Risk Myeloma with Gain of Chromosome 1q and Selectively Targeted By a Novel Anti-CD46 Antibody-Drug Conjugate" ASH 2016 Annual Meeting Abstract 384 (Oral Presentation), 128(22): 384 [4 pages], Downloaded from Internet: http://myelomabeacon.org/resources/mtgs/ash2016/abs/384/ Downloaded on May 16, 2018.

US Final Rejection dated Oct. 25, 2021, in U.S. Appl. No. 16/348,135.

U.S. Notice of Allowance dated Apr. 25, 2022 in U.S. Appl. No. 16/348,135.

US Office Action dated Apr. 13, 2021 issued in U.S. Appl. No. 16/348,135.

US Office Action [Restriction Requirement] dated Feb. 10, 2021 issued in U.S. Appl. No. 16/348,135.

\* cited by examiner

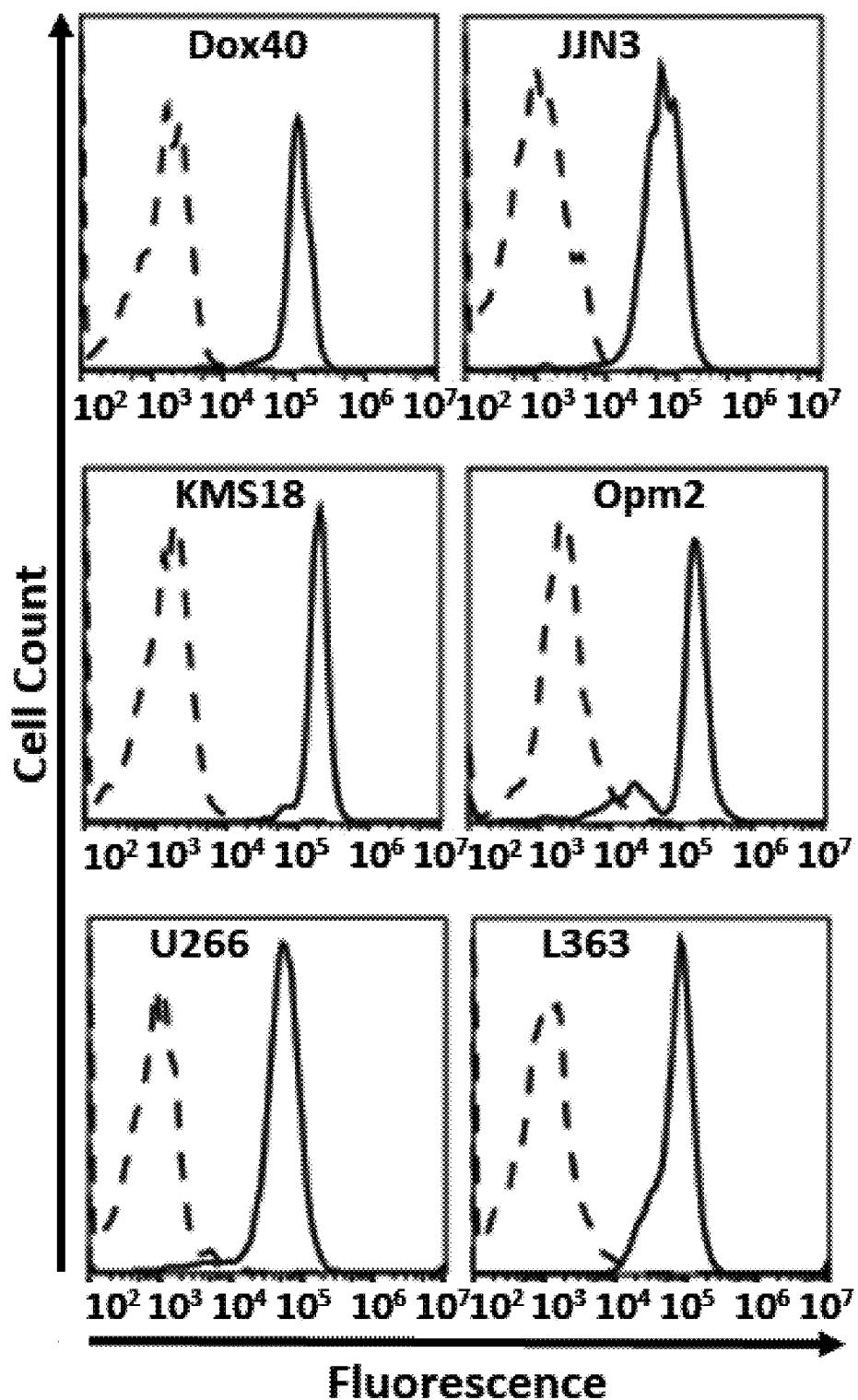
*Fig. 2, cont'd.*

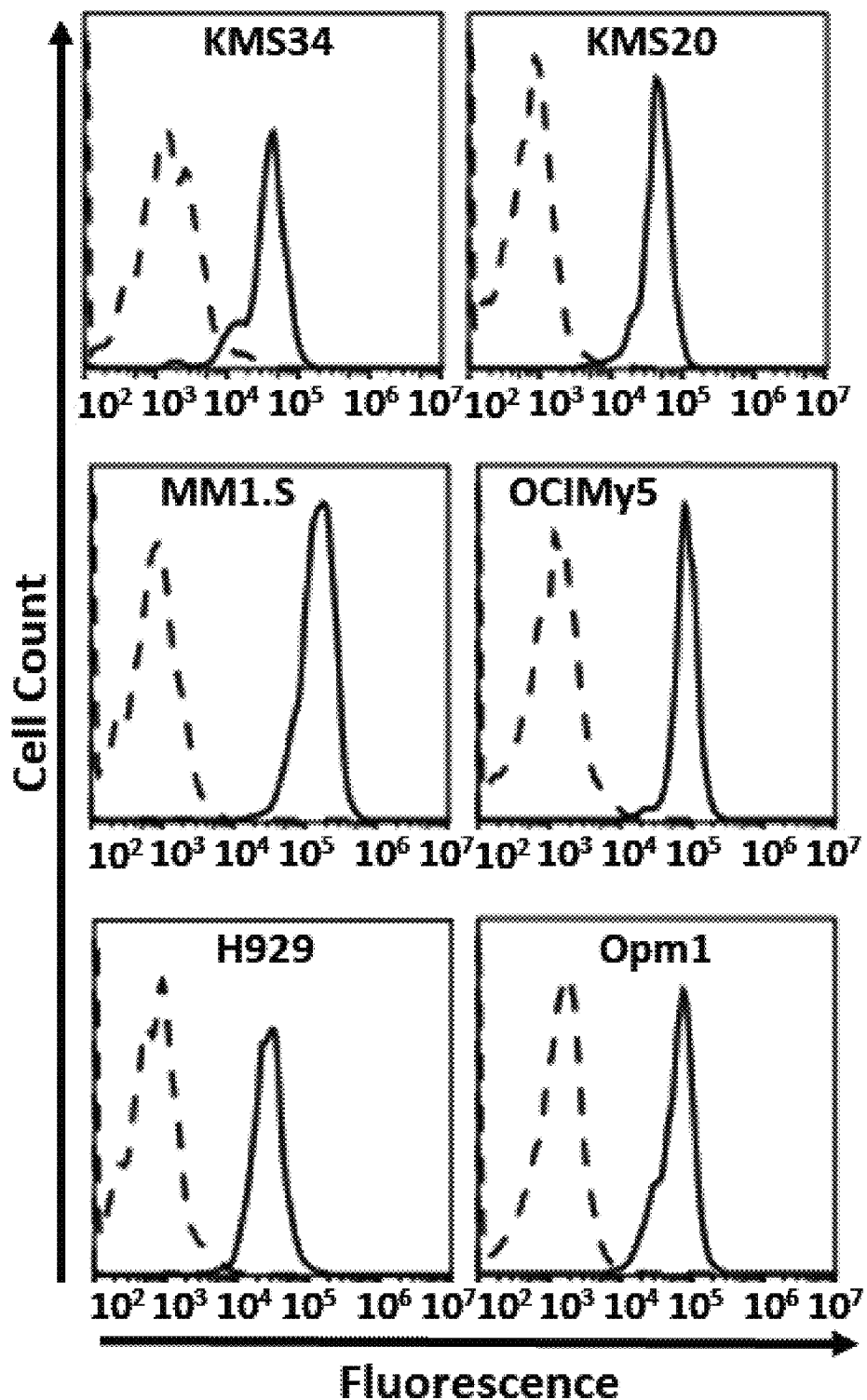
Fig. 2, cont'd.

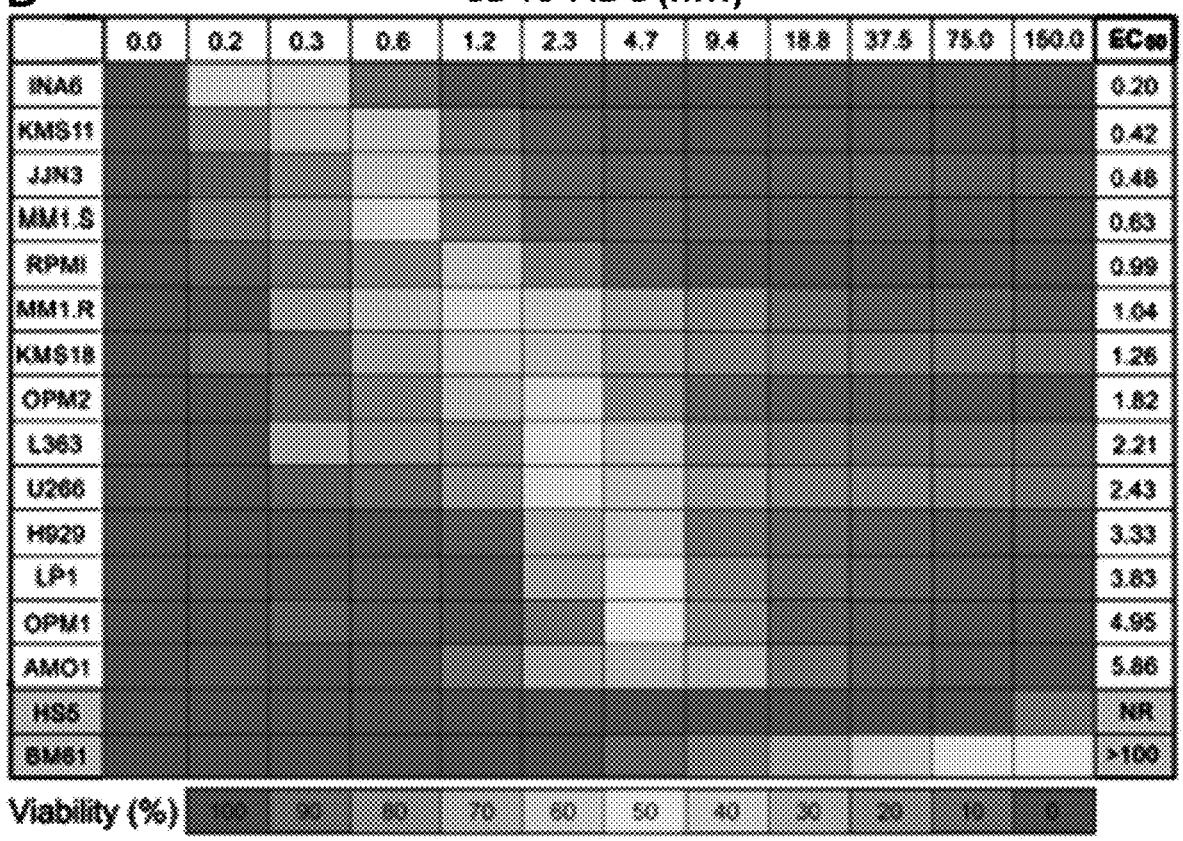
*Fig. 6, cont'd.*

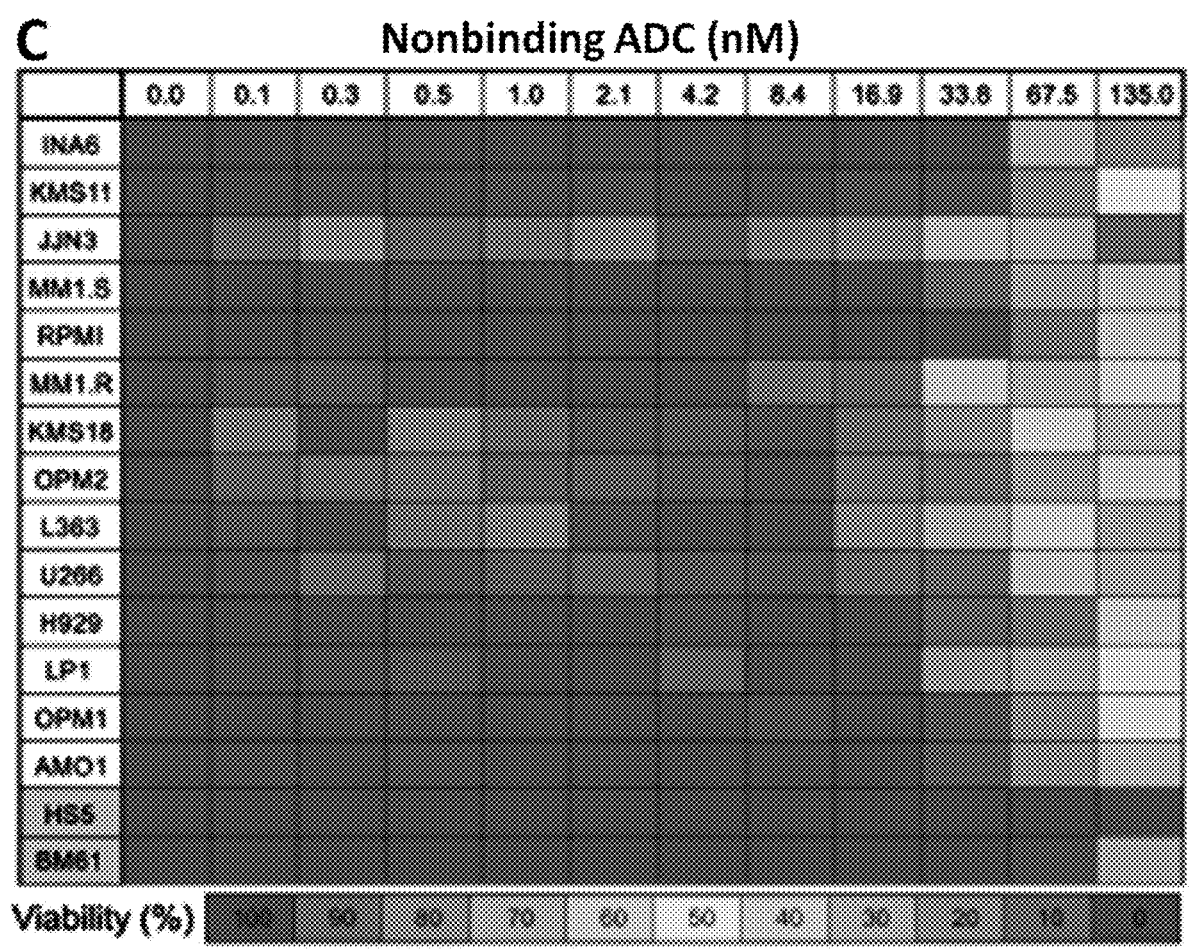
*Fig. 6, cont'd.*

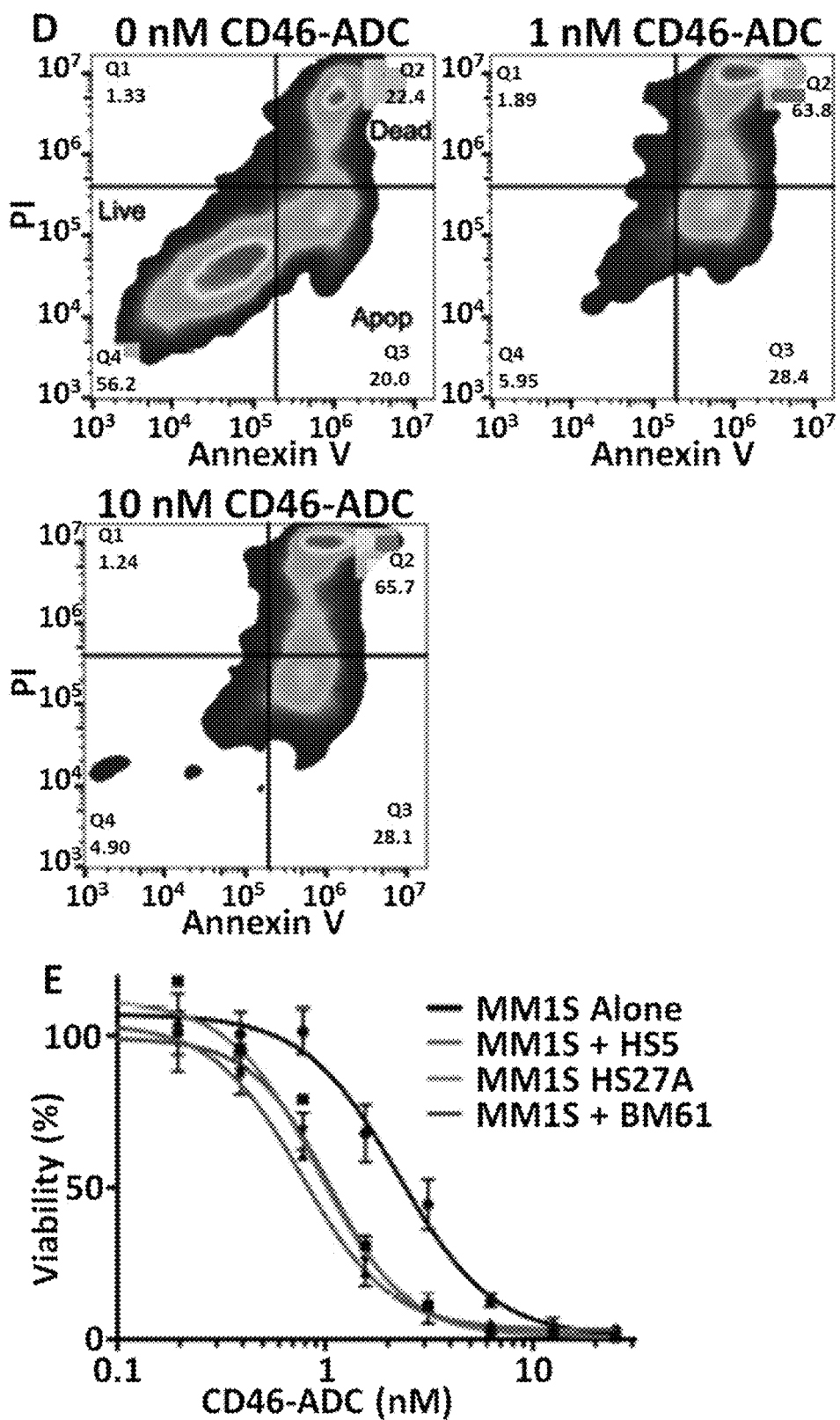
*Fig. 6, cont'd.*

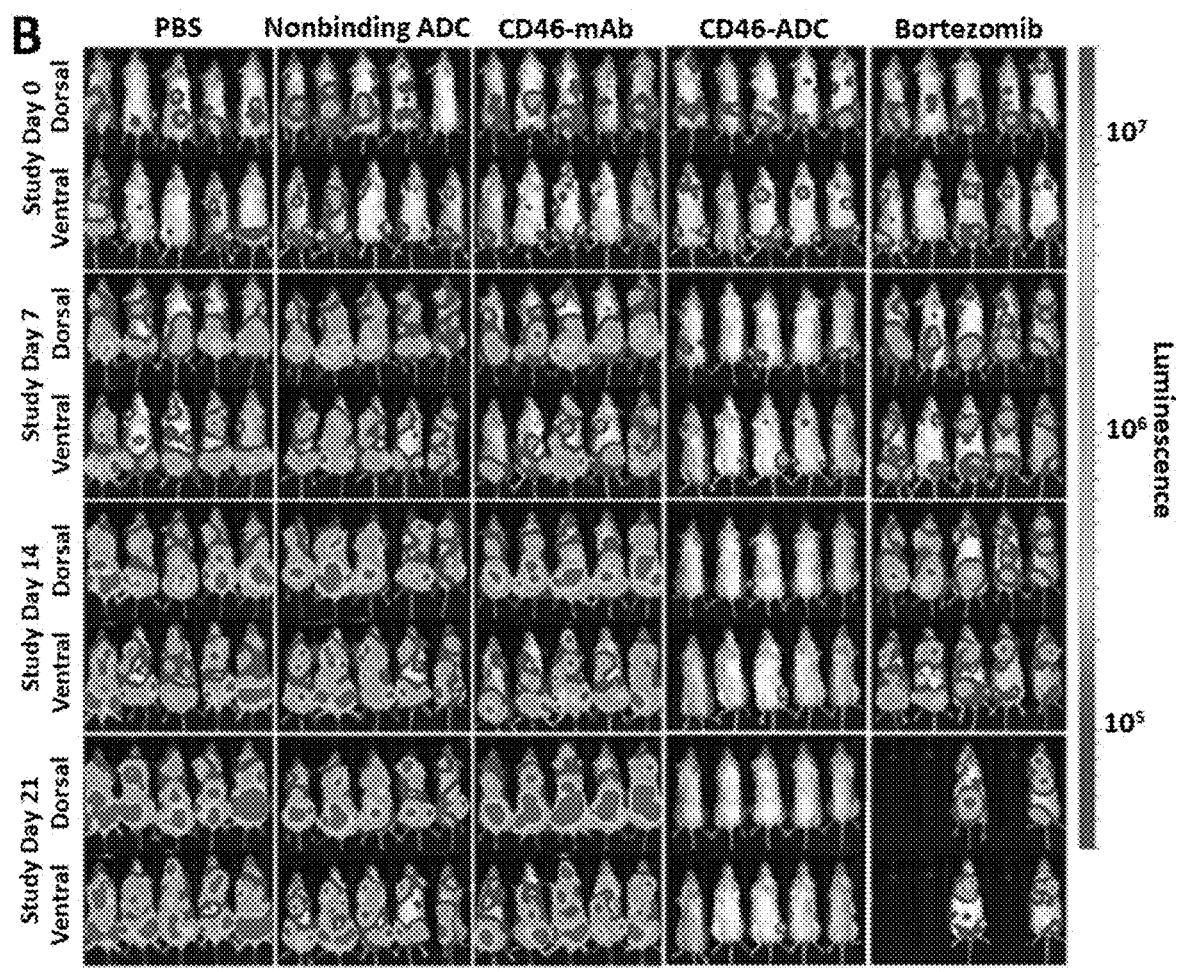
*Fig. 11, cont'd.*

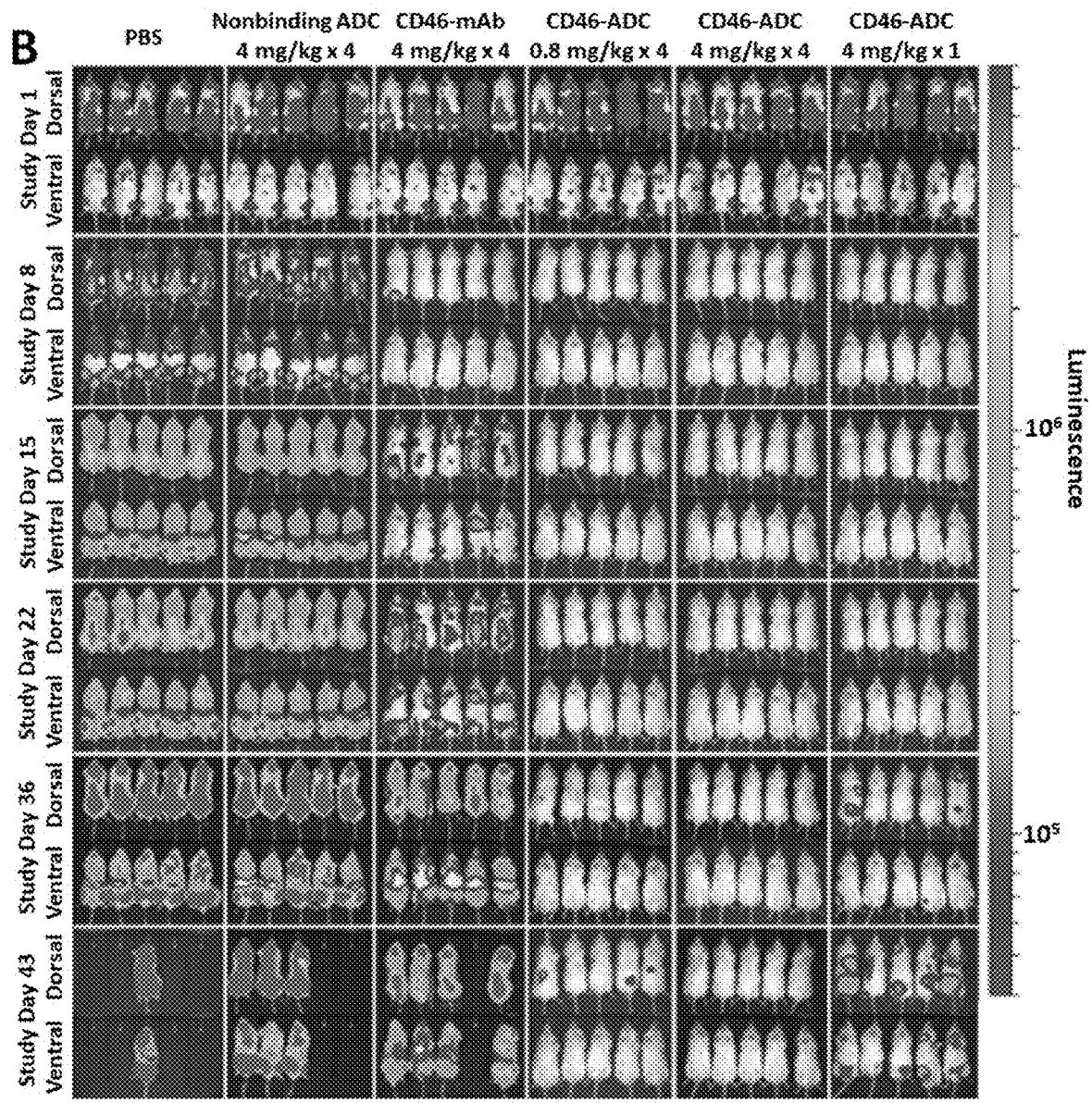
*Fig. 12, cont'd.*

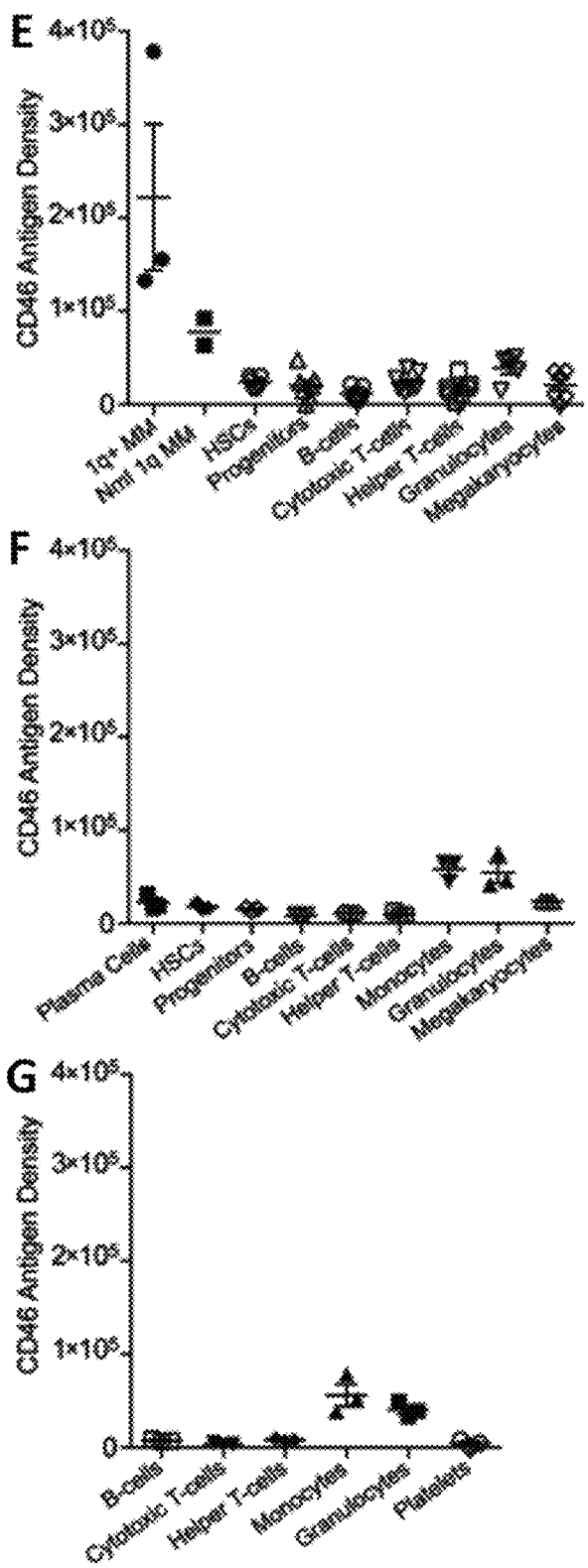
*Fig. 17, cont'd.*

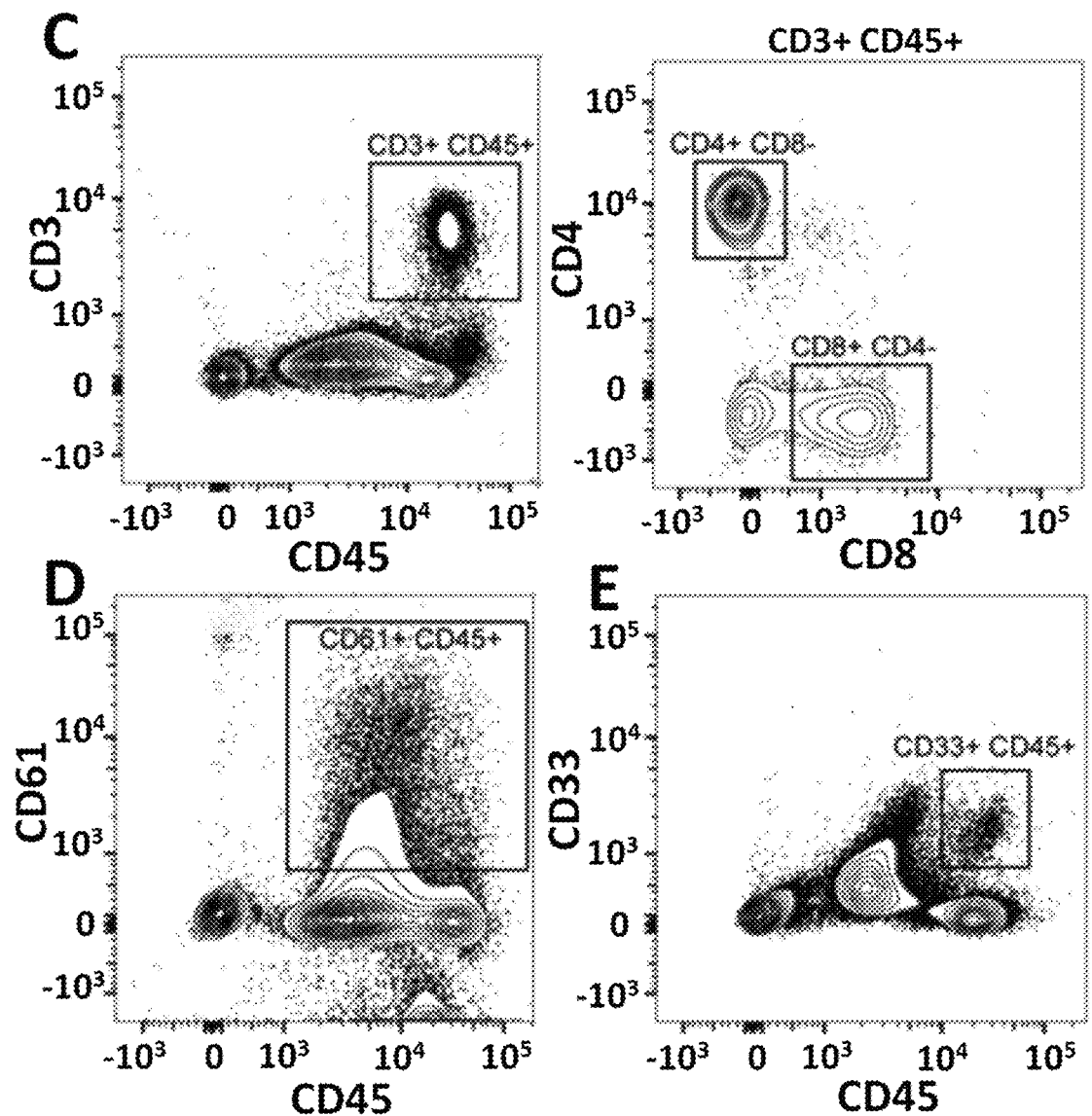
Fig 18, cont'd.

SEQUENCE LISTING

```
Sequence total quantity: 75
SEQ ID NO: 1              moltype = AA  length = 116
FEATURE                   Location/Qualifiers
REGION                    1..116
                          note = Synthetic antibody VH domain
source                    1..116
                          mol_type = protein
                          organism = synthetic construct
SEQUENCE: 1
QVQLVQSGGG VVQPGRSLRL ACAASGLTVN NYAMHWVRQA PGKGLEWVAV ISYDGNNKYY   60
ADSVKGRFTI SRDNSKNTLY LQMNSLRAED TAVYYCAKGG GYFDLWGRGT LVTVSS      116

SEQ ID NO: 2              moltype = AA  length = 109
FEATURE                   Location/Qualifiers
REGION                    1..109
                          note = Synthetic antibody VL domain
source                    1..109
                          mol_type = protein
                          organism = synthetic construct
SEQUENCE: 2
QSVLTQPPSV SGAPGQRVTI SCTGSSSNIG AGYDVHWYQQ LPGTAPKLLI YGNNNRPSGV   60
PDRFSGSKSG TSASLAITGL QAEDEADYYC SSYTSGTWLF GGGTKLTVL              109

SEQ ID NO: 3              moltype = AA  length = 8
FEATURE                   Location/Qualifiers
REGION                    1..8
                          note = Synthetic antibody VH CDR1 domain
source                    1..8
                          mol_type = protein
                          organism = synthetic construct
SEQUENCE: 3
GLTVNNYA                                                           8

SEQ ID NO: 4              moltype = AA  length = 8
FEATURE                   Location/Qualifiers
REGION                    1..8
                          note = Synthetic antibody VH CDR2 domain
source                    1..8
                          mol_type = protein
                          organism = synthetic construct
SEQUENCE: 4
ISYDGNNK                                                           8

SEQ ID NO: 5              moltype = AA  length = 9
FEATURE                   Location/Qualifiers
REGION                    1..9
                          note = Synthetic antibody VH CDR3 domain
source                    1..9
                          mol_type = protein
                          organism = synthetic construct
SEQUENCE: 5
AKGGGYFDL                                                          9

SEQ ID NO: 6              moltype = AA  length = 9
FEATURE                   Location/Qualifiers
```

```
REGION                  1..9
                        note = Synthetic antibody VL CDR1 domain
source                  1..9
                        mol_type = protein
                        organism = synthetic construct
SEQUENCE: 6
SSNIGAGYD                                                                      9

SEQ ID NO: 7            moltype =    length =
SEQUENCE: 7
000

SEQ ID NO: 8            moltype = AA   length = 9
FEATURE                 Location/Qualifiers
REGION                  1..9
                        note = Synthetic antibody VL CDR3 domain
source                  1..9
                        mol_type = protein
                        organism = synthetic construct
SEQUENCE: 8
SSYTSGTWL                                                                      9

SEQ ID NO: 9            moltype = AA   length = 120
FEATURE                 Location/Qualifiers
REGION                  1..120
                        note = Synthetic antibody VH domain
source                  1..120
                        mol_type = protein
                        organism = synthetic construct
SEQUENCE: 9
QVQLVESGGG VVQPGRSLRL SCAASGFTFS TYGMHWVRQA PGKGLEWLSF ISYDGDEKYY              60
ADSVKGRFTI SRDNSKNTLY LQMNSLRAED TAVYWCAKAS GYGMGILDYW GQGTLVTVSS             120

SEQ ID NO: 10           moltype = AA   length = 109
FEATURE                 Location/Qualifiers
REGION                  1..109
                        note = Synthetic antibody VL domain
source                  1..109
                        mol_type = protein
                        organism = synthetic construct
SEQUENCE: 10
SSELTQDPAV SVALGQTVRI TCQGDSLRSY YVSWFQQKPG QAPVFVMYGQ NNRPSGISER              60
FSGSSSGNTA SLIITGAQAE DEADYYCHSR DSSGTHLRVF GGGTKLTVL                         109

SEQ ID NO: 11           moltype = AA   length = 8
FEATURE                 Location/Qualifiers
REGION                  1..8
                        note = Synthetic antibody VH CDR1 domain
source                  1..8
                        mol_type = protein
                        organism = synthetic construct
SEQUENCE: 11
GFTFSTYG                                                                       8

SEQ ID NO: 12           moltype = AA   length = 9
FEATURE                 Location/Qualifiers
REGION                  1..9
                        note = Synthetic antibody VH CDR2 domain
source                  1..9
                        mol_type = protein
                        organism = synthetic construct
SEQUENCE: 12
FISYDGDEK                                                                      9

SEQ ID NO: 13           moltype = AA   length = 13
FEATURE                 Location/Qualifiers
REGION                  1..13
                        note = Synthetic antibody VH CDR3 domain
source                  1..13
                        mol_type = protein
                        organism = synthetic construct
SEQUENCE: 13
AKASGYGMGI LDY                                                                13

SEQ ID NO: 14           moltype = AA   length = 6
FEATURE                 Location/Qualifiers
REGION                  1..6
                        note = Synthetic antibody VL CDR1 domain
source                  1..6
```

```
                        mol_type = protein
                        organism = synthetic construct
SEQUENCE: 14
SLRSYY                                                                      6

SEQ ID NO: 15           moltype =    length =
SEQUENCE: 15
000

SEQ ID NO: 16           moltype = AA   length = 12
FEATURE                 Location/Qualifiers
REGION                  1..12
                        note = Synthetic antibody VL CDR3 domain
source                  1..12
                        mol_type = protein
                        organism = synthetic construct
SEQUENCE: 16
HSRDSSGTHL RV                                                              12

SEQ ID NO: 17           moltype = AA   length = 116
FEATURE                 Location/Qualifiers
REGION                  1..116
                        note = Synthetic antibody VH domain
source                  1..116
                        mol_type = protein
                        organism = synthetic construct
SEQUENCE: 17
QVQLVQSGGG VVQPGRSLRL ACAASGFTVN NYAMHWVRQA PGKGLEWVAV ISYDGNNKYY          60
ADSVKGRFTI SRDNSKNTLY LQMNSLRAED TAVYYCAKGG GYFDLWGRGT LVTVSS             116

SEQ ID NO: 18           moltype = AA   length = 109
FEATURE                 Location/Qualifiers
REGION                  1..109
                        note = Synthetic antibody VL domain
source                  1..109
                        mol_type = protein
                        organism = synthetic construct
SEQUENCE: 18
QSVLTQPPSV SGAPGQRVTI SCTGSSSNIG AGYDVHWYQQ LPGTAPKLLI YGDNNRPSGV          60
PDRFSGSKSG TSASLAITGL QAEDEADYYC SSYTSGTWLF GGGTKLTVL                    109

SEQ ID NO: 19           moltype = AA   length = 8
FEATURE                 Location/Qualifiers
REGION                  1..8
                        note = Synthetic antibody VH CDR1 domain
source                  1..8
                        mol_type = protein
                        organism = synthetic construct
SEQUENCE: 19
GFTVNNYA                                                                    8

SEQ ID NO: 20           moltype = AA   length = 8
FEATURE                 Location/Qualifiers
REGION                  1..8
                        note = Synthetic antibody VH CDR2 domain
source                  1..8
                        mol_type = protein
                        organism = synthetic construct
SEQUENCE: 20
ISYDGNNK                                                                    8

SEQ ID NO: 21           moltype = AA   length = 9
FEATURE                 Location/Qualifiers
REGION                  1..9
                        note = Synthetic antibody VH CDR3 domain
source                  1..9
                        mol_type = protein
                        organism = synthetic construct
SEQUENCE: 21
AKGGGYFDL                                                                   9

SEQ ID NO: 22           moltype = AA   length = 9
FEATURE                 Location/Qualifiers
REGION                  1..9
                        note = Synthetic antibody VL CDR1 domain
source                  1..9
                        mol_type = protein
                        organism = synthetic construct
SEQUENCE: 22
```

```
SSNIGAGYD                                                                      9

SEQ ID NO: 23           moltype =    length =
SEQUENCE: 23
000

SEQ ID NO: 24           moltype = AA   length = 9
FEATURE                 Location/Qualifiers
REGION                  1..9
                        note = Synthetic antibody VL CDR3 domain
source                  1..9
                        mol_type = protein
                        organism = synthetic construct
SEQUENCE: 24
SSYTSGTWL                                                                      9

SEQ ID NO: 25           moltype = AA   length = 116
FEATURE                 Location/Qualifiers
REGION                  1..116
                        note = Synthetic antibody VH domain
source                  1..116
                        mol_type = protein
                        organism = synthetic construct
SEQUENCE: 25
QVQLQQSGGG VVQPGRSLRL SCAASGFTFS SYAMHWVRQA PGKGLEWVAF IRSDGSKKYY              60
ADSVKGRFTI SRDNSKNTLY LQMNSLRAED TAVYYCARHG NYFDSWGQGT LVTVSS                 116

SEQ ID NO: 26           moltype = AA   length = 107
FEATURE                 Location/Qualifiers
REGION                  1..107
                        note = Synthetic antibody VL domain
source                  1..107
                        mol_type = protein
                        organism = synthetic construct
SEQUENCE: 26
DIQMTQSPSF LSASVGDRVT ITCRASQGIS SYLAWYQQKP GKAPKLLIYA ASTLQSGVPS              60
SFSGSGSGTE FTLTISSLQP EDFATYYCQQ LASYPLTFGG GTKVDIK                           107

SEQ ID NO: 27           moltype = AA   length = 8
FEATURE                 Location/Qualifiers
REGION                  1..8
                        note = Synthetic antibody VH CDR1 domain
source                  1..8
                        mol_type = protein
                        organism = synthetic construct
SEQUENCE: 27
GFTFSSYA                                                                       8

SEQ ID NO: 28           moltype = AA   length = 8
FEATURE                 Location/Qualifiers
REGION                  1..8
                        note = Synthetic antibody VH CDR2 domain
source                  1..8
                        mol_type = protein
                        organism = synthetic construct
SEQUENCE: 28
IRSDGSKK                                                                       8

SEQ ID NO: 29           moltype = AA   length = 9
FEATURE                 Location/Qualifiers
REGION                  1..9
                        note = Synthetic antibody VH CDR3 domain
source                  1..9
                        mol_type = protein
                        organism = synthetic construct
SEQUENCE: 29
ARHGNYFDS                                                                      9

SEQ ID NO: 30           moltype = AA   length = 6
FEATURE                 Location/Qualifiers
REGION                  1..6
                        note = Synthetic antibody VL CDR1 domain
source                  1..6
                        mol_type = protein
                        organism = synthetic construct
SEQUENCE: 30
QGISSY                                                                         6

SEQ ID NO: 31           moltype =    length =
```

```
SEQUENCE: 31
000

SEQ ID NO: 32            moltype = AA  length = 9
FEATURE                  Location/Qualifiers
REGION                   1..9
                         note = Synthetic antibody VL CDR3 domain
source                   1..9
                         mol_type = protein
                         organism = synthetic construct
SEQUENCE: 32
QQLASYPLT                                                                 9

SEQ ID NO: 33            moltype = AA  length = 116
FEATURE                  Location/Qualifiers
REGION                   1..116
                         note = Synthetic antibody VH domain
source                   1..116
                         mol_type = protein
                         organism = synthetic construct
SEQUENCE: 33
QVQLVQSGGG VVQPGRSLRL ACAASGFTVN NYAMHWVRQA PGKGLEWVAV ISYDGNNKYY         60
ADSVKGRFTI SRDNSKNTLY LQMNSLRAED TAVYYCAKGG GYFDLWGRGT LVTVSS            116

SEQ ID NO: 34            moltype = AA  length = 109
FEATURE                  Location/Qualifiers
REGION                   1..109
                         note = Synthetic antibody VL domain
source                   1..109
                         mol_type = protein
                         organism = synthetic construct
SEQUENCE: 34
QSVLTQPPSV SGAPGQRVTI SCTGSSSNIG AGYDVHWYQQ LPGTAPKLLI YGNNNRPSGV         60
PDRFSGSKSG TSASLAITGL QAEDEADYYC SSYTSGTWLF GGGTKLTVL                   109

SEQ ID NO: 35            moltype = AA  length = 121
FEATURE                  Location/Qualifiers
REGION                   1..121
                         note = Synthetic antibody VH domain
source                   1..121
                         mol_type = protein
                         organism = synthetic construct
SEQUENCE: 35
EVQLVESGGG LVQPGGSLRL SCAASGFTFS DYYMSWIRQA PGKGLEWVSY ISSSGSTIYY         60
ADSVKGRFTI SRDNSKNTLY LQMNSLRAED TAVYYCARDY GRIAAAGRRY WGQGTLVTVS       120
S                                                                       121

SEQ ID NO: 36            moltype = AA  length = 110
FEATURE                  Location/Qualifiers
REGION                   1..110
                         note = Synthetic antibody VL domain
source                   1..110
                         mol_type = protein
                         organism = synthetic construct
SEQUENCE: 36
QSALTQPPSA SATPGQRVTI SCSGRTSNIG SNHVYWYQQL PGTAPKLLIY RNNQRPSGVP         60
DRFSGSKSGT SASLAISGLR SEDEADYYCA TWDDSLSGEV FGGGTKLTVL                  110

SEQ ID NO: 37            moltype = AA  length = 121
FEATURE                  Location/Qualifiers
REGION                   1..121
                         note = Synthetic antibody VH domain
source                   1..121
                         mol_type = protein
                         organism = synthetic construct
SEQUENCE: 37
QVQLQESGGG VVRPGGSLRL SCAASGFTFS DYYMSWIRQA PGKGLEWVSY ISSSGSTIYY         60
ADSVKGRFTI SRDNSKNTLY LQMNSLRAED TAVYYCARDY GRIAAAGRHY WGQGTLVTVS       120
S                                                                       121

SEQ ID NO: 38            moltype = AA  length = 109
FEATURE                  Location/Qualifiers
REGION                   1..109
                         note = Synthetic antibody VL domain
source                   1..109
                         mol_type = protein
                         organism = synthetic construct
SEQUENCE: 38
SSELTQDPAV SVALGQTVRI TCQGDSLRSY YASWYQQKPG QAPVLVIYGK NNRPSGIPDR         60
```

```
FSGSSSGNTA SLTITGAQAE DEADYYCNSR DSSGTHLEVF GGGTKVTVL              109

SEQ ID NO: 39           moltype = AA   length = 121
FEATURE                 Location/Qualifiers
REGION                  1..121
                        note = Synthetic antibody VH domain
source                  1..121
                        mol_type = protein
                        organism = synthetic construct
SEQUENCE: 39
EVQLVESGGG LVQPGGSLRL SCAASGFTFS DYYMSWIRQA PGKGLEWVSY ISSSGSTIYY   60
ADSVKGRFTI SRDNSKNTLY LQMNSLRAED TAVYYCARDY GRIAAAGRHY WGQGTLVTVS   120
S                                                                   121

SEQ ID NO: 40           moltype = AA   length = 107
FEATURE                 Location/Qualifiers
REGION                  1..107
                        note = Synthetic antibody VL domain
source                  1..107
                        mol_type = protein
                        organism = synthetic construct
SEQUENCE: 40
SSELTQDPAV SVALGQTVRI TCQGDTLSTY YANWYQQKPG QAPVLVIYGK NNRPSGIPDR   60
FSGSSSGNTA SLTITGAQAE DEADYYCHSR DISGNYLFAS GTKLTVL                 107

SEQ ID NO: 41           moltype = AA   length = 127
FEATURE                 Location/Qualifiers
REGION                  1..127
                        note = Synthetic antibody VH domain
source                  1..127
                        mol_type = protein
                        organism = synthetic construct
SEQUENCE: 41
QVQLQESGGG LVQPGGSLRL SCAASGFTFS SYWMSWVRQA PGKGLEWVAD IKQDGSEKYY   60
VDSVKGRFTI SGDNAKNSLY LQMNSLRAED TAVYYCAKDV GSTAINYVRA YTWFDPWGQG   120
TLVTVSS                                                             127

SEQ ID NO: 42           moltype = AA   length = 110
FEATURE                 Location/Qualifiers
REGION                  1..110
                        note = Synthetic antibody VL domain
source                  1..110
                        mol_type = protein
                        organism = synthetic construct
SEQUENCE: 42
QSVLTQPPSA SGTPGQRVTI SCSGSSSNIG SNTVNWSRQL PGTAPKLLIY SNNQRPSGVP   60
DRFSGSKSGT SASLAISGLQ SEDEADYYCA AWDDSLNVYV FGTGTKVTVL              110

SEQ ID NO: 43           moltype = AA   length = 122
FEATURE                 Location/Qualifiers
REGION                  1..122
                        note = Synthetic antibody VH domain
source                  1..122
                        mol_type = protein
                        organism = synthetic construct
SEQUENCE: 43
QVQLQESGGG LVQPGGSLRL SCAASGFTFS NYAMSWVRQA PGKGLEWVST ISGSGSSTFY   60
VDSVKGRFTI SRDNSKNTLY LQMNSLRAED TAVYYCAQGL YSSGWANWFD PRGQGTLVTV   120
SS                                                                  122

SEQ ID NO: 44           moltype = AA   length = 107
FEATURE                 Location/Qualifiers
REGION                  1..107
                        note = Synthetic antibody VL domain
source                  1..107
                        mol_type = protein
                        organism = synthetic construct
SEQUENCE: 44
KIVLTQSPSS LSASVGDTVT IACRASRDIR NDLAWYQQKP GKAPKLLIYG ASSLQSGVPS   60
RFSGSGSGTE FILTISSLQP EDFATYYCHR LNSYPLTFGG GTKVDIK                 107

SEQ ID NO: 45           moltype = AA   length = 123
FEATURE                 Location/Qualifiers
REGION                  1..123
                        note = Synthetic antibody VH domain
source                  1..123
                        mol_type = protein
                        organism = synthetic construct
SEQUENCE: 45
```

```
QVQLQESGGG VVQPGRSLRL SCAASGFTFS SYGMHWVRQA PGKGLEWVAV ISYDGSNKYY    60
ADSVKGRFTI SRDNSKNTLY LQMNSLRAED TAVYYCAKVM GLAAAGLDAF DIWGQGTTVT   120
VSS                                                                123

SEQ ID NO: 46           moltype = AA   length = 111
FEATURE                 Location/Qualifiers
REGION                  1..111
                        note = Synthetic antibody VL domain
source                  1..111
                        mol_type = protein
                        organism = synthetic construct
SEQUENCE: 46
NFMLTQPASL SGSPGQSITI SCTGTSSDVG GYNYVSWYQQ HPGYAPKLMI YDVSNRPSGV    60
SNRFSGSKSG NTASLTISGL QAEDEADYYC SSYTSSSTPW VFGGGTKLTV L            111

SEQ ID NO: 47           moltype = AA   length = 117
FEATURE                 Location/Qualifiers
REGION                  1..117
                        note = Synthetic antibody VH domain
source                  1..117
                        mol_type = protein
                        organism = synthetic construct
SEQUENCE: 47
QVQLVQSGGG VVQPGRSLRL SCAASGFTFS SYAMHWVRQA PGKGLEWVAV ISYDGSNKYY    60
ADSVKGRFTI SRDTSTNTLY LQMNSLRADD TAVYYCGRES SGSPGVWGQG TTVTVSS      117

SEQ ID NO: 48           moltype = AA   length = 106
FEATURE                 Location/Qualifiers
REGION                  1..106
                        note = Synthetic antibody VL domain
source                  1..106
                        mol_type = protein
                        organism = synthetic construct
SEQUENCE: 48
SYVLTQDPAV SVALGQTVRI TCQGDSLRSY YASWYQQKPG QAPVLVIYGK NNRPSGIPDR    60
FSGSSSGNTA SLTITGAQAE DEADYYCNSR DSSGNQFGGG TKLTVL                  106

SEQ ID NO: 49           moltype = AA   length = 122
FEATURE                 Location/Qualifiers
REGION                  1..122
                        note = Synthetic antibody VH domain
source                  1..122
                        mol_type = protein
                        organism = synthetic construct
SEQUENCE: 49
QVQLVESGGG LIQPGGSLRL SCAASGFTVS SNYMSWVRQA PGKGLEWVSV IYTDGSTYYA    60
DSVKGRFTIS RDNSKNTLYL QMNSLRAEDT AIYYCARDRG TSGYDWAWFD LWGQGTLVTV   120
SS                                                                 122

SEQ ID NO: 50           moltype = AA   length = 108
FEATURE                 Location/Qualifiers
REGION                  1..108
                        note = Synthetic antibody VL domain
source                  1..108
                        mol_type = protein
                        organism = synthetic construct
SEQUENCE: 50
SSELTQDPAV SVALGQTVRI TCQGDSLRTY YASWYQQRPG QAPILVLYGK NNRPSGIPDR    60
FSGSSSGNTA SLTITGAQAE DEADYYCNSR DSSGNHVVFG GGTKLTVL                108

SEQ ID NO: 51           moltype = AA   length = 123
FEATURE                 Location/Qualifiers
REGION                  1..123
                        note = Synthetic antibody VH domain
source                  1..123
                        mol_type = protein
                        organism = synthetic construct
SEQUENCE: 51
QVQLQESGGG LVQPGGSLRL SCAASGFTFS SYAMSWVRQA PGKGLEWVSA ISGSGGSTYY    60
ADSVKGRFTI SRDNSKNTLY MQMNSLRAED TAVYYCAKDR YYYGSGKDAF DIWGRGTMVT   120
VSS                                                                123

SEQ ID NO: 52           moltype = AA   length = 110
FEATURE                 Location/Qualifiers
REGION                  1..110
                        note = Synthetic antibody VL domain
source                  1..110
                        mol_type = protein
                        organism = synthetic construct
```

```
SEQUENCE: 52
QSVLTQPASV SGSPGQSITI SCTGTGSDVG SYNYVSWYQQ NPGKAPKLMI YEVSNRPSGV    60
SNRFSGSKSG NTASLTISGL QAEDEADYYC SSYTTSSTLV FGGGTKVTVL             110

SEQ ID NO: 53           moltype = AA  length = 118
FEATURE                 Location/Qualifiers
REGION                  1..118
                        note = Synthetic antibody VH domain
source                  1..118
                        mol_type = protein
                        organism = synthetic construct
SEQUENCE: 53
QVQLVESGGG LVQPGGSLGL SCAASGFTFS NYWMSWVRQA PGKGLEWVAN VRQDGGQKYY    60
VDSVKGRFTI SRDNAKNSLY LQMNSLRTED TAVYFCVSQR NSGEHDYWGQ GTLVTVSS    118

SEQ ID NO: 54           moltype = AA  length = 107
FEATURE                 Location/Qualifiers
REGION                  1..107
                        note = Synthetic antibody VL domain
source                  1..107
                        mol_type = protein
                        organism = synthetic construct
SEQUENCE: 54
SELTQDPAVS VALGQTVRIT CQGDSLRSYY ASWYQQKPGQ APVLVIYGEN SRPSGIPDRF    60
SGSSSGNTAS LTITGAQAED EADYYCNSWD SSGNHVVFGG GTKLTVL                107

SEQ ID NO: 55           moltype = AA  length = 121
FEATURE                 Location/Qualifiers
REGION                  1..121
                        note = Synthetic antibody VH domain
source                  1..121
                        mol_type = protein
                        organism = synthetic construct
SEQUENCE: 55
EVQLVESGGG LVQPGGSLRL SCAASGFTFS DYYMSWIRQA PGKGLEWVSY ISSSGSTIYY    60
ADSVKGRFTI SRDNSKNTLY LQMNSLRAED TAVYYCARDY GRIAAAGRHY WGQGTLVTVS  120
S                                                                  121

SEQ ID NO: 56           moltype = AA  length = 107
FEATURE                 Location/Qualifiers
REGION                  1..107
                        note = Synthetic antibody VL domain
source                  1..107
                        mol_type = protein
                        organism = synthetic construct
SEQUENCE: 56
AIRMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPRTFGQ GTKLEIK                107

SEQ ID NO: 57           moltype = AA  length = 121
FEATURE                 Location/Qualifiers
REGION                  1..121
                        note = Synthetic antibody VH domain
source                  1..121
                        mol_type = protein
                        organism = synthetic construct
SEQUENCE: 57
EVQLVESGGG LVQPGGSLRL SCAASGFTFS DYYMSWIRQA PGKGLEWVSY ISSSGSTIYY    60
ADSVKGRFTI SRDNSKNTLY LQMNSLRAED TAVYYCARDY GRIAAAGRNY WGQGTLVTVS  120
S                                                                  121

SEQ ID NO: 58           moltype = AA  length = 111
FEATURE                 Location/Qualifiers
REGION                  1..111
                        note = Synthetic antibody VL domain
source                  1..111
                        mol_type = protein
                        organism = synthetic construct
SEQUENCE: 58
DIVMTQSPLS LPVTPGEPAS ISCRSSQSLL HSNGYDYLDW YLQKPGQSPQ LLIYLGSNRA    60
SGVPDRFSGS GSGTDFTLKI SRVETEDVGI YYCMQGLQTP SFGQGTKLEI K           111

SEQ ID NO: 59           moltype = AA  length = 121
FEATURE                 Location/Qualifiers
REGION                  1..121
                        note = Synthetic antibody VH domain
source                  1..121
                        mol_type = protein
                        organism = synthetic construct
```

```
SEQUENCE: 59
QVQLQESGGG VVRPGGSLRL SCAASGFTFS DYYMSWIRQA PGKGLEWVSY ISSSGSTIYY      60
ADSVKGRFTI SRDNSKNTLY LQMNSLRAED TAVYYCARDY GRIAAAGRHY WGQGTLVTVS     120
S                                                                    121

SEQ ID NO: 60           moltype = AA   length = 109
FEATURE                 Location/Qualifiers
REGION                  1..109
                        note = Synthetic antibody VL domain
source                  1..109
                        mol_type = protein
                        organism = synthetic construct
SEQUENCE: 60
SSELTQDPAV SVALGQTVRI TCQGDSLRSY YASWYQQKPG QAPVPVIYGK NNRPSGIPDR      60
FSGSSSGNTA SLTITGAQAE DEADYYCNSR DSSSTHRGVF GGGTKLTVL                 109

SEQ ID NO: 61           moltype = AA   length = 121
FEATURE                 Location/Qualifiers
REGION                  1..121
                        note = Synthetic antibody VH domain
source                  1..121
                        mol_type = protein
                        organism = synthetic construct
SEQUENCE: 61
EVQLVESGGG LVKPGGSLRL SCAASGFTFS DYYMSWIRQA PGKGLEWVSY ISSSGSSIYY      60
ADSVKGRFTI SRDNAKNSLY LQMNSLKAED TAVYYCARDI TDVVGVSFDY WGQGTLVTVS     120
S                                                                    121

SEQ ID NO: 62           moltype = AA   length = 107
FEATURE                 Location/Qualifiers
REGION                  1..107
                        note = Synthetic antibody VL domain
source                  1..107
                        mol_type = protein
                        organism = synthetic construct
SEQUENCE: 62
DIQLTQSPSS LSASVGDRVT ITCRASRSIS TYLSWYQQKP GKAPKLLIYD ASRLQNGVPS      60
RFSGSGSDTD FTLTISSLQP EDFATYFCQQ SYNPPWTFGQ GTKLEIK                   107

SEQ ID NO: 63           moltype = AA   length = 123
FEATURE                 Location/Qualifiers
REGION                  1..123
                        note = Synthetic antibody VH domain
source                  1..123
                        mol_type = protein
                        organism = synthetic construct
SEQUENCE: 63
EVQLVESGGG VVQPGRSLRL SCAASGFTFS SYGMHWVRQA PGKGLEWVAV ISYDGSNKYY      60
ADSVKGRFTI SRDNSKNTLY LQMNSLRAED TAEYYCAKVM GLAAAGLDAF DIWGQGTLVT     120
VSS                                                                  123

SEQ ID NO: 64           moltype = AA   length = 111
FEATURE                 Location/Qualifiers
REGION                  1..111
                        note = Synthetic antibody VL domain
source                  1..111
                        mol_type = protein
                        organism = synthetic construct
SEQUENCE: 64
QSALTQPASV SGSPGQSITI SCTGTSSDVG GYNYVSWYQQ HPGKAPKLMI YDVSNRPSGV      60
SNRFSGSKSG NTASLTISGL QAEDEAYYYC SSYTSSSDPW VFGGGTQLTV L              111

SEQ ID NO: 65           moltype = AA   length = 123
FEATURE                 Location/Qualifiers
REGION                  1..123
                        note = Synthetic antibody VH domain
source                  1..123
                        mol_type = protein
                        organism = synthetic construct
SEQUENCE: 65
EVQLVESGGG VVQPGRSLRL SCAASGFTFS SFGMHWVRRA PGKGLEWVAV ISYDGSNQYY      60
ADSVKGRFTI SRDNSKNTLY LQMNSLRAED TAVYYCGSRP GGGYASGSTV AYWGQGTLVT     120
VSS                                                                  123

SEQ ID NO: 66           moltype = AA   length = 107
FEATURE                 Location/Qualifiers
REGION                  1..107
                        note = Synthetic antibody VL domain
source                  1..107
```

```
                         mol_type = protein
                         organism = synthetic construct
SEQUENCE: 66
NIQMTQSPSS LSASVGDRVT ITCRAGQPIS TYVNWYQHKP GKAPKLLIYG ASNLQSGVPS    60
RFSGGGSATD FTLTISSLQP EDFATYYCQQ SYSSLLTFGD GTKVEIK                 107

SEQ ID NO: 67            moltype = AA   length = 119
FEATURE                  Location/Qualifiers
REGION                   1..119
                         note = Synthetic antibody VH domain
source                   1..119
                         mol_type = protein
                         organism = synthetic construct
SEQUENCE: 67
QVQLQEPGGG LVQPGRSLRL SCAASGFTFD DYAMHWVRQA PGKGLEWVGR IKSKTDEGTT    60
DYAAPVKGRF SISRDDSKNT LYLQMNSLKT EDTGVYYCTA TKGLGGSKLG QGTLVTVSS    119

SEQ ID NO: 68            moltype = AA   length = 110
FEATURE                  Location/Qualifiers
REGION                   1..110
                         note = Synthetic antibody VL domain
source                   1..110
                         mol_type = protein
                         organism = synthetic construct
SEQUENCE: 68
QSVLTQPPSA SGTPGQRVTI SCSGSSSNIG SNTVSWSRQL PGTAPKLLIY SNDQRPSGVP    60
DRFSGSKSGT SASLAITGLQ PEDEADYYCG TWDSSLSAYV FGTGTKLTVL              110

SEQ ID NO: 69            moltype = AA   length = 119
FEATURE                  Location/Qualifiers
REGION                   1..119
                         note = Synthetic antibody VH domain
source                   1..119
                         mol_type = protein
                         organism = synthetic construct
SEQUENCE: 69
QVQLQESGGG LVKPGGSLRL SCAASGFTFS NAWMNWVRQA PGKGLEWVGR IKSKTDEGTT    60
DYAAPVKGRF SISRDDSKNT LYLQMNSLKT EDTGVYYCTA TKGLGGSKLG QGTLVTVSS    119

SEQ ID NO: 70            moltype = AA   length = 110
FEATURE                  Location/Qualifiers
REGION                   1..110
                         note = Synthetic antibody VL domain
source                   1..110
                         mol_type = protein
                         organism = synthetic construct
SEQUENCE: 70
QSVLTQPPSA SGTPGQRVTI SCSGSSSNIG NNTVNWSRQL PGTAPKLLIY SNDQRPSGVP    60
DRFSGSKSGT SASLAITGLQ PEDEADYYCG TWDSSLSAYV FGTGTKLTVL              110

SEQ ID NO: 71            moltype = AA   length = 115
FEATURE                  Location/Qualifiers
REGION                   1..115
                         note = Synthetic antibody VH domain
source                   1..115
                         mol_type = protein
                         organism = synthetic construct
SEQUENCE: 71
QVQLVESGGG LVQPGGSLRL SCAASGFTFS SYAMGWVRQA PGKGLEWVSA ISGSGGSTYY    60
ADSVKGRFTI SRDNSKDTLY LQMNSLRAED TAVYYCASRS LLDYWGQGTL VTVSS        115

SEQ ID NO: 72            moltype = AA   length = 107
FEATURE                  Location/Qualifiers
REGION                   1..107
                         note = Synthetic antibody VL domain
source                   1..107
                         mol_type = protein
                         organism = synthetic construct
SEQUENCE: 72
NFMLTQDPAV SVALGQTVRI TCQGDSLRSY YASWYQQKPG QAPLLVIYGK NNRPSGIPDR    60
FSGSSSGNTA SLTITGAQAE DEADYYCNSR DSSGNPVFGG GTKVTVL                 107

SEQ ID NO: 73            moltype = AA   length = 115
FEATURE                  Location/Qualifiers
REGION                   1..115
                         note = Synthetic antibody VH domain
source                   1..115
                         mol_type = protein
                         organism = synthetic construct
```

```
SEQUENCE: 73
QVQLVESGGG LVQPGGSLRL SCAASGFTFS SYAMSWVRQA PGKGLEWVSA ISGSGGSTYY    60
ADSVKGRFTI SRDNSKDTLY LQMNSLRAED TAVYYCASRS LLDYWGQGTL VTVSS        115

SEQ ID NO: 74           moltype = AA  length = 107
FEATURE                 Location/Qualifiers
REGION                  1..107
                        note = Synthetic antibody VL domain
source                  1..107
                        mol_type = protein
                        organism = synthetic construct
SEQUENCE: 74
NFMLTQDPAV SVALGQTVRI TCQGDSLRSY YASWYQQKPG QAPLLVIYGK NNRPSGIPDR    60
FSGSSSGNTA SLTITGAQAE DEADYYCNSR DSSGNPVFGG GTKVTVL                 107

SEQ ID NO: 75           moltype = AA  length = 32
FEATURE                 Location/Qualifiers
source                  1..32
                        mol_type = protein
                        organism = Homo sapiens
SEQUENCE: 75
KPYYEIGERV DYKCKKGYFY IPPLATHTIC DR                                 32
```

ANTI-CD46 ANTIBODIES AND METHODS OF USE

CROSS-REFERENCE TO RELATED APPLICATIONS

This application is a divisional of U.S. Ser. No. 16/348,135, filed on May 7, 2019, which is a U.S. 371 National Phase of PCT/US2017/061124, filed on Nov. 10, 2017, which claims benefit of and priority to U.S. Ser. No. 62/421,113, filed on Nov. 11, 2016, each of which is incorporated herein by reference in its entirety for all purposes.

STATEMENT OF GOVERNMENTAL SUPPORT

This invention was made with government support under grant nos. R01 CA118919, R01 CA129491, and R01 CA171315, awarded by the National Institutes of Health. The government has certain rights in the invention.

INCORPORATION BY REFERENCE OF SEQUENCE LISTING PROVIDED AS A TEXT FILE

This application contains references to nucleic acid sequences and/or to amino acid sequences that have been submitted herewith as an XML file, "UCSFP039D1US_SQL.xml", file size 95,888 bytes, created on Jul. 25, 2022, which is incorporated herein by reference in its entirety pursuant to 37 CFR 1.839.

BACKGROUND

Cancer is a large and heterogeneous group of diseases, often with treatment response and outcome dependent on the specific type of malignancy. Chromosomal abnormalities are useful markers for diagnosis and cancer therapy.

SUMMARY

Various embodiments contemplated herein may include, but need not be limited to, one or more of the following:

Embodiment 1: A method of treating a subject having a cancer characterized by a modification at chromosome location 1q21, comprising:
administering to the subject identified to have a modification at chromosome location 1q21 a therapeutically effective amount of a CD46-targeted therapy.

Embodiment 2: The method of embodiment 1, wherein the modification at 1q21 is an amplification of 1q21.

Embodiment 3: The method of embodiment 2, wherein the modification at 1q21 is copy number gain of 1q21.

Embodiment 4: The method of embodiment 3, wherein the modification at 1q21 is a gain of at least 1, 2, 3, 4, or more copy numbers.

Embodiment 5: The method of any one of the embodiments 1-4, further comprising a modification at biomarker Myeloid Cell Leukemia-1 (MCL1).

Embodiment 6: The method of embodiment 5, wherein the modification at MCL1 is an amplification of the MCL1 gene.

Embodiment 7: The method of any one of the embodiments 1-6, further comprising an increase in CD46 mRNA expression in the subject, wherein the increase in CD46 mRNA expression is relative to a control subject who does not have a modification at 1q21.

Embodiment 8: The method of embodiment 1, wherein the subject has a cancer characterized by an amplification at 1q21.

Embodiment 9: The method of embodiment 1, or 8, wherein the cancer is further characterized by an amplification of CD46.

Embodiment 10: The method of embodiment 1, or 9, wherein the subject has a mean CD46 antigen density on cancer cells of at least 200,000, at least 250,000, at least 300,000, at least 350,000, or more.

Embodiment 11: The method of embodiment 1-10, further comprising testing the sample comprising a nucleic acid molecule encoding a region of a chromosome at 1q21 obtained from the subject, and determining whether 1q21 comprises a modification.

Embodiment 12: The method of embodiment 11, wherein the nucleic acid molecule is DNA.

Embodiment 13: The method of embodiment 11, wherein the nucleic acid molecule is genomic DNA.

Embodiment 14: The method of any one of the embodiments 11-13, wherein testing comprises amplifying the nucleic acid molecule encoding the region of a chromosome at 1q21.

Embodiment 15: The method of embodiment 14, wherein the amplifying is by isothermal amplification.

Embodiment 16: The method of embodiment 14, wherein the amplifying is by polymerase chain reaction (PCR).

Embodiment 17: The method of any one of embodiments embodiment 1-16, wherein the CD46-targeted therapy comprises a pharmaceutical composition comprising an anti-CD46 antibody.

Embodiment 18: The method of embodiment 17, wherein the anti-CD46 antibody binds to an epitope of CD46 bound by one or more antibodies selected from 3051.1, G12FC3, M6c42b, 4F3YW, M40pr146, UA8, 585II56, 3076, 3051, M49R, RCI-14, 1179-4, 1179-3, T5II-4B.1, T5II-4B.2, RCI-11, RCI-20, CI-11A, CI-14A, 595-2, and mPA7.

Embodiment 19: The method of embodiment 17, wherein the anti-CD46 antibody binds to an epitope of CD46 bound by one or more antibodies selected from SEQ ID NOs: 1, 2, 9, 10, 17, 18, 25, 26, or 33-74.

Embodiment 20: The method of embodiment 17, wherein the anti-CD46 antibody binds to at least a portion of sushi domain 1 of CD46 comprising the amino acid sequence of SEQ ID NO: 75.

Embodiment 21: The method of embodiment 17, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 3, a variable heavy (VH) CDR2 that comprises an amino acid sequence of SEQ ID NO: 4, and a variable heavy (VH) CDR3 that comprises an amino acid sequence of SEQ ID NO: 5.

Embodiment 22: The method of embodiment 17, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 6, a variable light (VL) CDR 2 that comprises an amino acid sequence of SEQ ID NO: 7, and a variable light (VL) CDR 3 that comprises an amino acid sequence of SEQ ID NO: 8.

Embodiment 23: The method of embodiment 17, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 3, a variable heavy (VH) CDR2 that comprises an amino acid sequence of SEQ ID NO: 4, and a variable heavy (VH) CDR3 that comprises an amino acid sequence of SEQ ID NO: 5, and wherein the light chain variable region comprises a variable light (VL) CDR 1 that comprises an amino acid sequence of SEQ ID NO: 6, a variable light (VL) CDR 2 that comprises an amino acid sequence of SEQ ID NO: 7, and a variable light (VL) CDR 3 that comprises an amino acid sequence of SEQ ID NO: 8.

Embodiment 24: The method of embodiment 17, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 11, a variable heavy (VH) CDR2 that comprises an amino acid sequence of SEQ ID NO: 12, and a variable heavy (VH) CDR3 that comprises an amino acid sequence of SEQ ID NO: 13.

Embodiment 25: The method of embodiment 17, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 14, a variable light (VL) CDR 2 that comprises an amino acid sequence of SEQ ID NO: 15, and a variable light (VL) CDR 3 that comprises an amino acid sequence of SEQ ID NO: 16.

Embodiment 26: The method of embodiment 17, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 11, a variable heavy (VH) CDR2 that comprises an amino acid sequence of SEQ ID NO: 12, and a variable heavy (VH) CDR3 that comprises an amino acid sequence of SEQ ID NO: 13, and wherein the light chain variable region comprises a variable light (VL) CDR 1 that comprises an amino acid sequence of SEQ ID NO: 14, a variable light (VL) CDR 2 that comprises an amino acid sequence of SEQ ID NO: 15, and a variable light (VL) CDR 3 that comprises an amino acid sequence of SEQ ID NO: 16.

Embodiment 27: The method of embodiment 17, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 19, a variable heavy (VH) CDR2 that comprises an amino acid sequence of SEQ ID NO: 20, and a variable heavy (VH) CDR3 that comprises an amino acid sequence of SEQ ID NO: 21.

Embodiment 28: The method of embodiment 17, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 22, a variable light (VL) CDR 2 that comprises an amino acid sequence of SEQ ID NO: 23, and a variable light (VL) CDR 3 that comprises an amino acid sequence of SEQ ID NO: 24.

Embodiment 29: The method of embodiment 17, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 19, a variable heavy (VH) CDR2 that comprises an amino acid sequence of SEQ ID NO: 20, and a variable heavy (VH) CDR3 that comprises an amino acid sequence of SEQ ID NO: 21, and wherein the light chain variable region comprises: a variable light (VL) CDR 1 that comprises an amino acid sequence of SEQ ID NO: 22, a variable light (VL) CDR 2 that comprises an amino acid sequence of SEQ ID NO: 23, and a variable light (VL) CDR 3 that comprises an amino acid sequence of SEQ ID NO: 24.

Embodiment 30: The method of embodiment 17, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 27, a variable heavy (VH) CDR2 that comprises an amino acid sequence of SEQ ID NO: 28, and a variable heavy (VH) CDR3 that comprises an amino acid sequence of SEQ ID NO: 29.

Embodiment 31: The method of embodiment 17, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 30, a variable light (VL) CDR 2 that comprises an amino acid sequence of SEQ ID NO: 31, and a variable light (VL) CDR 3 that comprises an amino acid sequence of SEQ ID NO: 32.

Embodiment 32: The method of embodiment 17, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 27, a variable heavy (VH) CDR2 that comprises an amino acid sequence of SEQ ID NO: 28, and a variable heavy (VH) CDR3 that comprises an amino acid sequence of SEQ ID NO: 29, and wherein the light chain variable region comprises a variable light (VL) CDR 1 that comprises an amino acid sequence of SEQ ID NO: 30, a variable light (VL) CDR 2 that comprises an amino acid sequence of SEQ ID NO: 31, and a variable light (VL) CDR 3 that comprises an amino acid sequence of SEQ ID NO: 32.

Embodiment 33: The method of any one of the embodiments 17, or 21-32, wherein the anti-CD46 antibody comprises a heavy chain variable region having at least 80%, 85%, 90%, 95%, or 99% sequence identity to SEQ ID NOs: 1, 9, 17 and 25; and a light chain variable region having at least 80%, 85%, 90%, 95%, or 99% sequence identity to SEQ ID NOs: 2, 10, 18 and 26.

Embodiment 34: The method of one of the embodiments 17, or 21-33, wherein the anti-CD46 antibody comprises a heavy chain variable region comprising the amino acid sequence of SEQ ID NO: 1 and a light chain variable region comprising the amino acid sequence of SEQ ID NO: 2.

Embodiment 35: The method of any one of the embodiments 17-34, wherein the anti-CD46 antibody comprises a humanized antibody or binding fragment thereof, a chimeric antibody or binding fragment thereof, a monoclonal antibody or binding fragment thereof, a bispecific antibody or binding fragment thereof, an Fab, an Fab', an F(ab')$_2$, an F(ab')$_3$, an scFv, an sc(Fv)$_2$, a dsFv, a diabody, a minibody, and a nanobody or binding fragments thereof.

Embodiment 36: The method of any one of the embodiments 17-35, wherein the anti-CD46 antibody comprises an Fab, an Fab', an F(ab')$_2$, an F(ab')$_3$, an scFv, an sc(Fv)$_2$, a dsFv and a diabody or binding fragments thereof.

Embodiment 37: The method of any one of the embodiments 17-35, wherein the anti-CD46 antibody comprises a full-length immunoglobulin.

Embodiment 38: The method of any one of the embodiments 17-35, wherein the anti-CD46 antibody comprises a bispecific antibody or binding fragment thereof.

Embodiment 39: The method of embodiment 38, wherein the bispecific antibody or binding fragment thereof further binds to a cancer marker that is different from CD46.

Embodiment 40: The method of any one of the embodiments 17-39, wherein the anti-CD46 antibody further comprises at least one payload.

Embodiment 41: The method of embodiment 40, wherein the at least one payload comprises a cytotoxic or cytostatic drug.

Embodiment 42: The method of embodiment 40, or 41, wherein the at least one payload comprises a microtubule inhibitor, a DNA-damaging agent, or a polymerase inhibitor.

Embodiment 43: The method of embodiment 40, or 41, wherein the at least one payload comprises a tubulin inhibitor.

Embodiment 44: The method of any one of the embodiments 40-43, wherein the at least one payload comprises Monomethylauristatin F (MMAF), Auristatin E (AE), or Monomethylauristatin E (MMAE).

Embodiment 45: The method of any one of the embodiments 40-43, wherein the at least one payload comprises Mertansine (DM1), DM3, or DM4.

Embodiment 46: The method of any one of the embodiments 40-43, wherein the at least one payload comprises a calicheamicin, a duocamycin, a pyrrolobenzodiazepine, or a derivative thereof.

Embodiment 47: The method of any one of the embodiments 40-43, wherein the at least one payload comprises duocarmycin A, duocarmycin B 1, duocarmycin B2, duocarmycin CI, duocarmycin C2, duocarmycin D, duocarmycin SA, Cyclopropylbenzoindole duocarmycin (CC-1065), Centanamycin, Rachelmycin, Adozelesin, Bizelesin or Carzelesin.

Embodiment 48: The method of any one of the embodiments 40-43, wherein the at least one payload comprises Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, or SG2285.

Embodiment 49: The method of any one of the embodiments 40-43, wherein the at least one payload comprises flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (R R), cyclophosphamide, neosar, ifosfamide, thiotepa, 1,3-bis(2-chloroethyl)-1-nitosourea (BCNU), 1,-(2-chloroethyl)-3-cyclohexyl-1nitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, trip latin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, doxorubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, or zoledronic acid.

Embodiment 50: The method of embodiment 40, or 41, wherein the at least one payload comprises a cytokine, a radiosensitizer, or an immunomodulator.

Embodiment 51: The method of embodiment 40, 41, or 50, wherein the at least one payload comprises a cytokine.

Embodiment 52: The method of embodiment 51, wherein the cytokine comprises IL-2, IL-2, IL-3, IL-6, IL-10, IL-12, IL-18, IL-21, or TNFα.

Embodiment 53: The method of embodiment 40, 41, or 50, wherein the at least one payload comprises a radiosensitizer.

Embodiment 54: The method of embodiment 53, wherein the radiosensitizer comprises a benzoporphyrin derivative compound, 1,2,4-benzotriazine oxide or nitrobenzoic acid amide derivative.

Embodiment 55: The method of embodiment 40, 41, or 50, wherein the at least one payload comprises an imaging agent.

Embodiment 56: The method of embodiment 40, 41, or 50, wherein the at least one payload comprises an immunomodulator.

Embodiment 57: The method of embodiment 56, wherein the immunomodulator comprises an anti-CTLA4 antibody or binding fragment thereof, an anti-PD-L1 antibody or binding fragment thereof, or an anti-PD-L2 antibody or binding fragment thereof.

Embodiment 58: The method of embodiment 40, 41, or 50, wherein the at least one payload comprises a modified effector cell.

Embodiment 59: The method of embodiment 58, wherein the modified effector cell comprises a CAR-T cell or a CAR-NK cell.

Embodiment 60: The method of any one of the embodiments 1-50, wherein the anti-CD46 antibody further comprises two or more payloads.

Embodiment 61: The method of embodiment 60, wherein the two or more payloads are the same.

Embodiment 62: The method of embodiment 60, wherein the two or more payloads are different.

Embodiment 63: The method of any one of the embodiments 1-62, wherein the cancer is multiple myeloma, breast cancer, or liver cancer.

Embodiment 64: The method of any one of the embodiments 1-63, wherein the cancer is a relapsed or refractory cancer.

Embodiment 65: The method of any one of the embodiments 1-64, wherein the cancer is a metastatic cancer.

Embodiment 66: The method of any one of the embodiments 1-62, wherein the cancer is multiple myeloma.

Embodiment 67: The method of embodiment 66, wherein the multiple myeloma is a relapsed or refractory multiple myeloma.

Embodiment 68: The method of any one of the embodiments 1-67, wherein the anti-CD46 antibody is formulated for parenteral administration.

Embodiment 69: The method of any one of the embodiments 1-68, wherein the anti-CD46 antibody is administered to the subject as an injection.

Embodiment 70: The method of any one of the embodiments 1-68, wherein the anti-CD46 antibody is administered to the subject as an infusion.

Embodiment 71: The method of any one of the embodiments 1-70, wherein the subject is a human.

Embodiment 72: The method of any one of the embodiments 1-70, wherein the subject is a non-human mammal.

Embodiment 73: A method of treating a subject having multiple myeloma characterized by a modification at chromosome location 1q21, comprising:
administering to the subject identified to have multiple myeloma and a modification at chromosome location 1q21 a therapeutically effective amount of a CD46-targeted therapy.

Embodiment 74: The method of embodiment 73, wherein the modification at 1q21 is an amplification of 1q21.

Embodiment 75: The method of embodiment 74, wherein the modification at 1q21 is copy number gain of 1q21.

Embodiment 76: The method of embodiment 75, wherein the modification at 1q21 is a gain of at least 1, 2, 3, 4, or more copy numbers.

Embodiment 77: The method of any one of the embodiments 73-76, further comprising a modification at biomarker Myeloid Cell Leukemia-1 (MCL1).

Embodiment 78: The method of embodiment 77, wherein the modification at MCL1 is an amplification of the MCL1 gene.

Embodiment 79: The method of any one of the embodiments 73-78, further comprising an increase in CD46 mRNA expression in the subject, wherein the increase in CD46 mRNA expression is relative to a control subject who does not have a modification at 1q21.

Embodiment 80: The method of embodiment 73, wherein the subject has a cancer characterized by an amplification at 1q21.

Embodiment 81: The method of embodiment 73, or 80, wherein the cancer is further characterized by an amplification of CD46.

Embodiment 82: The method of embodiment 73, or 81, wherein the subject has a mean CD46 antigen density on cancer cells of at least 200,000, at least 250,000, at least 300,000, at least 350,000, or more.

Embodiment 83: The method of any one of embodiments 73-82, further comprising testing the sample comprising a nucleic acid molecule encoding a region of a chromosome at 1q21 obtained from the subject, and determining whether 1q21 comprises a modification.

Embodiment 84: The method of embodiment 83, wherein the nucleic acid molecule is DNA.

Embodiment 85: The method of embodiment 84, wherein the nucleic acid molecule is genomic DNA.

Embodiment 86: The method of any one of the embodiments 83-85, wherein testing comprises amplifying the nucleic acid molecule encoding the region of a chromosome at 1q21.

Embodiment 87: The method of embodiment 86, wherein the amplifying is by isothermal amplification.

Embodiment 88: The method of embodiment 86, wherein the amplifying is by polymerase chain reaction (PCR).

Embodiment 89: The method of any one of embodiments 73-88, wherein the CD46-targeted therapy comprises a pharmaceutical composition comprising an anti-CD46 antibody.

Embodiment 90: The method of embodiment 89, wherein the anti-CD46 antibody binds to an epitope of CD46 bound by one or more antibodies selected from 3051.1, G12FC3, M6c42b, 4F3YW, M40pr146, UA8, 585II56, 3076, 3051, M49R, RCI-14, 1179-4, 1179-3, T5II-4B.1, T5II-4B.2, RCI-11, RCI-20, CI-11A, CI-14A, 595-2, and mPA7.

Embodiment 91: The method of embodiment 89, wherein the anti-CD46 antibody binds to an epitope of CD46 bound by one or more antibodies selected from SEQ ID NOs: 1, 2, 9, 10, 17, 18, 25, 26 or 33-74.

Embodiment 92: The method of embodiment 89, wherein the anti-CD46 antibody binds to at least a portion of sushi domain 1 of CD46 comprising the amino acid sequence of SEQ ID NO: 75.

Embodiment 93: The method of embodiment 89, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 3, a variable heavy (VH) CDR2 that comprises an amino acid sequence of SEQ ID NO: 4, and a variable heavy (VH) CDR3 that comprises an amino acid sequence of SEQ ID NO: 5.

Embodiment 94: The method of embodiment 89, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 6, a variable light (VL) CDR 2 that comprises an amino acid sequence of SEQ ID NO: 7, and a variable light (VL) CDR 3 that comprises an amino acid sequence of SEQ ID NO: 8.

Embodiment 95: The method of embodiment 89, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 3, a variable heavy (VH) CDR2 that comprises an amino acid sequence of SEQ ID NO: 4, and a variable heavy (VH) CDR3 that comprises an amino acid sequence of SEQ ID NO: 5, and wherein the light chain variable region comprises a variable light (VL) CDR 1 that comprises an amino acid sequence of SEQ ID NO: 6, a variable light (VL) CDR 2 that comprises an amino acid sequence of SEQ ID NO: 7, and a variable light (VL) CDR 3 that comprises an amino acid sequence of SEQ ID NO: 8.

Embodiment 96: The method of embodiment 89, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 11, a variable heavy (VH) CDR2 that comprises an amino acid sequence of SEQ ID NO: 12, and a variable heavy (VH) CDR3 that comprises an amino acid sequence of SEQ ID NO: 13.

Embodiment 97: The method of embodiment 89, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 14, a variable light (VL) CDR 2 that comprises an amino acid sequence of SEQ ID NO: 15, and a variable light (VL) CDR 3 that comprises an amino acid sequence of SEQ ID NO: 16.

Embodiment 98: The method of embodiment 89, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 11, a variable heavy (VH) CDR2 that comprises an amino acid sequence of SEQ ID NO: 12, and a variable heavy (VH) CDR3 that comprises an amino acid sequence of SEQ ID NO: 13, and wherein the light chain variable region comprises a variable light (VL) CDR 1 that comprises an amino acid sequence of SEQ ID NO: 14, a variable light (VL) CDR 2 that comprises an amino acid sequence of SEQ ID NO: 15, and a variable light (VL) CDR 3 that comprises an amino acid sequence of SEQ ID NO: 16.

Embodiment 99: The method of embodiment 89, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 19, a variable heavy (VH) CDR2 that comprises an amino acid sequence of SEQ ID NO: 20, and a variable heavy (VH) CDR3 that comprises an amino acid sequence of SEQ ID NO: 21.

Embodiment 100: The method of embodiment 89, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 22, a variable light (VL) CDR 2 that comprises an amino acid sequence of SEQ ID NO: 23, and a variable light (VL) CDR 3 that comprises an amino acid sequence of SEQ ID NO: 24.

Embodiment 101: The method of embodiment 89, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 19, a variable heavy (VH) CDR2 that comprises an amino acid sequence of SEQ ID NO: 20, and a variable heavy (VH) CDR3 that comprises an amino acid sequence of SEQ ID NO: 21, and wherein the light chain variable region comprises a variable light (VL) CDR 1 that comprises an amino acid sequence of SEQ ID NO: 22, a variable light (VL) CDR 2 that comprises an amino acid sequence of SEQ ID NO: 23, and a variable light (VL) CDR 3 that comprises an amino acid sequence of SEQ ID NO: 24.

Embodiment 102: The method of embodiment 89, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 27, a variable heavy (VH) CDR2 that comprises an amino acid sequence of SEQ ID NO: 28, and a variable heavy (VH) CDR3 that comprises an amino acid sequence of SEQ ID NO: 29.

Embodiment 103: The method of embodiment 89, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 30, a variable light (VL) CDR 2 that comprises an amino acid sequence of SEQ ID NO: 31, and a variable light (VL) CDR 3 that comprises an amino acid sequence of SEQ ID NO: 32.

Embodiment 104: The method of embodiment 89, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 27, a variable heavy (VH) CDR2 that comprises an amino acid sequence of SEQ ID NO: 28, and a variable heavy (VH) CDR3 that comprises an amino acid sequence of SEQ ID NO: 29, and wherein the light chain variable region comprises a variable light (VL) CDR 1 that comprises an amino acid sequence of SEQ ID NO: 30, a variable light (VL) CDR 2 that comprises an amino acid sequence of SEQ ID NO: 31, and a variable light (VL) CDR 3 that comprises an amino acid sequence of SEQ ID NO: 32.

Embodiment 105: The method of any one of the embodiments 89, or 93-104, wherein the anti-CD46 antibody comprises a heavy chain variable region having at least 80%, 85%, 90%, 95%, or 99% sequence identity to SEQ ID NOs: 1, 9, 17, and 25; and a light chain variable region having at least 80%, 85%, 90%, 95%, or 99% sequence identity to SEQ ID NOs: 2, 10, 18, and 26.

Embodiment 106: The method of one of the embodiments 89, or 93-105, wherein the anti-CD46 antibody comprises a heavy chain variable region comprising the amino acid sequence of SEQ ID NO: 1 and a light chain variable region comprising the amino acid sequence of SEQ ID NO: 2.

Embodiment 107: The method of any one of the embodiments 89-106, wherein the anti-CD46 antibody comprises a humanized antibody or binding fragment thereof, a chimeric antibody or binding fragment thereof, a monoclonal antibody or binding fragment thereof, a bispecific antibody or binding fragment thereof, an Fab, an Fab', an F(ab')$_2$, an F(ab')$_3$, an scFv, an sc(Fv)$_2$, a dsFv, a diabody, a minibody, and a nanobody or binding fragments thereof.

Embodiment 108: The method of any one of the embodiments 89-107, wherein the anti-CD46 antibody comprises an Fab, an Fab', an F(ab')$_2$, an F(ab')$_3$, an scFv, an sc(Fv)$_2$, a dsFv, and a diabody or binding fragments thereof.

Embodiment 109: The method of any one of the embodiments 89-107, wherein the anti-CD46 antibody comprises a full-length immunoglobulin.

Embodiment 110: The method of any one of the embodiments 89-107, wherein the anti-CD46 antibody comprises a bispecific antibody or binding fragment thereof.

Embodiment 111: The method of embodiment 110, wherein the bispecific antibody or binding fragment thereof further binds to a cancer marker that is different from CD46.

Embodiment 112: The method of any one of the embodiments 89-111, wherein the anti-CD46 antibody further comprises at least one payload.

Embodiment 113: The method of embodiment 112, wherein the at least one payload comprises a cytotoxic or cytostatic drug.

Embodiment 114: The method of embodiment 112, or 113, wherein the at least one payload comprises a microtubule inhibitor, a DNA-damaging agent, or a polymerase inhibitor.

Embodiment 115: The method of embodiment 112, or 113, wherein the at least one payload comprises a tubulin inhibitor.

Embodiment 116: The method of any one of the embodiments 112-115, wherein the at least one payload comprises Monomethylauristatin F (MMAF), Auristatin E (AE) or Monomethylauristatin E (MMAE).

Embodiment 117: The method of any one of the embodiments 112-115, wherein the at least one payload comprises Mertansine (DM1), DM3, or DM4.

Embodiment 118: The method of any one of the embodiments 112-115, wherein the at least one payload comprises a calicheamicin, a duocamycin, a pyrrolobenzodiazepine, or a derivative thereof.

Embodiment 119: The method of any one of the embodiments 112-115, wherein the at least one payload comprises duocarmycin A, duocarmycin B 1, duocarmycin B2, duocarmycin CI, duocarmycin C2, duocarmycin D, duocarmycin SA, Cyclopropylbenzoindole duocarmycin (CC-1065), Centanamycin, Rachelmycin, Adozelesin, Bizelesin, or Carzelesin.

Embodiment 120: The method of any one of the embodiments 112-115, wherein the at least one payload comprises Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, or SG2285.

Embodiment 121: The method of any one of the embodiments 112-115, wherein the at least one payload comprises flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (R R), cyclophosphamide, neosar, ifosfamide, thiotepa, 1,3-bis(2-chloroethyl)-1-nitosourea (BCNU), 1,-(2-chloroethyl)-3-cyclohexyl-1nitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, trip latin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, doxorubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, or zoledronic acid.

Embodiment 122: The method of embodiment 112, or 113, wherein the at least one payload comprises a cytokine, a radiosensitizer, or an immunomodulator.

Embodiment 123: The method of embodiment 112, 113, or 122, wherein the at least one payload comprises a cytokine.

Embodiment 124: The method of embodiment 123, wherein the cytokine comprises IL-2, IL-2, IL-3, IL-6, IL-10, IL-12, IL-18, IL-21, or TNFα.

Embodiment 125: The method of embodiment 112, 113, or 122, wherein the at least one payload comprises a radiosensitizer.

Embodiment 126: The method of embodiment 125, wherein the radiosensitizer comprises a benzoporphyrin derivative compound, 1,2,4-benzotriazine oxide or nitrobenzoic acid amide derivative.

Embodiment 127: The method of embodiment 112, 113, or 122, wherein the at least one payload comprises an imaging agent.

Embodiment 128: The method of embodiment 112, 113, or 122, wherein the at least one payload comprises an immunomodulator.

Embodiment 129: The method of embodiment 128, wherein the immunomodulator comprises an anti-CTLA4 antibody or binding fragment thereof, an anti-PD-L1 antibody or binding fragment thereof, or an anti-PD-L2 antibody or binding fragment thereof.

Embodiment 130: The method of embodiment 112, 113, or 122, wherein the at least one payload comprises a modified effector cell.

Embodiment 131: The method of embodiment 130, wherein the modified effector cell comprises a CAR-T cell or a CAR-NK cell.

Embodiment 132: The method of any one of the embodiments 73-122, wherein the anti-CD46 antibody further comprises two or more payloads.

Embodiment 133: The method of embodiment 132, wherein the two or more payloads are the same.

Embodiment 134: The method of embodiment 132, wherein the two or more payloads are different.

Embodiment 135: The method of embodiment 73, wherein the multiple myeloma is a relapsed or refractory multiple myeloma.

Embodiment 136: The method of any one of the embodiments 73-135, wherein the anti-CD46 antibody is formulated for parenteral administration.

Embodiment 137: The method of any one of the embodiments 73-136, wherein the anti-CD46 antibody is administered to the subject as an injection.

Embodiment 138: The method of any one of the embodiments 73-136, wherein the anti-CD46 antibody is administered to the subject as an infusion.

Embodiment 139: The method of any one of the embodiments 73-138, wherein the subject is a human.

Embodiment 140: A kit for carrying out the method of any one of the embodiments 1-139, comprising one or more reagents for determining the presence or absence of a modification at chromosome location 1q21 in the sample.

Embodiment 141: A method of determining whether a cancer in a subject is responsive to a CD46-targeted therapy, comprising:
providing a biological sample from the subject comprising cancer cells; and determining whether nucleic acid in the cancer cells show a modification at chromosome location 1q21;

wherein a modification at chromosome location 1q21 indicates that the cancer is responsive to the CD46-targeted therapy.

Embodiment 142: The method of embodiment 141, wherein the modification at 1q21 is copy number gain of 1q21.

Embodiment 143: The method of embodiment 141, wherein the cancer cells further comprise an overexpression of CD46.

Embodiment 144: The method of embodiment 141, wherein the determining comprises a presence or absence of a copy number gain at 1q21.

Embodiment 145: The method of embodiment 141, or 144, wherein the determining comprises using a method selected from the group consisting of fluorescent in-situ hybridization (FISH), gene chip hybridization, multiplexed gene expression analysis, hybridization based digital barcode quantification assays, and lysate based hybridization assays utilizing branched DNA signal amplification.

Embodiment 146: The method of embodiment 141, or 144, wherein the determining comprises using fluorescent in-situ hybridization (FISH).

Embodiment 147: The method of any one of embodiments 141-146, wherein the CD46-targeted therapy comprises a pharmaceutical composition comprising an anti-CD46 antibody.

Embodiment 148: The method of embodiment 147, wherein the anti-CD46 antibody binds to an epitope of CD46 bound by one or more antibodies selected from 3051.1, G12FC3, M6c42b, 4F3YW, M40pr146, UA8, 585II56, 3076, 3051, M49R, RCI-14, 1179-4, 1179-3, T5II-4B.1, T5II-4B.2, RCI-11, RCI-20, CI-11A, CI-14A, S95-2, and mPA7.

Embodiment 149: The method of embodiment 147, wherein the anti-CD46 antibody binds to an epitope of CD46 bound by one or more antibodies selected from SEQ ID NOs: 1, 2, 9, 10, 17, 18, 25, 26, or 33-74.

Embodiment 150: The method of embodiment 147, wherein the anti-CD46 antibody binds to at least a portion of sushi domain 1 of CD46 comprising the amino acid sequence of SEQ ID NO: 75.

Embodiment 151: The method of embodiment 147, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 3, a variable heavy (VH) CDR2 that comprises an amino acid sequence of SEQ ID NO: 4, and a variable heavy (VH) CDR3 that comprises an amino acid sequence of SEQ ID NO: 5.

Embodiment 152: The method of embodiment 147, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 6, a variable light (VL) CDR 2 that comprises an amino acid sequence of SEQ ID NO: 7, and a variable light (VL) CDR 3 that comprises an amino acid sequence of SEQ ID NO: 8.

Embodiment 153: The method of embodiment 147, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 3, a variable heavy (VH) CDR2 that comprises an amino acid sequence of SEQ ID NO: 4, and a variable heavy (VH) CDR3 that comprises an amino acid sequence of SEQ ID NO: 5, and wherein the light chain variable region comprises a variable light (VL) CDR 1 that comprises an amino acid sequence of SEQ ID NO: 6, a variable light (VL) CDR 2 that comprises an amino acid sequence of SEQ ID NO: 7, and a variable light (VL) CDR 3 that comprises an amino acid sequence of SEQ ID NO: 8.

Embodiment 154: The method of embodiment 147, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 11, a variable heavy (VH) CDR2 that comprises an amino acid sequence of SEQ ID NO: 12, and a variable heavy (VH) CDR3 that comprises an amino acid sequence of SEQ ID NO: 13.

Embodiment 155: The method of embodiment 147, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 14, a variable light (VL) CDR 2 that comprises an amino acid sequence of SEQ ID NO: 15, and a variable light (VL) CDR 3 that comprises an amino acid sequence of SEQ ID NO: 16.

Embodiment 156: The method of embodiment 147, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 11, a variable heavy (VH) CDR2 that comprises an amino acid sequence of SEQ ID NO: 12, and a variable heavy (VH) CDR3 that comprises an amino acid sequence of SEQ ID NO: 13, and wherein the light chain variable region comprises a variable light (VL) CDR 1 that comprises an amino acid sequence of SEQ ID NO: 14, a variable light (VL) CDR 2 that comprises an amino acid sequence of SEQ ID NO: 15, and a variable light (VL) CDR 3 that comprises an amino acid sequence of SEQ ID NO: 16.

Embodiment 157: The method of embodiment 147, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 19, a variable heavy (VH) CDR2 that comprises an amino acid sequence of SEQ ID NO: 20, and a variable heavy (VH) CDR3 that comprises an amino acid sequence of SEQ ID NO: 21.

Embodiment 158: The method of embodiment 147, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 22, a variable light (VL) CDR 2 that comprises an amino acid sequence of SEQ ID NO: 23, and a variable light (VL) CDR 3 that comprises an amino acid sequence of SEQ ID NO: 24.

Embodiment 159: The method of embodiment 147, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 19, a variable heavy (VH) CDR2 that comprises an amino acid sequence of SEQ ID NO: 20, and a variable heavy (VH) CDR3 that comprises an amino acid sequence of SEQ ID NO: 21, and wherein the light chain variable region comprises a variable light (VL) CDR 1 that comprises an amino acid sequence of SEQ ID NO: 22, a variable light (VL) CDR 2 that comprises an amino acid sequence of SEQ ID NO: 23, and a variable light (VL) CDR 3 that comprises an amino acid sequence of SEQ ID NO: 24.

Embodiment 160: The method of embodiment 147, wherein the anti-CD46 antibody comprises a heavy chain variable region comprising three complementarity determining regions (CDRs), wherein the heavy chain variable region comprises a variable heavy (VH) CDR1 that comprises an amino acid sequence of SEQ ID NO: 27, a variable heavy (VH) CDR2 that comprises an amino acid sequence of SEQ ID NO: 28, and a variable heavy (VH) CDR3 that comprises an amino acid sequence of SEQ ID NO: 29.

Embodiment 161: The method of embodiment 147, wherein the anti-CD46 antibody comprises a light chain variable region comprising three complementarity determining regions (CDRs), wherein the light chain variable region comprises a variable light (VL) CDR 1 that comprises an amino acid sequence of SEQ ID NO: 30, a variable light (VL) CDR 2 that comprises an amino acid sequence of SEQ ID NO: 31, and a variable light (VL) CDR 3 that comprises an amino acid sequence of SEQ ID NO: 32.

Embodiment 162: The method of embodiment 147, wherein the anti-CD46 antibody comprises a heavy chain variable region comprising three complementarity determining regions (CDRs) and a light chain variable region comprising three CDRs, wherein the heavy chain variable region comprises a variable heavy (VH) CDR1 that comprises an amino acid sequence of SEQ ID NO: 27, a variable heavy (VH) CDR2 that comprises an amino acid sequence of SEQ ID NO: 28, and a variable heavy (VH) CDR3 that comprises an amino acid sequence of SEQ ID NO: 29, and wherein the light chain variable region comprises a variable light (VL) CDR 1 that comprises an amino acid sequence of SEQ ID NO: 30, a variable light (VL) CDR 2 that comprises an amino acid sequence of SEQ ID NO: 31, and a variable light (VL) CDR 3 that comprises an amino acid sequence of SEQ ID NO: 32.

Embodiment 163: The method of any one of the embodiments 147, or 151-162, wherein the anti-CD46 antibody comprises a heavy chain variable region having at least 80%, 85%, 90%, 95%, or 99% sequence identity to SEQ ID NOs: 1, 9, 17 and 25; and a light chain variable region having at least 80%, 85%, 90%, 95%, or 99% sequence identity to SEQ ID NOs: 2, 10, 18, and 26.

Embodiment 164: The method of one of the embodiments 147, or 151-163, wherein the anti-CD46 antibody comprises a heavy chain variable region comprising the amino acid sequence of SEQ ID NO: 1 and a light chain variable region comprising the amino acid sequence of SEQ ID NO: 2.

Embodiment 165: The method of any one of the embodiments 147-164, wherein the anti-CD46 antibody comprises a humanized antibody or binding fragment thereof, a chimeric antibody or binding fragment thereof, a monoclonal antibody or binding fragment thereof, a bispecific antibody or binding fragment thereof, an Fab, an Fab', an F(ab')$_2$, an F(ab')$_3$, an scFv, an sc(Fv)$_2$, a dsFv, a diabody, a minibody, and a nanobody or binding fragments thereof.

Embodiment 166: The method of any one of the embodiments 147-165, wherein the anti-CD46 antibody comprises an Fab, an Fab', an F(ab')$_2$, an F(ab')$_3$, an scFv, an sc(Fv)$_2$, a dsFv, and a diabody or binding fragments thereof.

Embodiment 167: The method of any one of the embodiments 147-165, wherein the anti-CD46 antibody comprises a full-length immunoglobulin.

Embodiment 168: The method of any one of the embodiments 147-165, wherein the anti-CD46 antibody comprises a bispecific antibody or binding fragment thereof.

Embodiment 169: The method of embodiment 141-168, wherein the subject is administered a therapeutically effective amount of a pharmaceutical composition comprising an anti-CD46 antibody.

Embodiment 170: The method of embodiment 169, wherein the anti-CD46 antibody is formulated for parenteral administration.

Embodiment 171: The method of embodiment 169, or 170, wherein the anti-CD46 antibody is administered to the subject as an injection.

Embodiment 172: The method of embodiment 169, or 170, wherein the anti-CD46 antibody is administered to the subject as an infusion.

Embodiment 173: The method of any one of the embodiments 141-172, wherein the subject is a human.

Embodiment 174: The method of any one of the embodiments 141-172, wherein the subject is a non-human mammal.

BRIEF DESCRIPTION OF THE DRAWINGS

The patent or application file contains at least one drawing executed in color. Copies of this patent or patent application publication with color drawing(s) will be provided to the Office upon request and payment of necessary fee.

An understanding of certain features and advantages of the present invention will be obtained by reference to the following detailed description that sets forth illustrative embodiments, in which the principles of the invention are utilized, and the accompanying drawings of which.

Panel B) Dose response for CD46-ADC inhibition of viability of MM cells compared to HS5 and BM61 bone marrow stromal cells after 96-hour incubation (n=3). NR: EC50 not reached due to lack of killing at the highest concentration tested. Panel C) Lack of effect of nonbinding control ADC until approximately 100 nM (n=3). Panel D) Annexin V and PI staining of MM cell line INA-6 for 0-10 nM CD46-ADC, with apoptosis and death by 48 hours (representative data, n=3). Panel E) Sensitivity of MM1.S cell line to CD46-ADC is increased in the presence of HS5, BM61 or HS27A bone marrow stromal cells. EC50 was 2.25 nM on MM1.S alone and 0.77 nM, 0.92 nM, and 1.05 nM for MM1.S in the presence of HS5, HS27A, and BM61, respectively (data represent mean±SEM, n=3).

Figure 7:
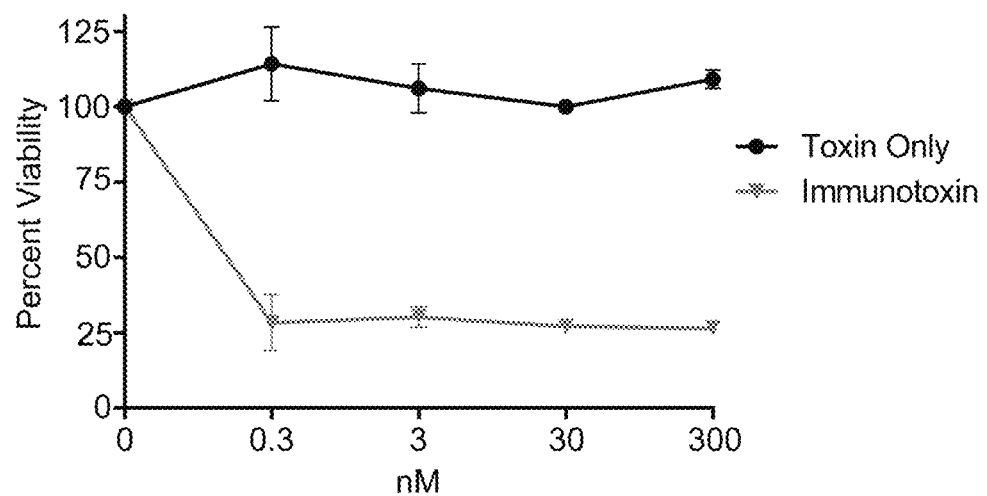

FIG. 7 shows potent and selective killing of the RPMI8226 myeloma cell line by anti-CD46 immunotoxin (saporin).

Figure 8:
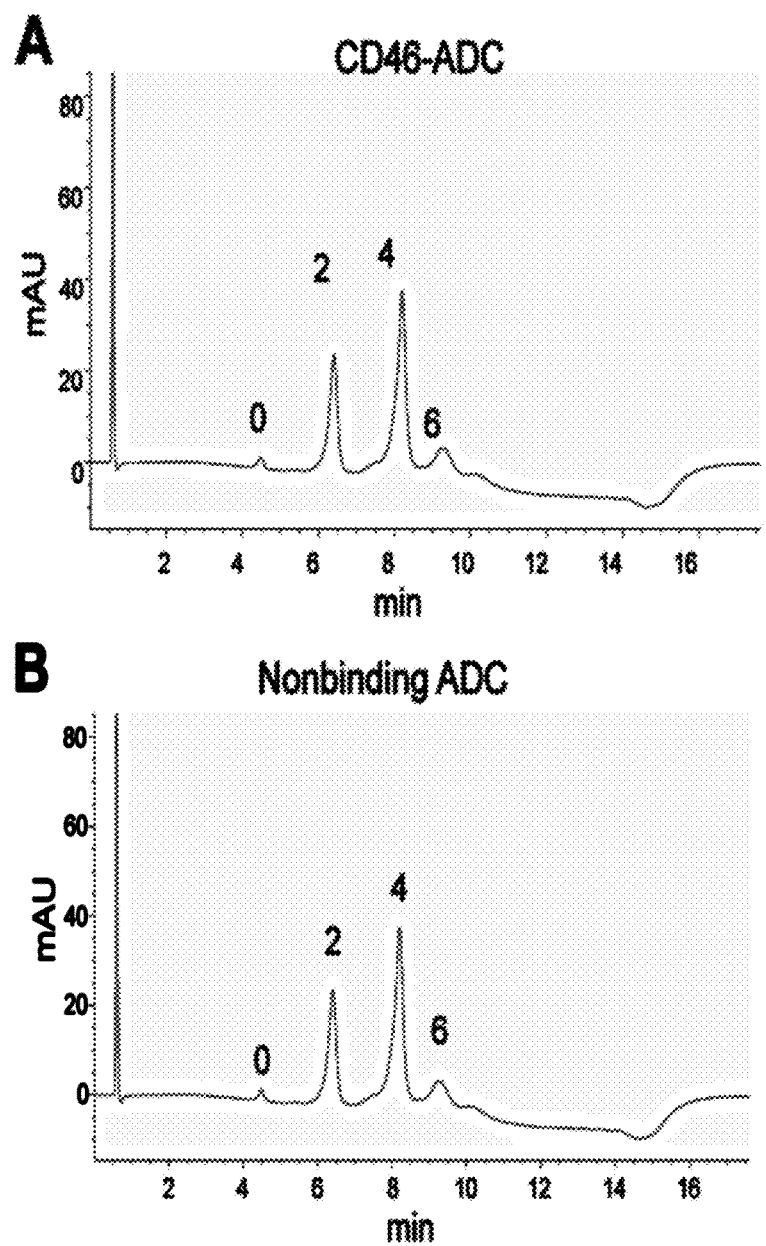

FIG. 8, panels A and B, illustrates HPLC analysis with hydrophobic interaction chromatography for antibody-mcvcpab-MMAF conjugates.

Figure 9:
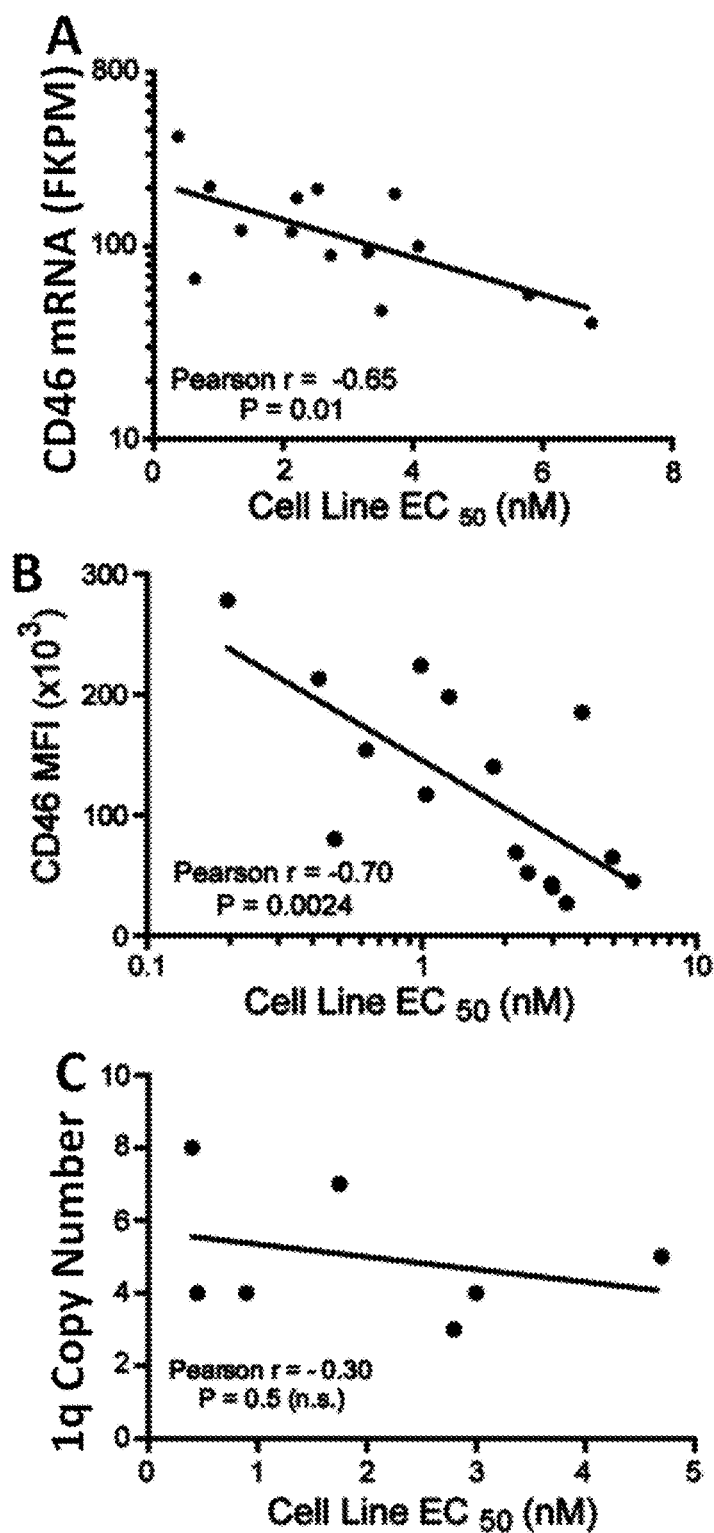

FIG. 9, panels A-C, shows inverse correlation of CD46 transcript and cell surface expression with EC50 values of CD46-ADC by in vitro cytotoxicity assays.

Figure 10:
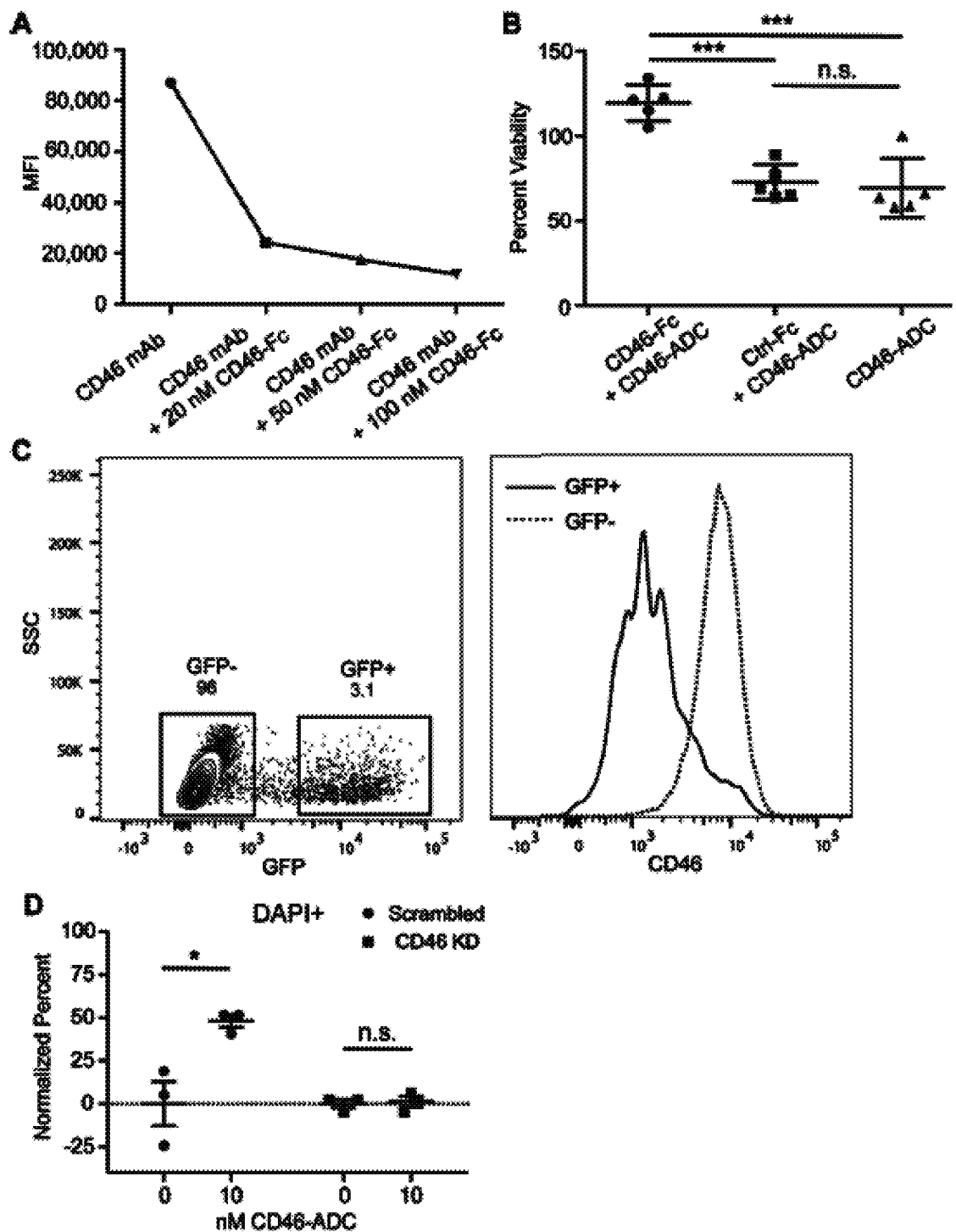

FIG. 10, panels A-D, shows CD46-ADC cytotoxicity is dependent on interaction with cell surface CD46.

Figure 11:
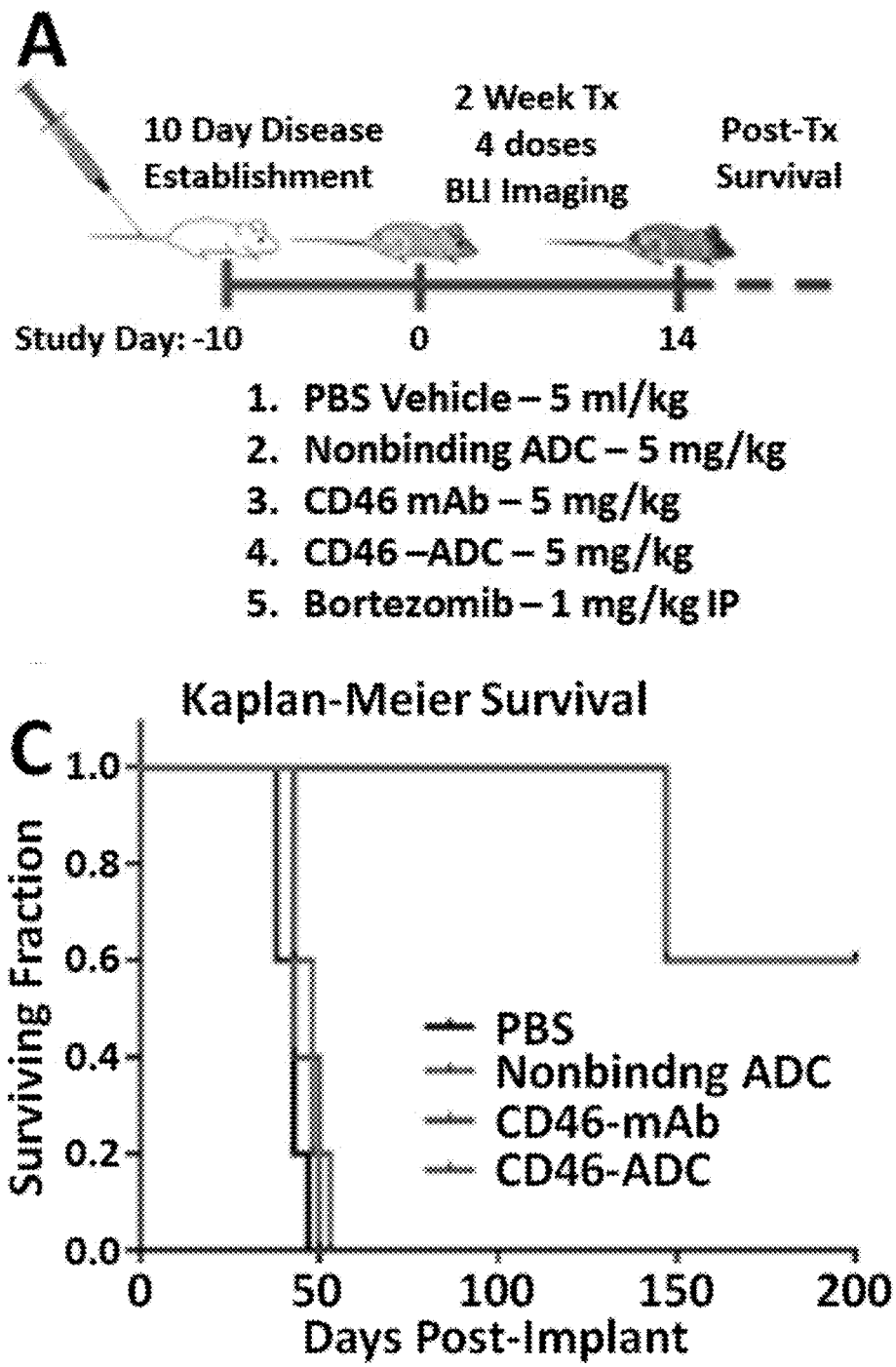

FIG. 11, panels A-C, illustrates in vivo CD46-ADC anti-myeloma activity in the RPMI8226-Luc disseminated xenograft model. Panel A) Study treatment scheme. RPMI8226-Luc cells were i.v. injected and established for 10 days. Starting on the 10th day (treatment day 1) a total of 4 injections of PBS, control nonbinding ADC (5 mg/kg), naked CD46 antibody (5 mg/kg), CD46-ADC (5 mg/kg) or bortezomib (1 mg/kg) were given twice per week (n=5 mice/group). Panel B) Disease was monitored by BLI (top views—dorsal, bottom views—ventral). BLI measurement in photons/sec/cm2/steradian (p/sec/cm2/sr) was translated to color to indicate disease activity in the mice by legend shown at far right. Tx—treatment, mAb—naked antibody. Panel C) Kaplan-Meier survival curves of NSG xenografts transplanted with RPMI-Luc and treated with CD46-ADC or controls.

Figure 12:
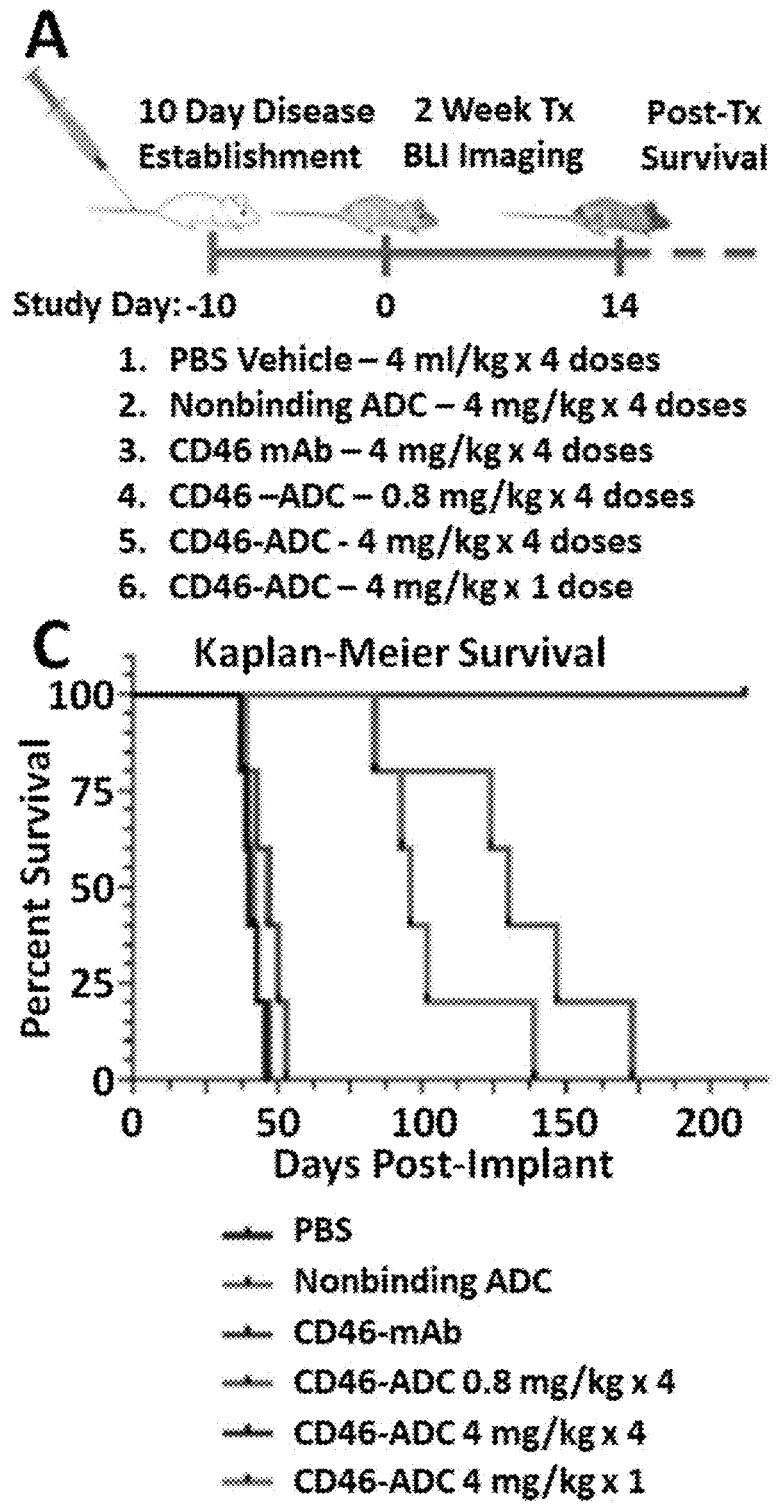

FIG. 12, panels A-C, illustrates dose and schedule-dependent in vivo activity of CD46-ADC in a disseminated MM xenograft model with MM1.S cell line. Panel A) Study treatment scheme. MM1.S-Luc cells were injected and established for 10 days. Starting on day 11 (treatment day 1), a total of 4 injections were given twice a week at the concentrations shown for all groups, except for the single dose group. For each group, n=5 mice/group. Panel B) BLI rapidly increased in negative control groups, but decreased to undetectable levels with all CD46-ADC treatment regimens (top views—dorsal, bottom views—ventral). Relapse of disease activity was observed progressively at single dose 4 mg/kg and low dose 0.8 mg/kg groups. No detectable BLI signal and no relapse post-treatment was observed for the 4 mg/kg, 4 dose schedule, suggesting complete elimination of MM1.S xenografts in vivo. BLI in photons/sec/cm2/steradian (p/sec/cm2/sr) was translated to color to indicate disease activity by legend shown at far right. Tx—treatment, mAb—naked antibody. Panel C) Kaplan-Meier survival curves of NSG xenografts transplanted with MM1.S-Luc and treated with varying dose levels of CD46-ADC.

Figure 13:
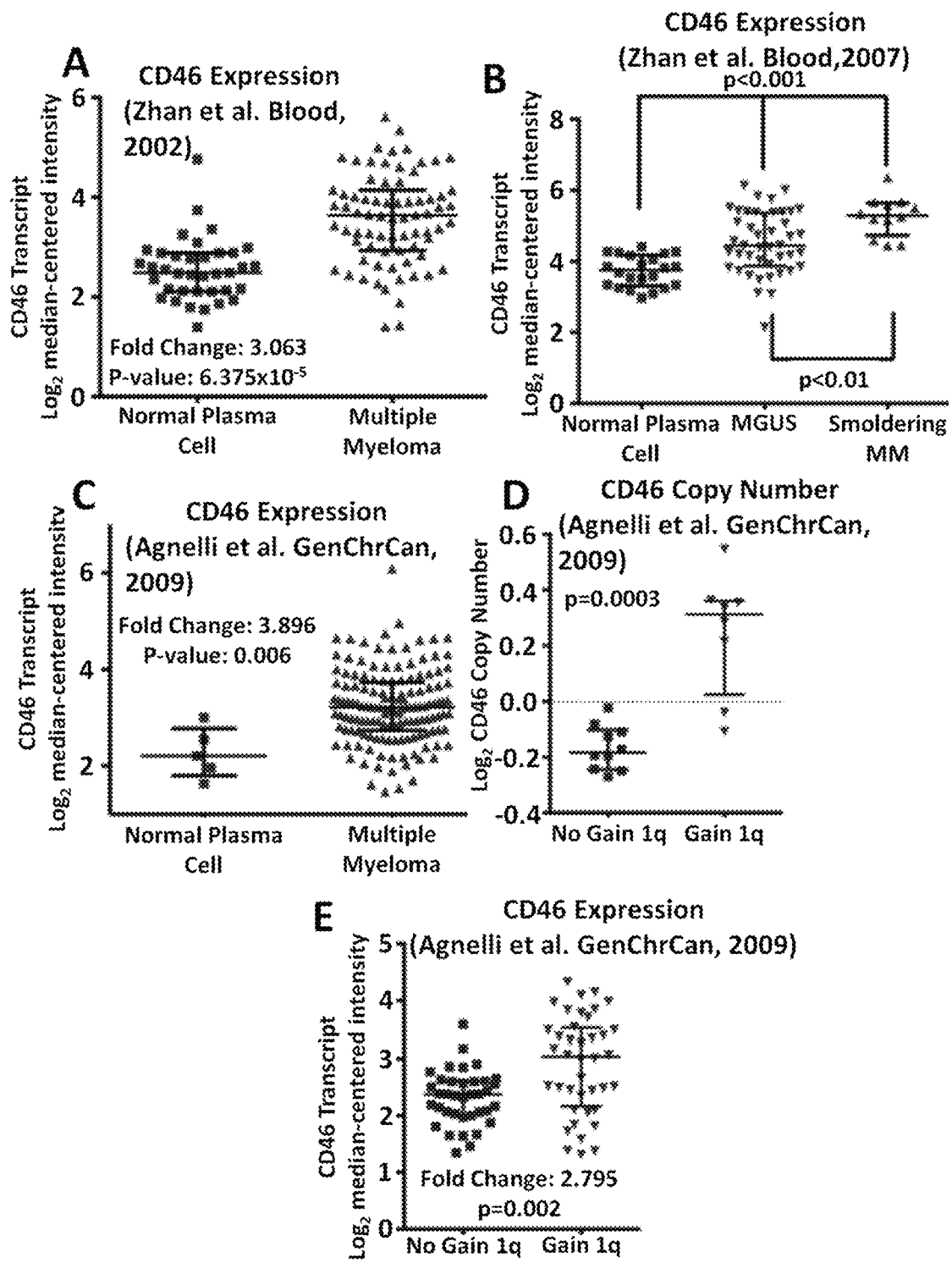

FIG. 13, panels A-E, shows increases in CD46 gene expression are associated with MM development and FISH 1q gain.

Figure 14:
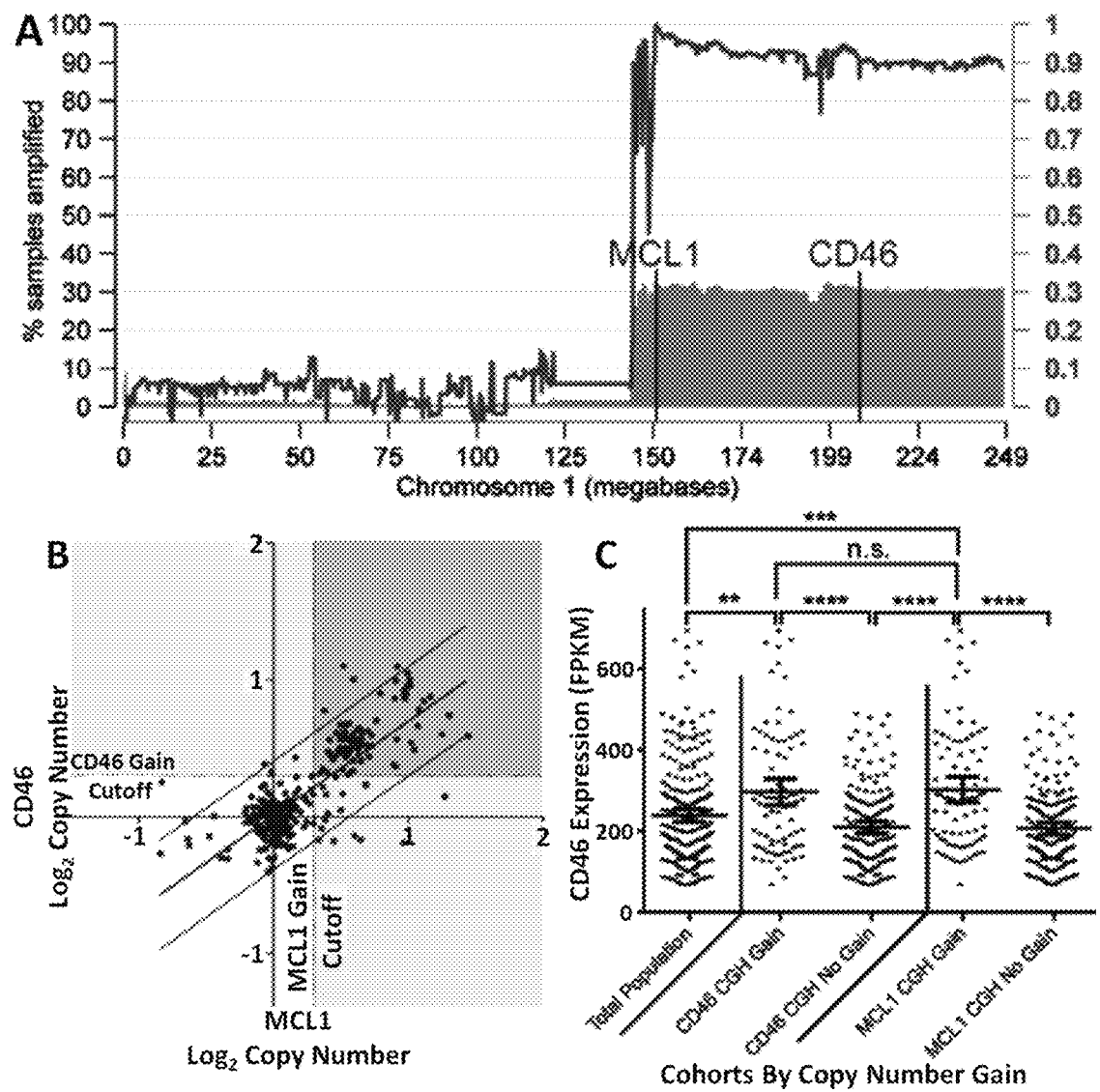

FIG. 14, panels A-C, shows that CD46 locus is frequently co-amplified with 1q21 and copy gain for either MCL1 or CD46 identifies patients with high CD46 expression. Panel A)~30% of newly diagnosed patients demonstrate 1q21 copy gain overlapping the MCL1 locus by array CGH, defined as log 2 copy number>0.3, and a similar proportion demonstrate amplification along the 1q arm, including CD46 (grey shaded histogram; left axis). High frequency of co-amplification along the 1q arm with MCL1 amplification is shown by the purple line and quantified on the right axis (n=322 patients). Panel B) Dot-plot of log 2 CGH values in patient samples indicates copy number for CD46 and MCL1 loci are highly correlated and cluster in regular copy number intervals (n=322 patients). Panel C) Mean CD46 transcript expression values (quantified as FPKM) for CD46 or MCL1 copy-amplified cohorts, defined by >0.3 log 2 CGH value, versus non-amplified cohorts indicate high CD46 expression in MCL1 or CD46 amplified patient samples, compared to total population or samples without copy gain (n=260 patients). Data represent mean±95% CI. One-way ANOVA with Tukey's multiple comparison correction, p<0.01, *p<0.001, ****p<0.0001.

Figure 15:
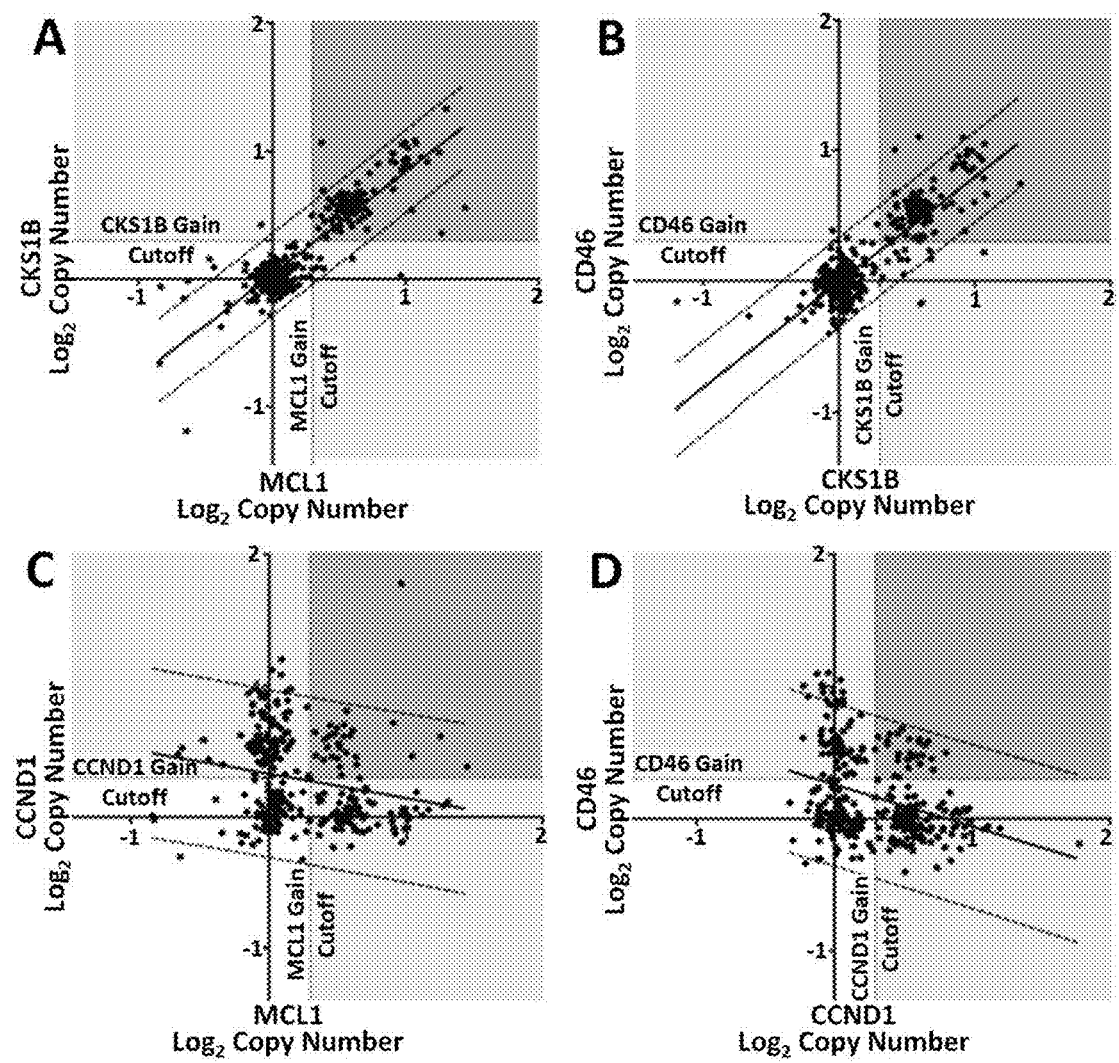

FIG. 15, panels A-D, shows copy number correlation analysis for CD46, CKS1B, MCL1, and the control CCND1.

Figure 16:
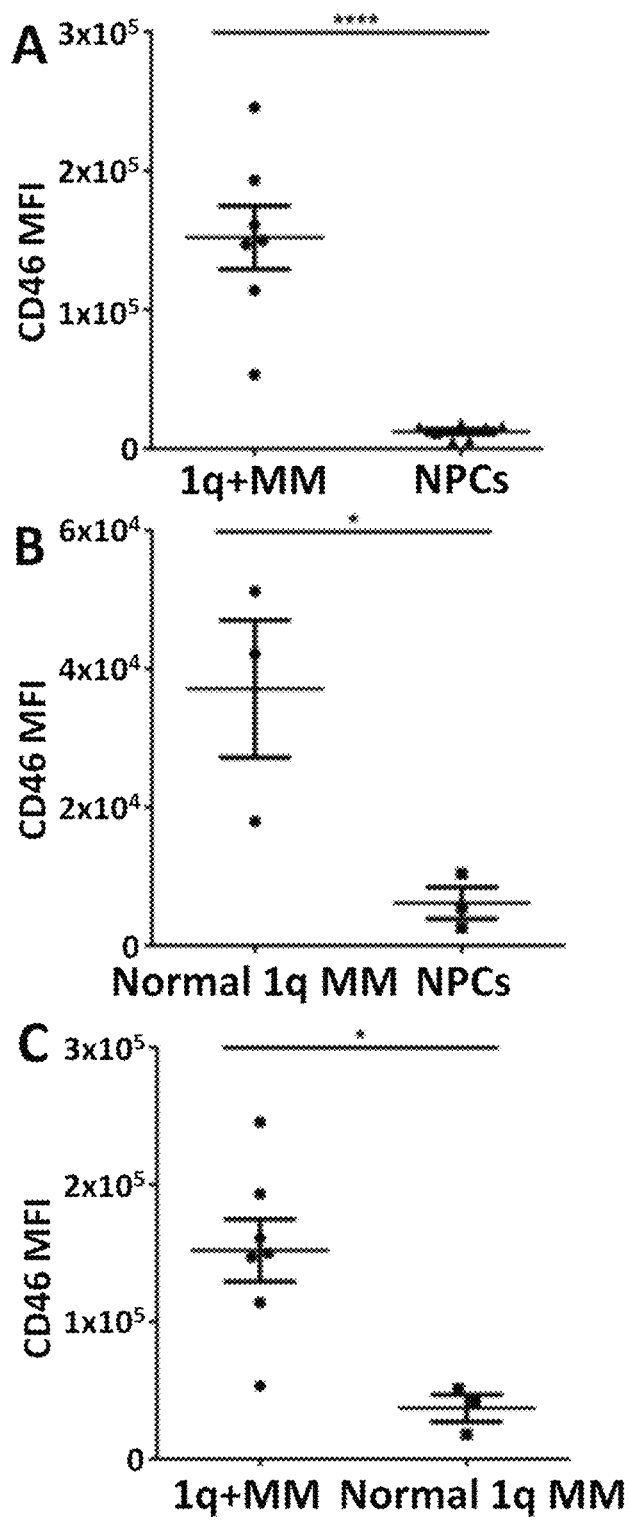

FIG. 16, panels A-C, shows evaluation of cell surface CD46 expression in primary MM cells from patients with amp1q21 and normal 1q.

Figure 17:
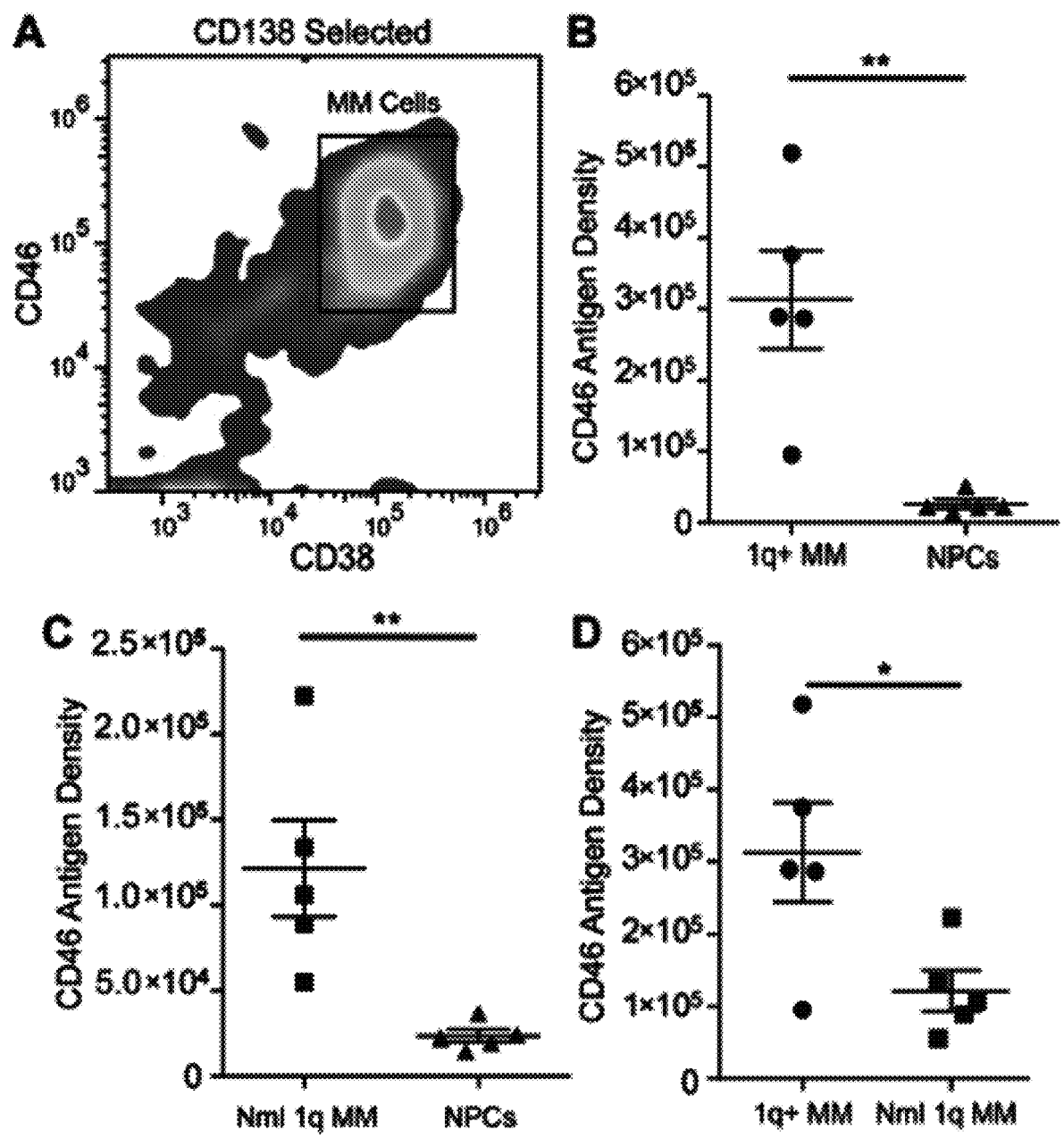

FIG. 17, panels A-G, shows that CD46 is overexpressed on cell surface of primary MM patient cells and further amplified in patients with amp1q21 compared to normal 1q. Panel A) FACS plot showing that CD46 surface expression correlates with CD38 in CD138 selected cells to identify the MM population by FACS (representative data, n=25). Panel B) Quantitative FACS results for CD46 antigen density from MM vs. NPC from patients with normal (nml) 1q (n=5). Panel C) Quantitative FACS results for CD46 antigen density from MM vs. NPC from patients with amp1q21 (1q+, n=5). Panel D) CD46 antigen density is further increased in amp1q2l patients (n=5) compared to patients with normal 1q (n=5). Panel E) CD46 antigen density on various BM normal cell populations compared to MM cells from 7 additional patients. Panel F) CD46 antigen density on various BM cell populations from 3 normal donors. Panel G) CD46 antigen density on various peripheral blood cell populations from 3 normal donors. Data represent mean+/− SEM. Two-tailed t-test, *p<0.05, **p<0.01.

Figure 18:
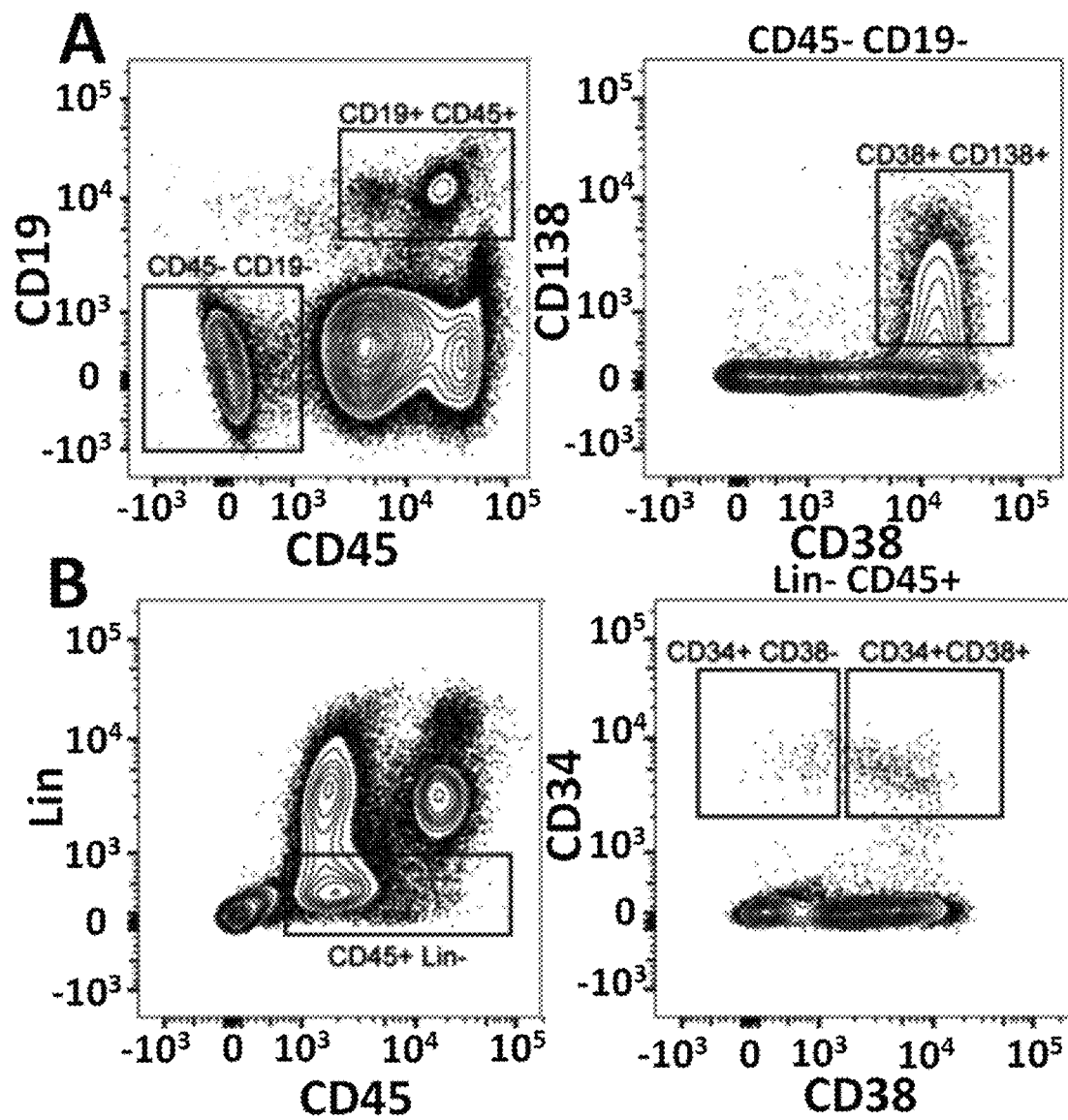

FIG. 18, panels A-E, shows representative examples of FACS analysis of CD46 of various cell populations in myeloma patient bone marrow aspirates.

Figure 19:
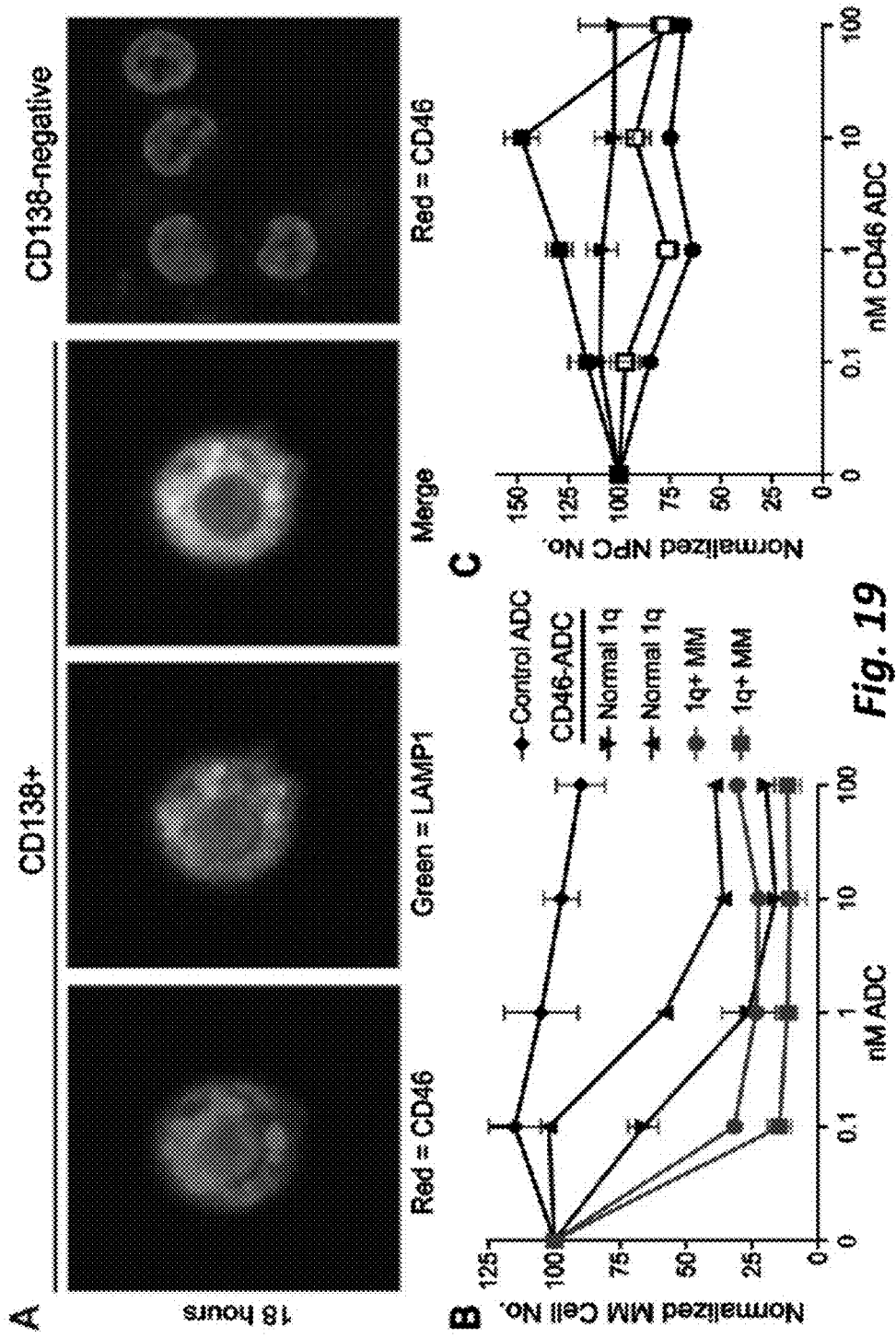

FIG. 19, panels A-C, shows ex vivo evaluation of CD46-ADC in patient sample MM cells. Panel A) Internalization of CD46 antibody (red) into MM patient cells ex vivo. CD138 positively selected cells from a patient with MM were incubated with CD46 antibody for 18 hours and co-stained with anti-LAMP1 antibody (green) and Hoechst dye (blue). Representative cell illustrates the intracellular, localization of CD46 antibody, partially co-localizing with the late lysosomal marker LAMP1 (Left). CD138-negative cells were treated in the same fashion and showed minimal binding of CD46 antibody without discernable internalization (Right). Images were taken using digital confocal microscope Fluoview (Olympus) at 60× magnification. Panel B) CD46-ADC depletes the number of CD138-positive, CD38-positive MM cells more potently in patients with amp1q2l. Mean values with SEM are shown for CD46-ADC treatment of 2 patient samples with amp1q21 (red lines) and 2 patient samples with normal 1q21 (blue lines), compared to cells treated with nonbinding control ADC (black). Panel C) CD46-ADC does not affect the number of NPCs up to a concentration of 100 nM (n=4) (data represent mean+/−SEM).

Figure 20:
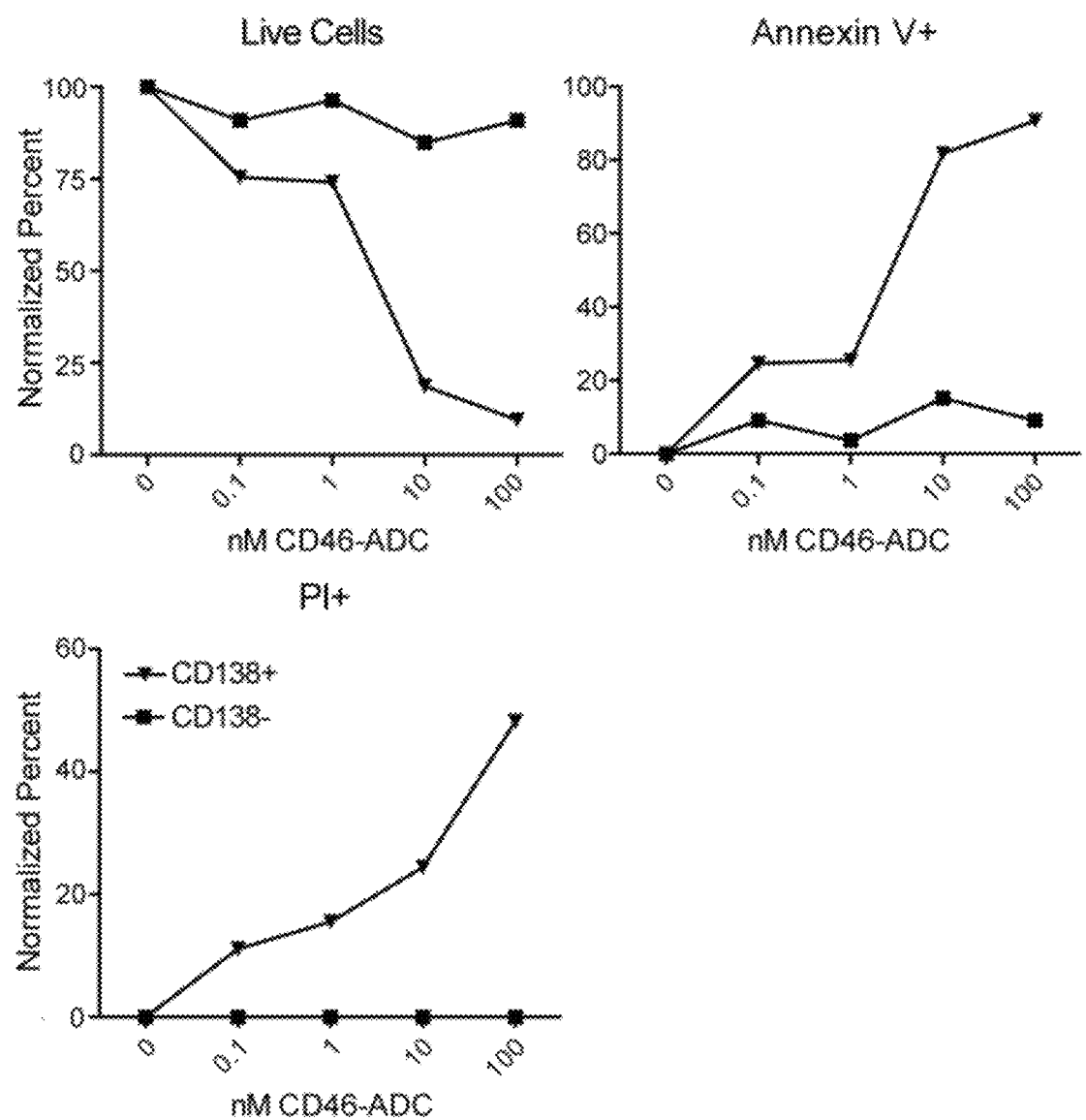

FIG. 20 shows effect of CD46-ADC on myeloma cells and normal bone marrow mononuclear cells at concentrations up to 100 nM.

Figure 21:
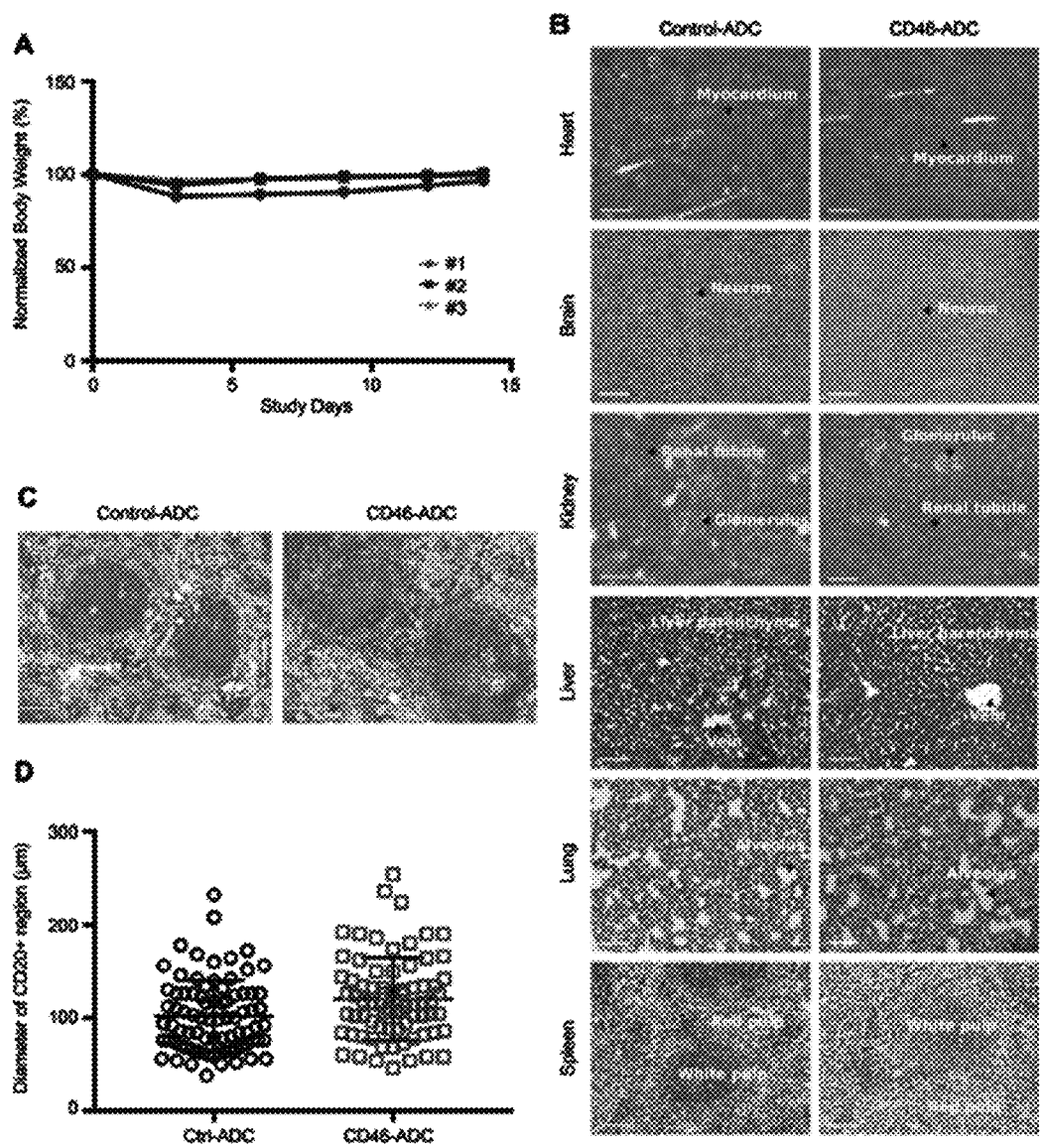

FIG. 21, panels A-D, shows evaluation of tolerability of CD46-ADC in transgenic mice expressing human CD46. Three mice were treated with CD46-ADC or isotype (non-binding) control ADC at 6 mg/kg i.v. and monitored for 14 days. Panel A) Body weight analysis over the monitoring period showed no weight loss greater than 12% following CD46-ADC injection. Panel B) Histologic analysis at the time of experiment discontinuation. Images were taken by a Keyence digital microscope at 20× magnification. Histological features (pointed by arrows) are indicated on the graph. No notable difference was observed between CD46-ADC and control ADC treated samples. Scale bar, 100 μm. Panel C) Immunohistochemistry analysis of CD20 positive region in CD46-ADC and control ADC40 treated spleens. Scale bar (lower left corner), 100 μm. Panel D) Diameters of CD20-positive regions in CD46-ADC and control ADC-treated spleens (n=74 for CD46-ADC-treated and 81 for control ADC-treated, respectively). No significant difference was observed (two-tailed t-test, p>0.05).

Figure 22:
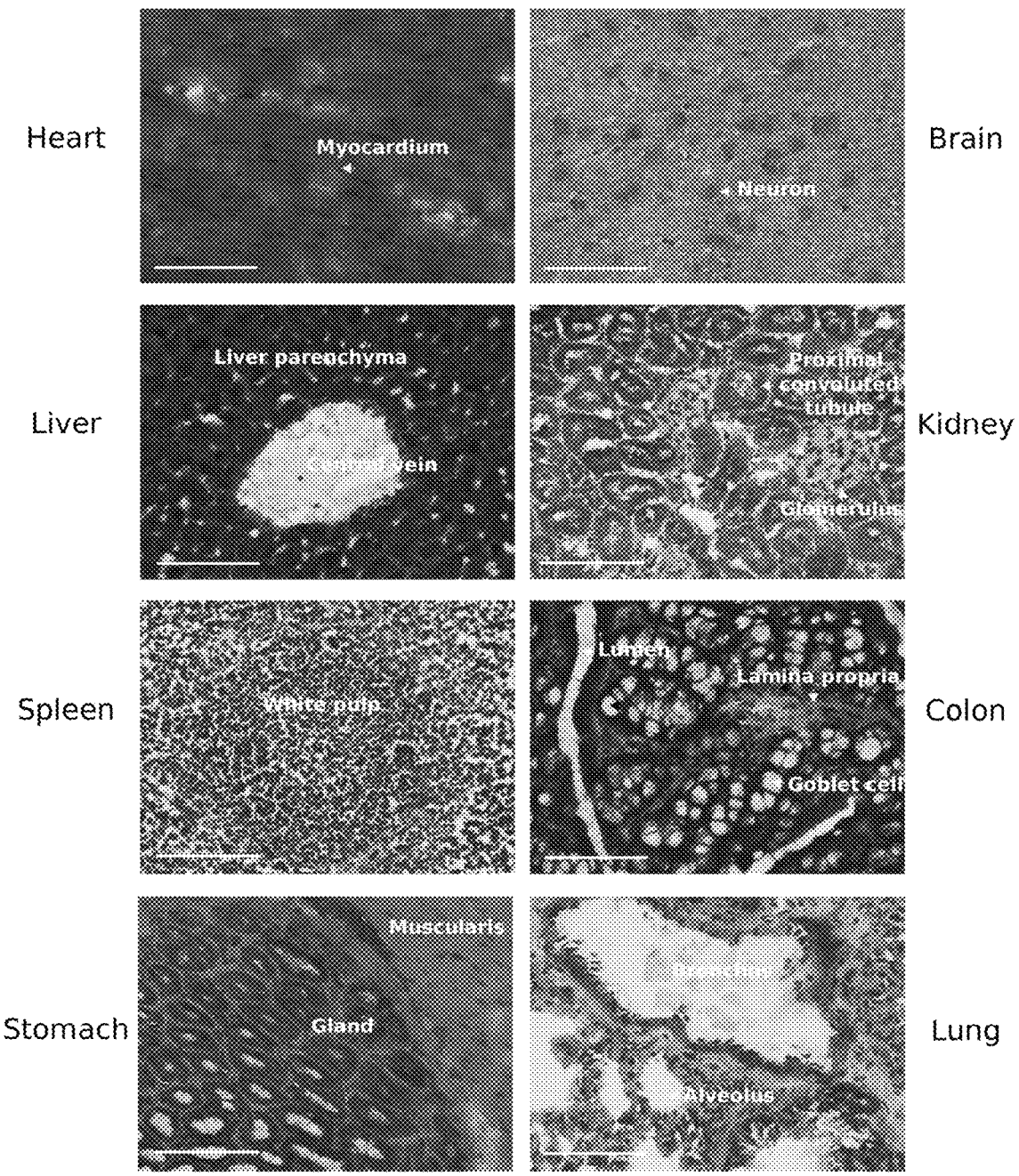

FIG. 22 shows histologic analysis of tissues from CD46-ADC-treated transgenic mice expressing human CD46.

DETAILED DESCRIPTION OF THE DISCLOSURE

In some embodiments, gain of chromosome 1q copy is a high-risk cytogenetic biomarker that has been linked to shorter progression-free survival and poor treatment response. In some instances, 1q21 is the minimal amplifying region (MAR) that is frequently amplified. In some cases, patients with copy number gain of chromosome 1q (e.g., 1q21 gain) cease to respond to approved agents, develop treatment-refractory disease, and have shortened overall survival.

It was discovered, inter alia, that in some embodiments, the presence of 1q21 gain is associated with an elevated expression (e.g., overexpression) of CD46. CD46, also known as CD46 complement regulatory protein, cluster of differentiation 46 and membrane cofactor protein, is an inhibitory complement receptor. CD46 is located in chromosome 1q32.2. Although in some instances, CD46 is observed to be overexpressed in tumor cells; however, in some cases the presence of 1q21 gain further amplifies the expression of CD46.

In certain embodiments, methods are provided for treating a subject having a cancer characterized by a modification at chromosome 1q21. In certain embodiments the method(s) comprise administering to a subject identified to have a modification at chromosome 1q21 a therapeutically effective amount of a CD46-targeted therapy. In some cases, the modification at 1q21 is an amplification of 1q21 (e.g., a copy number gain of 1q21). In some instances, the amplification of 1q21 comprises a gain of at least 1, 2, 3, 4, or more copy numbers of 1q21. In some cases, the amplification of 1q21 comprises a gain of at least 1 or more copy numbers of 1q21. In some cases, the amplification of 1q21 comprises a gain of at least 2 or more copy numbers of 1q21. In some cases, the amplification of 1q21 comprises a gain of at least 3 or more copy numbers of 1q21. In some cases, the amplification of 1q21 comprises a gain of at least 4 or more copy numbers of 1q21.

Myeloid Cell Leukemia-1, or induced myeloid leukemia cell differentiation protein Mcl-1, is a member of the Bcl-2 family of proteins and is located at 1q21. Alternative splicing results in at least three isoforms of MCL1, in which isoform 1 enhances cell survival by inhibiting apoptosis while isoforms 2 and 3 promote apoptosis. In some embodiments, amplification of 1q21 further leads to an amplification of MCL1. In certain embodiments, MCL1 is co-amplified with CD46.

In some instances, a mean CD46 antigen density on cancer cells is observed to be at least 200,000, at least 250,000, at least 300,000, at least 350,000 or more. In some cases, a mean CD46 antigen density on cancer cells is observed to be about 300,000 or higher, about 310,000 or higher, or about 320,000 or higher.

In some cases, the CD46-targeted therapy comprises administration of an anti-CD46 antibody, administration of an oncolytic virus that targets CD46, administration of an engineered effector cell (e.g., targeted to CD46), and the like. In some instances, the CD46-targeted therapy comprises administration of an anti-CD46 antibody. In some instances, the CD46-targeted therapy comprises administration of an oncolytic virus (e.g., an oncolytic measles virus) that targets CD46. In some cases, the CD46-targeted therapy comprises a administration of a modified effector cell (e.g., CAR-T or CAR-NK). In some cases, the CD46-targeted therapy comprises a administration of a pharmaceutical composition comprising an anti-CD46 antibody.

In some embodiments, a cancer characterized by a modification at chromosome location 1q21 comprises multiple myeloma, breast cancer or liver cancer. In some cases, a cancer characterized by a modification at chromosome location 1q21 comprises a relapsed or refractory cancer. In certain cases, a cancer characterized by a modification at chromosome location 1q21 comprises a metastatic cancer.

In some instances, a cancer characterized by a modification at chromosome location 1q21 is multiple myeloma. Multiple myeloma (MM) or plasma cell myeloma is a cancer of plasma cells, a type of white blood cells. In some cases, multiple myeloma is further classified into indolent multiple myeloma, symptomatic multiple myeloma, solitary plasmacytoma of the bone, extramedullary plasmacytoma, light chain myeloma, non-secretory myeloma, IgD myeloma, and IgE myeloma. In some instances, multiple myeloma is a relapsed or refractory multiple myeloma.

In some embodiments, methods are provided for treating a subject having multiple myeloma characterized by a modification at chromosome location 1q21, in which the method(s) comprise administering to the subject identified to have a modification at chromosome location 1q21 a therapeutically effective amount of a CD46-targeted therapy (e.g., an anti-CD46 antibody-based therapy). In some cases, the multiple myeloma is further characterized with an amplification of CD46 mRNA, leading to an elevated expression of CD46. In some cases, the multiple myeloma is a relapsed or refractory multiple myeloma.

In some embodiments, a cancer characterized by a modification at chromosome location 1q21 is breast cancer. In some instances, breast cancer is further classified into ductal carcinoma in situ, invasive (or infiltrating) ductal carcinoma, invasive (or infiltrating) lobular carcinoma, inflammatory breast cancer, Paget disease of the nipple, phyllodes tumor, or angiosarcoma. In some cases, a breast cancer is a triple negative breast cancer. In some cases, a breast cancer is a metastatic breast cancer. In some cases, a breast cancer is a relapsed or refractory breast cancer. In additional cases, a breast cancer comprises an intrinsic and/or an acquired resistance to HER2-targeted therapeutic agents.

In some embodiments, methods are provided for treating a subject having breast cancer characterized by a modification at chromosome location 1q21, in which the method(s) comprise administering to the subject identified to have a modification at chromosome location 1q21 a therapeutically effective amount of a CD46-targeted therapy (e.g., an anti-CD46 antibody-based therapy). In some cases, the breast cancer is further characterized with an amplification of CD46 mRNA, leading to an elevated expression of CD46. In some cases, the breast cancer is a relapsed or refractory breast cancer. In certain cases, the breast cancer is a metastatic breast cancer.

In some embodiments, a cancer characterized by a modification at chromosome location 1q21 is liver cancer. In some cases, liver cancer is further classified into hepatocellular carcinoma (HCC), fibrolamellar HCC, cholangiocarcinoma (bile duct cancer), angiosarcoma or secondary liver cancer (or liver metastasis). In some cases, the liver cancer is a relapsed or refractory liver cancer.

In some embodiments, methods are provided for treating a subject having liver cancer characterized by a modification at chromosome location 1q21, in which the method(s) comprise administering to the subject identified to have a modification at chromosome location 1q21 a therapeutically effective amount of a CD46-targeted therapy (e.g., an anti-CD46 antibody-based therapy). In some cases, the liver cancer is further characterized with an amplification of CD46 mRNA, leading to an elevated expression of CD46. In some cases, the liver cancer is a relapsed or refractory liver cancer. In other cases, the liver cancer is a metastatic liver cancer.

Anti-CD46 Antibodies

In various embodiments, an anti-CD46 antibody used in the methods described herein recognizes and binds (e.g., specifically binds) to an epitope of CD46. In some instances, an anti-CD46 antibody comprises a human antibody or binding fragment thereof, a humanized antibody or a binding fragment thereof, a murine antibody or a binding fragment thereof, a chimeric antibody or a binding fragment thereof, a monoclonal antibody or a binding fragment thereof, a monovalent Fab', a divalent Fab2, an F(ab)'3 fragments, a single-chain variable fragment (scFv), a bis-scFv, an (scFv)$_2$, a diabody, a minibody, a nanobody, a triabody, a tetrabody, a disulfide stabilized Fv protein (dsFv), a single-domain antibody (sdAb), an Ig NAR, a camelid antibody or a binding fragment thereof, or a chemically modified derivative thereof. In some instances, an anti-CD46 antibody comprises a monoclonal antibody or a binding fragment thereof, a humanized antibody or a binding fragment thereof, or a chimeric antibody or a binding fragment thereof. In some cases, an anti-CD46 antibody comprises an Fab, an Fab', an F(ab')$_2$, an F(ab')$_3$, an scFv, an sc(Fv)$_2$, a dsFv, a diabody, a minibody, and a nanobody or binding fragments thereof. In some embodiments, the anti-CD46 antibody comprises a bispecific antibody or binding fragment thereof. In some embodiments, the bispecific antibody or binding fragment thereof further binds to a cancer marker that is different from CD46. In certain embodiments, the bispecific antibody or binding fragment thereof further binds to an effector cell.

In some embodiments, the anti-CD46 antibody binds to an epitope of CD46 bound by one or more antibodies selected from 3051.1, G12FC3, M6c42b, 4F3YW, M40pr146, UA8, 585II56, 3076, 3051, M49R, RCI-14, II79-4, II79-3, T5II-4B.1, T5II-4B.2, RCI-11, RCI-20, CI-1 A, CI-14A, and S95-2 (which are described in PCT/US2008/076704, which is incorporated herein by reference for the antibodies and antibody sequences described therein).

In some embodiments, the anti-CD46 antibody binds to an epitope of CD46 bound by mPA7, produced by a host cell with a deposit number of ATCC No. PTA-3706 or progeny thereof (which is described in US20070128202).

In some embodiments, an anti-CD46 antibody binds to an epitope of CD46 bound by one or more antibodies selected from SEQ ID NOs: 1, 2, 9, 10, 17, 18, 25, 26 or 33-74 (Tables 1 and 2). In some cases, the anti-CD46 antibody binds to at least a portion of sushi domain 1 of CD46 comprising the amino acid sequence KPYYEIGERVDYKCKK(GYFYIPPLATHTICDR (SEQ ID NO: 75). In other cases, an anti-CD46 antibody binds to an epitope of CD46 bound by one or more antibodies selected from SEQ ID NOs: 1, 2, 9, 10, 17, 18, 25 or 26 (Table 1). In additional cases, an anti-CD46 antibody binds to an epitope of CD46 bound by one or more antibodies selected from SEQ ID NOs: 33-74 (Table 2).

TABLE 1

Antibody and/or CDR sequences.

| Identifier | Sequence | SEQ ID NO: |
|---|---|---|
| YS5, VH | QVQLVQSGGGVVQPGRSLRLACAASGLTVNNYAMHWVRQA PGKGLEWVAVISYDGNNKYYADSVKGRFTISRDNSKNTLYLQ MNSLRAEDTAVYYCAKGGGYFDLWGRGTLVTVSS | 1 |
| YS5, VL | QSVLTQPPSVSGAPGQRVTISCTGSSSNIGAGYDVHWYQQLPG TAPKLLIYGNNNRPSGVPDRFSGSKSGTSASLAITGLQAEDEA DYYCSSYTSGTWLFGGGTKLTVL | 2 |
| YS5, VH CDR1 | GLTVNNYA | 3 |
| YS5, VH CDR2 | ISYDGNNK | 4 |
| YS5, VH CDR3 | AKGGGYFDL | 5 |
| YS5, VL CDR1 | SSNIGAGYD | 6 |
| YS5, VL CDR2 | GNN | 7 |
| YS5, VL CDR3 | SSYTSGTWL | 8 |

TABLE 1-continued

Antibody and/or CDR sequences.

| Identifier | Sequence | SEQ ID NO: |
|---|---|---|
| YS12, VH | QVQLVESGGGVVQPGRSLRLSCAASGFTFSTYGMHWVRQAP GKGLEWLSFISYDGDEKYYADSVKGRFTISRDNSKNTLYLQ MNSLRAEDTAVYWCAKASGYGMGILDYWGQGTLVTVSS | 9 |
| YS12, VL | SSELTQDPAVSVALGQTVRITCQGDSLRSYYVSWFQQKPGQA PVFVMYGQNNRPSGISERFSGSSSGNTASLIITGAQAEDEAD YYCHSRDSSGTHLRVFGGGTKLTVL | 10 |
| YS12, VH CDR1 | GFTFSTYG | 11 |
| YS12, VH CDR2 | FISYDGDEK | 12 |
| YS12, VH CDR3 | AKASGYGMGILDY | 13 |
| YS12, VL CDR1 | SLRSYY | 14 |
| YS12, VL CDR2 | GQN | 15 |
| YS12, VL CDR3 | HSRDSSGTHLRV | 16 |
| YS5vID, VH | QVQLVQSGGGVVQPGRSLRLACAASGFTVNNYAMHWVRQA PGKGLEWVAVISYDGNNKYYADSVKGRFTISRDNSKNTLY LQMNSLRAEDTAVYYCAKGGGYFDLWGRGTLVTVSS | 17 |
| YS5vID, VL | QSVLTQPPSVSGAPGQRVTISCTGSSSNIGAGYDVHWYQQLPG TAPKLLIYGDNNRPSGVPDRFSGSKSGTSASLAITGLQAEDEA DYYCSSYTSGTWLFGGGTKLTVL | 18 |
| YS5vID, VH CDR1 | GFTVNNYA | 19 |
| YS5vID, VH CDR2 | ISYDGNNK | 20 |
| YS5vID, VH CDR3 | AKGGGYFDL | 21 |
| YS5vID, VL CDR1 | SSNIGAGYD | 22 |
| YS5vID, VL CDR2 | GDN | 23 |
| YS5vID, VL CDR3 | SSYTSGTWL | 24 |
| SB1HGNY, VH | QVQLQQSGGGVVQPGRSLRLSCAASGFTFSSYAMHWVRQAP GKGLEWVAFIRSDGSKKYYADSVKGRFTISRDNSKNTLYLQ MNSLRAEDTAVYYCARHGNYFDSWGQGTLVTVSS | 25 |
| SB1HGNY, VL | DIQMTQSPSFLSASVGDRVTITCRASQGISSYLAWYQQKPGKA PKLLIYAASTLQSGVPSSFSGSGSGTEFTLTISSLQPEDFATY YCQQLASYPLTFGGGTKVDIK | 26 |
| SB1HGNY, VH CDR1 | GFTFSSYA | 27 |
| SB1HGNY, VH CDR2 | IRSDGSKK | 28 |
| SB1HGNY, VH CDR3 | ARHGNYFDS | 29 |
| SB1HGNY, VL CDR1 | QGISSY | 30 |
| SB1HGNY, VL CDR2 | AAS | 31 |
| SB1HGNY, VL CDR3 | QQLASYPLT | 32 |

TABLE 2

Antibody sequences.

| Identifier | Sequence | SEQ ID NO: |
|---|---|---|
| YS5F, VH | QVQLVQSGGGVVQPGRSLRLACAASGFTVNNYAMHWVR QAPGKGLEWVAVISYDGNNKYYADSVKGRFTISRDNSKN TLYLQMNSLRAEDTAVYYCAKGGGYFDLWGRGTLVTVSS | 33 |
| YS5F, VL | QSVLTQPPSVSGAPGQRVTISCTGSSSNIGAGYDVHWYQQ LPGTAPKLLIYGNNNRPSGVPDRFSGSKSGTSASLAITGLQ AEDEADYYCSSYTSGTWLFGGGTKLTVL | 34 |
| 3G7RY, VH | EVQLVESGGGLVQPGGSLRLSCAASGFTFSDYYMSWIRQA PGKGLEWVSYISSSGSTIYYADSVKGRFTISRDNSKNTLYL QMNSLRAEDTAVYYCARDYGRIAAAGRRYWGQGTLVTV SS | 35 |
| 3G7RY, VL | QSALTQPPSASATPGQRVTISCSGRTSNIGSNHVYWYQQLP GTAPKLLIYRNNQRPSGVPDRFSGSKSGTSASLAISGLRSED EADYYCATWDDSLSGEVFGGGTKLTVL | 36 |
| YS6, VH | QVQLQESGGGVVRPGGSLRLSCAASGFTFSDYYMSWIRQA PGKGLEWVSYISSSGSTIYYADSVKGRFTISRDNSKNTLYL QMNSLRAEDTAVYYCARDYGRIAAAGRHYWGQGTLVTV SS | 37 |
| YS6, VL | SSELTQDPAVSVALGQTVRITCQGDSLRSYYASWYQQKPG QAPVLVIYGKNNRPSGIPDRFSGSSSGNTASLTITGAQAEDE ADYYCNSRDSSGTHLEVFGGGTKVTVL | 38 |
| YS1, VH | EVQLVESGGGLVQPGGSLRLSCAASGFTFSDYYMSWIRQA PGKGLEWVSYISSSGSTIYYADSVKGRFTISRDNSKNTLYL QMNSLRAEDTAVYYCARDYGRIAAAGRHYWGQGTLVTV SS | 39 |
| YS1, VL | SSELTQDPAVSVALGQTVRITCQGDTLSTYYANWYQQKPG QAPVLVIYGKNNRPSGIPDRFSGSSSGNTASLTITGAQAEDE ADYYCHSRDISGNYLFASGTKLTVL | 40 |
| YS3, VH | QVQLQESGGGLVQPGGSLRLSCAASGFTFSSYWMSWVRQ APGKGLEWVADIKQDGSEKYYVDSVKGRFTISGDNAKNS LYLQMNSLRAEDTAVYYCAKDVGSTAINYVRAYTWFDP WGQGTLVTVSS | 41 |
| YS3, VL | QSVLTQPPSASGTPGQRVTISCSGSSSNIGSNTVNWSRQLPG TAPKLLIYSNNQRPSGVPDRFSGSKSGTSASLAISGLQSEDE ADYYCAAWDDSLNVYVFGTGTKVTVL | 42 |
| YS4, VH | QVQLQESGGGLVQPGGSLRLSCAASGFTFSNYAMSWVRQ APGKGLEWVSTISGSGSSTFYVDSVKGRFTISRDNSKNTLY LQMNSLRAEDTAVYYCAQGLYSSGWANWFDPRGQGTLV TVSS | 43 |
| YS4, VL | KIVLTQSPSSLSASVGDTVTIACRASRDIRNDLAWYQQKPG KAPKLLIYGASSLQSGVPSRFSGSGSGTEFILTISSLQPED FATYYCHRLNSYPLTFGGGTKVDIK | 44 |
| YS8, VH | QVQLQESGGGVVQPGRSLRLSCAASGFTFSSYGMHWVRQ APGKGLEWVAVISYDGSNKYYADSVKGRFTISRDNSKNTL YLQMNSLRAEDTAVYYCAKVMGLAAAGLDAFDIWGQGT TVTVSS | 45 |
| YS8, VL | NFMLTQPASLSGSPGQSITISCTGTSSDVGGYNYVSWYQQ HPGYAPKLMIYDVSNRPSGVSNRFSGSKSGNTASLTISGL QAEDEADYYCSSYTSSSTPWVFGGGTKLTVL | 46 |
| YS7, VH | QVQLVQSGGGVVQPGRSLRLSCAASGFTFSSYAMHWVRQ APGKGLEWVAVISYDGSNKYYADSVKGRFTISRDTSTNT LYLQMNSLRADDTAVYYCGRESSGSPGVWGQGTTVTVSS | 47 |
| YS7, VL | SYVLTQDPAVSVALGQTVRITCQGDSLRSYYASWYQQKP GQAPVLVIYGKNNRPSGIPDRFSGSSSGNTASLTITGAQ AEDEADYYCNSRDSSGNQFGGGTKLTVL | 48 |
| YS9, VH | QVQLVESGGGLIQPGGSLRLSCAASGFTVSSNYMSWVRQA PGKGLEWVSVIYTDGSTYYADSVKGRFTISRDNSKNTLYL QMNSLRAEDTAIYYCARDRGTSGYDWAWFDLWGQGTLV TVSS | 49 |

TABLE 2-continued

Antibody sequences.

| Identifier | Sequence | SEQ ID NO: |
|---|---|---|
| YS9, VL | SSELTQDPAVSVALGQTVRITCQGDSLRTYYASWYQQRPG QAPILVLYGKNNRPSGIPDRFSGSSSGNTASLTITGAQAE DEADYYCNSRDSSGNHVVFGGGTKLTVL | 50 |
| YS10, VH | QVQLQESGGGLVQPGGSLRLSCAASGFTFSSYAMSWVRQ APGKGLEWVSAISGSGGSTYYADSVKGRFTISRDNSKNTL YMQMNSLRAEDTAVYYCAKDRYYYGSGKDAFDIWGRGT MVTVSS | 51 |
| YS10, VL | QSVLTQPASVSGSPGQSITISCTGTGSDVGSYNYVSWYQ QNPGKAPKLMIYEVSNRPSGVSNRFSGSKSGNTASLTIS GLQAEDEADYYCSSYTTSSTLVFGGGTKVTVL | 52 |
| YS11, VH | QVQLVESGGGLVQPGGSLGLSCAASGFTFSNYWMSWVRQ APGKGLEWVANVRQDGGQKYYVDSVKGRFTISRDNAKN SLYLQMNSLRTEDTAVYFCVSQRNSGEHDYWGQGTLVTV SS | 53 |
| YS11, VL | SELTQDPAVSVALGQTVRITCQGDSLRSYYASWYQQKPGQ APVLVIYGENSRPSGIPDRFSGSSSGNTASLTITGAQAED EADYYCNSWDSSGNHVVFGGGTKLTVL | 54 |
| 3G7HY, VH | EVQLVESGGGLVQPGGSLRLSCAASGFTFSDYYMSWIRQA PGKGLEWVSYISSSGSTIYYADSVKGRFTISRDNSKNTLY LQMNSLRAEDTAVYYCARDYGRIAAAGRHYWGQGTLVTV SS | 55 |
| 3G7HY, VL | AIRMTQSPSSLSASVGDRVTITCRASQSISSYLNWYQQKPG KAPKLLIYAASSLQSGVPSRFSGSGSGTDFTLTISSLQPED FATYYCQQSYSTPRTFGQGTKLEIK | 56 |
| 3G7NY, VH | EVQLVESGGGLVQPGGSLRLSCAASGFTFSDYYMSWIRQA PGKGLEWVSYISSSGSTIYYADSVKGRFTISRDNSKNTLYL QMNSLRAEDTAVYYCARDYGRIAAAGRNYWGQGTLVTV SS | 57 |
| 3G7NY, VL | DIVMTQSPLSLPVTPGEPASISCRSSQSLLHSNGYDYLDWY LQKPGQSPQLLIYLGSNRASGVPDRFSGSGSGTDFTLKISR VETEDVGIYYCMQGLQTPSFGQGTKLEIK | 58 |
| 3G7, VH | QVQLQESGGGVVRPGGSLRLSCAASGFTFSDYYMSWIRQA PGKGLEWVSYISSSGSTIYYADSVKGRFTISRDNSKNTLYL QMNSLRAEDTAVYYCARDYGRIAAAGRHYWGQGTLVTV SS | 59 |
| 3G7, VL | SSELTQDPAVSVALGQTVRITCQGDSLRSYYASWYQQKPG QAPVPVIYGKNNRPSGIPDRFSGSSSGNTASLTITGAQAE DEADYYCNSRDSSSTHRGVFGGGTKLTVL | 60 |
| SB2, VH | EVQLVESGGGLVKPGGSLRLSCAASGFTFSDYYMSWIRQA PGKGLEWVSYISSSGSSIYYADSVKGRFTISRDNAKNSLY LQMNSLKAEDTAVYYCARDITDVVGVSFDYWGQGTLVTVS S | 61 |
| SB2, VL | DIQLTQSPSSLSASVGDRVTITCRASRSISTYLSWYQQKP GKAPKLLIYDASRLQNGVPSRFSGSGSDTDFTLTISSLQP EDFATYFCQQSYNPPWTFGQGTKLEIK | 62 |
| 2C8, VH | EVQLVESGGGVVQPGRSLRLSCAASGFTFSSYGMHWVRQ APGKGLEWVAVISYDGSNKYYADSVKGRFTISRDNSKNTL YLQMNSLRAEDTAEYYCAKVMGLAAAGLDAFDIWGQGT LVTVSS | 63 |
| 2C8, VL | QSALTQPASVSGSPGQSITISCTGTSSDVGGYNYVSWYQQH PGKAPKLMIYDVSNRPSGVSNRFSGSKSGNTASLTISGLQA EDEAYYCSSYTSSSDPWVFGGGTQLTVL | 64 |
| UA8kappa, VH | EVQLVESGGGVVQPGRSLRLSCAASGFTFSSFGMHWVRR APGKGLEWVAVISYDGSNQYYADSVKGRFTISRDNSKNTL YLQMNSLRAEDTAVYYCGSRPGGGYASGSTVAYWGQGT LVTVSS | 65 |
| UA8 kappa, VL | NIQMTQSPSSLSASVGDRVTITCRAGQPISTYVNWYQHKPG KAPKLLIYGASNLQSGVPSRFSGGGSATDFTLTISSLQPED FATYYCQQSYSSLLTFGDGTKVEIK | 66 |

TABLE 2-continued

Antibody sequences.

| Identifier | Sequence | SEQ ID NO: |
|---|---|---|
| 2B10, VH | QVQLQEPGGGLVQPGRSLRLSCAASGFTFDDYAMHWVRQ APGKGLEWVGRIKSKTDEGTTDYAAPVKGRFSISRDDSKN TLYLQMNSLKTEDTGVYYCTATKGLGGSKLGQGTLVTVS S | 67 |
| 2B10, VL | QSVLTQPPSASGTPGQRVTISCSGSSSNIGSNTVSWSRQL PGTAPKLLIYSNDQRPSGVPDRFSGSKSGTSASLAITGLQ PEDEADYYCGTWDSSLSAYVFGTGTKLTVL | 68 |
| UA20, VH | QVQLQESGGGLVKPGGSLRLSCAASGFTFSNAWMNWVRQ APGKGLEWVGRIKSKTDEGTTDYAAPVKGRFSISRDDSK NTLYLQMNSLKTEDTGVYYCTATKGLGGSKLGQGTLVTV SS | 69 |
| UA20, VL | QSVLTQPPSASGTPGQRVTISCSGSSSNIGNNTVNWSRQLP GTAPKLLIYSNDQRPSGVPDRFSGSKSGTSASLAITGLQPE DEADYYCGTWDSSLSAYVFGTGTKLTVL | 70 |
| 585II41, VH | QVQLVESGGGLVQPGGSLRLSCAASGFTFSSYAMGWVRQ APGKGLEWVSAISGSGGSTYYADSVKGRFTISRDNSKDTL YLQMNSLRAEDTAVYYCASRSLLDYWGQGTLVTVSS | 71 |
| 585II41, VL | NFMLTQDPAVSVALGQTVRITCQGDSLRSYYASWYQQKP GQAPLLVIYGKNNRPSGIPDRFSGSSSGNTASLTITGAQ AEDEADYYCNSRDSSGNPVFGGGTKVTVL | 72 |
| 585II41.1, VH | QVQLVESGGGLVQPGGSLRLSCAASGFTFSSYAMSWVRQ APGKGLEWVSAISGSGGSTYYADSVKGRFTISRDNSKDT LYLQMNSLRAEDTAVYYCASRSLLDYWGQGTLVTVSS | 73 |
| 585II41.1, VL | NFMLTQDPAVSVALGQTVRITCQGDSLRSYYASWYQQKP GQAPLLVIYGKNNRPSGIPDRFSGSSSGNTASLTITGAQ AEDEADYYCNSRDSSGNPVFGGGTKVTVL | 74 |

* CDR1, CDR2, and CDR3 of each of the VH and VL chains are represented by the first, second, and third underlined regions, respectively.

In some embodiments, an anti-CD46 antibody described herein comprises a heavy chain variable region comprising three complementarity determining regions (CDRs), wherein the heavy chain variable region comprises a variable heavy (VH) CDR1 that comprises an amino acid sequence of SEQ ID NO:3, a variable heavy (VH) CDR2 that comprises an amino acid sequence of SEQ ID NO:4, and a variable heavy (VH) CDR3 that comprises an amino acid sequence of SEQ ID NO: 5.

In some embodiments, an anti-CD46 antibody described herein comprises a light chain variable region comprising three CDRs, wherein the light chain variable region comprises a variable light (VL) CDR 1 that comprises an amino acid sequence of SEQ ID NO:6, a variable light (VL) CDR 2 that comprises an amino acid sequence of SEQ ID NO:7, and a variable light (VL) CDR 3 that comprises an amino acid sequence of SEQ ID NO:8.

In certain embodiments an anti-CD46 antibody described herein comprises a heavy chain variable region comprising three complementarity determining regions (CDRs) and a light chain variable region comprising three CDRs, wherein the heavy chain variable region comprises (i) a variable heavy (VH) CDR1 that comprises an amino acid sequence of SEQ ID NO:3, (ii) a variable heavy (VH) CDR2 that comprises an amino acid sequence of SEQ ID NO:4, and (iii) a variable heavy (VH) CDR3 that comprises an amino acid sequence of SEQ ID NO:5, and wherein the light chain variable region comprises (iv) a variable light (VL) CDR 1 that comprises an amino acid sequence of SEQ ID NO:6, (v) a variable light (VL) CDR 2 that comprises an amino acid sequence of SEQ ID NO:7, and (vi) a variable light (VL) CDR 3 that comprises an amino acid sequence of SEQ ID NO:8.

In certain embodiments, an anti-CD46 antibody described herein comprises a heavy chain variable region comprising three complementarity determining regions (CDRs), wherein the heavy chain variable region comprises a variable heavy (VH) CDR1 that comprises an amino acid sequence of SEQ ID NO: 11, a variable heavy (VH) CDR2 that comprises an amino acid sequence of SEQ ID NO: 12, and a variable heavy (VH) CDR3 that comprises an amino acid sequence of SEQ ID NO: 13.

In some embodiments, an anti-CD46 antibody described herein comprises a light chain variable region comprising three CDRs, wherein the light chain variable region comprises a variable light (VL) CDR 1 that comprises an amino acid sequence of SEQ ID NO:14, a variable light (VL) CDR 2 that comprises an amino acid sequence of SEQ ID NO:15, and a variable light (VL) CDR 3 that comprises an amino acid sequence of SEQ ID NO:16.

In some embodiments, an anti-CD46 antibody described herein comprises a heavy chain variable region comprising three complementarity determining regions (CDRs) and a light chain variable region comprising three CDRs, wherein the heavy chain variable region comprises (i) a variable heavy (VH) CDR1 that comprises an amino acid sequence of SEQ ID NO:11, (ii) a variable heavy (VH) CDR2 that comprises an amino acid sequence of SEQ ID NO: 12, and (iii) a variable heavy (VH) CDR3 that comprises an amino acid sequence of SEQ ID NO: 13, and wherein the light chain variable region comprises (iv) a variable light (VL) CDR 1 that comprises an amino acid sequence of SEQ ID NO:14, (v) a variable light (VL) CDR 2 that comprises an amino acid sequence of SEQ ID NO:15, and (vi) a variable light (VL) CDR 3 that comprises an amino acid sequence of SEQ ID NO:16.

In some embodiments, an anti-CD46 antibody described herein comprises a heavy chain variable region comprising three complementarity determining regions (CDRs), wherein the heavy chain variable region comprises a variable heavy (VH) CDR1 that comprises an amino acid sequence of SEQ ID NO: 19, a variable heavy (VH) CDR2 that comprises an amino acid sequence of SEQ ID NO:20, and a variable heavy (VH) CDR3 that comprises an amino acid sequence of SEQ ID NO:21.

In some embodiments, an anti-CD46 antibody described herein comprises a light chain variable region comprising three CDRs, wherein the light chain variable region comprises a variable light (VL) CDR 1 that comprises an amino acid sequence of SEQ ID NO:22, a variable light (VL) CDR 2 that comprises an amino acid sequence of SEQ ID NO:23, and a variable light (VL) CDR 3 that comprises an amino acid sequence of SEQ ID NO:24.

In some embodiments, an anti-CD46 antibody described herein comprises a heavy chain variable region comprising three complementarity determining regions (CDRs) and a light chain variable region comprising three CDRs, wherein the heavy chain variable region comprises (i) a variable heavy (VH) CDR1 that comprises an amino acid sequence of SEQ ID NO:19, (ii) a variable heavy (VH) CDR2 that comprises an amino acid sequence of SEQ ID NO:20, and (iii) a variable heavy (VH) CDR3 that comprises an amino acid sequence of SEQ ID NO:21, and wherein the light chain variable region comprises (iv) a variable light (VL) CDR 1 that comprises an amino acid sequence of SEQ ID NO:22, (v) a variable light (VL) CDR 2 that comprises an amino acid sequence of SEQ ID NO:23, and (vi) a variable light (VL) CDR 3 that comprises an amino acid sequence of SEQ ID NO:24.

In some embodiments, an anti-CD46 antibody described herein comprises a heavy chain variable region comprising three complementarity determining regions (CDRs), wherein the heavy chain variable region comprises a variable heavy (VH) CDR1 that comprises an amino acid sequence of SEQ ID NO:27, a variable heavy (VH) CDR2 that comprises an amino acid sequence of SEQ ID NO:28, and a variable heavy (VH) CDR3 that comprises an amino acid sequence of SEQ ID NO:29.

In some embodiments, an anti-CD46 antibody described herein comprises a light chain variable region comprising three CDRs, wherein the light chain variable region comprises a variable light (VL) CDR 1 that comprises an amino acid sequence of SEQ ID NO:30, a variable light (VL) CDR 2 that comprises an amino acid sequence of SEQ ID NO:31, and a variable light (VL) CDR 3 that comprises an amino acid sequence of SEQ ID NO:32.

In some embodiments, an anti-CD46 antibody used in the methods described herein comprises a heavy chain variable region comprising three complementarity determining regions (CDRs) and a light chain variable region comprising three CDRs, wherein the heavy chain variable region comprises (i) a variable heavy (VH) CDR1 that comprises an amino acid sequence of SEQ ID NO:27, (ii) a variable heavy (VH) CDR2 that comprises an amino acid sequence of SEQ ID NO:28, and (iii) a variable heavy (VH) CDR3 that comprises an amino acid sequence of SEQ ID NO:29, and wherein the light chain variable region comprises (iv) a variable light (VL) CDR 1 that comprises an amino acid sequence of SEQ ID NO:30, (v) a variable light (VL) CDR 2 that comprises an amino acid sequence of SEQ ID NO:31, and (vi) a variable light (VL) CDR 3 that comprises an amino acid sequence of SEQ ID NO: 32.

In some instances, an anti-CD46 antibody used in the methods described herein comprises a heavy chain variable region having at least 80%, 85%, 90%, 95%, or 99% sequence identity to one or more of SEQ ID NOs: 1, 9, 17, and/or 25; and a light chain variable region having at least 80%, 85%, 90%, 95% or 99% sequence identity to one or more of SEQ ID NOs: 2, 10, 18, and/or 26. In some instances, an anti-CD46 antibody described herein comprises a heavy chain variable region having at least 80%, 85%, 90%, 95%, or 99% sequence identity to SEQ ID NO:1; and a light chain variable region having at least 80%, 85%, 90%, 95% or 99% sequence identity to SEQ ID NO:2. In some instances, an anti-CD46 antibody described herein comprises a heavy chain variable region having at least 80%, 85%, 90%, 95%, or 99% sequence identity to SEQ ID NO:9; and a light chain variable region having at least 80%, 85%, 90%, 95% or 99% sequence identity to SEQ ID NO: 10. In some instances, an anti-CD46 antibody described herein comprises a heavy chain variable region having at least 80%, 85%, 90%, 95%, or 99% sequence identity to SEQ ID NO:17; and a light chain variable region having at least 80%, 85%, 90%, 95% or 99% sequence identity to SEQ ID NO:18. In some instances, an anti-CD46 antibody described herein comprises a heavy chain variable region having at least 80%, 85%, 90%, 95%, or 99% sequence identity to SEQ ID NO:25; and a light chain variable region having at least 80%, 85%, 90%, 95% or 99% sequence identity to SEQ ID NO:26. In some cases, an anti-CD46 antibody described herein comprises a heavy chain variable region comprising an amino acid sequence of SEQ ID NO:1 and a light chain variable region comprising an amino acid sequence of SEQ ID NO:2. In some cases, an anti-CD46 antibody described herein comprises a heavy chain variable region comprising an amino acid sequence of SEQ ID NO:9 and a light chain variable region comprising an amino acid sequence of SEQ ID NO: 10. In some cases, an anti-CD46 antibody described herein comprises a heavy chain variable region comprising an amino acid sequence of SEQ ID NO:17 and a light chain variable region comprising an amino acid sequence of SEQ ID NO:18. In some cases, an anti-CD46 antibody described herein comprises a heavy chain variable region comprising an amino acid sequence of SEQ ID NO:25 and a light chain variable region comprising an amino acid sequence of SEQ ID NO:26.

In some instances, an anti-CD46 antibody used in the methods described herein comprises a heavy chain variable region and a light chain variable region having at least 80%, 85%, 90%, 95%, or 99% sequence identity to an antibody illustrated in Table 2. In some cases, an anti-CD46 antibody described herein comprises a heavy chain variable region and a light chain variable region having at least 80% sequence identity to an antibody illustrated in Table 2. In some cases, an anti-CD46 antibody described herein comprises a heavy chain variable region and a light chain variable region having at least 85% sequence identity to an antibody illustrated in Table 2. In some cases, an anti-CD46 antibody described herein comprises a heavy chain variable region and a light chain variable region having at least 90% sequence identity to an antibody illustrated in Table 2. In some cases, an anti-CD46 antibody described herein comprises a heavy chain variable region and a light chain variable region having at least 95% sequence identity to an antibody illustrated in Table 2. In some cases, an anti-CD46 antibody described herein comprises a heavy chain variable region and a light chain variable region having at least 99% sequence identity to an antibody illustrated in Table 2. In some cases, an anti-CD46 antibody described herein comprises a heavy chain variable region and a light chain variable region to an antibody illustrated in Table 2.

Production of Antibodies or Binding Fragments Thereof

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, *BioTechniques* 17:242), which can involve the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or binding fragment thereof is optionally generated by immunizing an animal, such as a rabbit, to generate polyclonal antibodies or, more preferably, by generating monoclonal antibodies, e.g., as described by Kohler and Milstein (1975, *Nature* 256:495-497) or, as described by Kozbor et al. (1983, *Immunology Today* 4:72) or Cole et al. (1985 in *Monoclonal Antibodies and Cancer Therapy*, Alan R. Liss, Inc., pp. 77-96). Alternatively, a clone encoding at least the Fab portion of the antibody is optionally obtained by screening Fab expression libraries (e.g., as described in Huse et al., 1989, *Science* 246:1275-1281) for clones of Fab fragments that bind the specific antigen or by screening antibody libraries (See, e.g., Clackson et al., 1991, *Nature* 352:624; Hane et al., 1997 *Proc. Natl. Acad. Sci. USA* 94:4937).

In some embodiments, techniques developed for the production of "chimeric antibodies" (Morrison et al., 1984, *Proc. Natl. Acad. Sci.* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region, e.g., humanized antibodies.

In some embodiments, techniques described for the production of single chain antibodies (U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, *Science* 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, *Cell* 11:223), hypoxanthine-guanine phosphoribosyltransferase (Szybalska & Szybalski, 192, *Proc. Natl. Acad. Sci. USA* 48:202), and adenine phosphoribosyltransferase (Lowy et al., 1980, *Cell* 22:817) genes are employed in tk-, hgprt- or aprt-cells, respectively. Also, antimetabolite resistance are used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Clinical Pharmacy 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215) and hygro, which confers resistance to hygromycin (Santerre et al., 1984, *Gene* 30:147). Methods commonly known in the art of recombinant DNA technology which can be used are described in Ausubel et al. (eds., 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J Mol. Biol.* 150:1).

In some instances, the expression levels of an antibody are increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell Biol.* 3:257).

In some instances, an antibody or its binding fragment thereof is generated by chemical peptide synthesis techniques. Solid phase synthesis in which the C-terminal amino acid of the sequence is attached to an insoluble support followed by sequential addition of the remaining amino acids in the sequence is the preferred method for the chemical synthesis of the antibody binding fragments. Techniques for solid phase synthesis are described by Barany and Merrifield, Solid-Phase Peptide Synthesis; pp. 3-284 in The Peptides: Analysis, Synthesis, Biology. Vol. 2: Special Methods in Peptide Synthesis, Part A., Merrifield, et al. J. Am. Chem. Soc, 85: 2149-2156 (1963), and Stewart et al., Solid Phase Peptide Synthesis, 2nd ed. Pierce Chem. Co., Rockford, 111. (1984).

In some instances, any method known in the art for purification of an antibody can be used. Illustrative methods include, but are not limited to, chromatography (e.g., ion exchange, affinity, particularly by affinity for the specific antigen after Protein A, and sizing column chromatography), centrifugation, differential solubility, or by any other standard technique for the purification of proteins.

In certain embodiments the binding affinity (avidity) of the antibody (e.g., anti-CD46 antibody) is determined and can be optimized and/or increased (e.g., by mutation and successive rounds of panning a library, etc.). Methods of determining binding affinity are well known to those of skill in the art. Briefly, for example, the $K_D$ of the antibody is determined from the kinetics of binding to, e.g. the target cell in a BIAcore, a biosensor based on surface plasmon resonance. For this technique, the antigen or cell is coupled to a derivatized sensor chip capable of detecting changes in mass. When antibody is passed over the sensor chip, antibody binds to the antigen resulting in an increase in mass that is quantifiable. Measurement of the rate of association as a function of antibody concentration can be used to calculate the association rate constant ($k_{on}$). After the association phase, buffer is passed over the chip and the rate of dissociation of antibody ($k_{off}$) determined. $K_{on}$ is typically measured in the range $1.0 \times 10^2$ to $5.0 \times 10^6$ and $k_{off}$ in the range $1.0 \times 10^1$ to $1.0 \times 10^{-6}$. The equilibrium constant $K_D$ is often calculated as $k_{off}/k_{on}$ and thus is typically measured in the range $10^{-5}$ to $10^{-12}$. Affinities measured in this manner correlate well with affinities measured in solution by fluorescence quench titration.

Payloads

In some embodiments, an anti-CD46 antibody described herein is attached to a payload (e.g., a cytotoxic or cytostatic, drug, an immunomodulator, a cytokine, an imaging agent, a radiosensitizer, an effector cell, a viral particle, and the like). In some embodiments, an anti-CD46 antibody is attached to a cytotoxic/cytostatic drug. In various embodiments the payloads (e.g., drugs) being used to construct anti-CD46 payload conjugates include, but are not limited to microtubule inhibitors and DNA-damaging agents, polymerase inhibitors (e.g., the polymerase II inhibitor, α-amanitin), and the like. In some embodiments, the antibody is conjugated to the payload (e.g., a drug) directly or through a linker, while in other embodiments, the antibody is conjugated to a payload carrier (e.g., a drug carrier such as a liposome containing the drug, a polymeric drug carrier, a nanoparticle drug carrier, a lipid drug carrier, a dendrimeric drug carrier, and the like). In some instances, the anti-CD46 antibody is attached directly. In other instances, the anti-CD46 antibody is attached indirectly via a linker.

In some embodiments, the payload comprises a tubulin inhibitor, including, but not limited to auristatin, Dolastatin-10, synthetic derivatives of the natural product Dolastatin-10, maytansine or a maytansine derivative, and the like.

In some embodiments, the payload comprises an auristatin. In some instances, the auristatin comprises one or more of Auristatin E (AE), Monomethylauristatin E (MMAE), Monomethylauristatin F (MMAF), vcMMAE, vcMMAF, and the like.

In some embodiments, the payload comprises a maytansine. Illustrative maytansines include, but are not limited to, Mertansine (DM1); and an analogue of maytansine such as DM3 or DM4, and the like.

In some instances, the payload comprises a DNA interacting agent. In certain embodiments the DNA interacting agent includes, but is not limited to calicheamicins, duocarmycins, pyrrolobenzodiazepmes (PBDs), and the like.

In one illustrative, but non-limiting embodiment, the payload comprises a calicheamicin. Calicheamicins target DNA and cause strand scission. In certain embodiments the payload comprises calicheamicin or a calicheamicin analog. Calicheamicin analogs are described in U.S. Pat. No. 5,264,586, which is incorporated herein by reference for the calicheamicin analogs described therein.

In certain illustrative, but non-limiting embodiments, the payload comprises a duocarmycin. Duocarmycins are DNA damaging agents able to exert their mode of action at any phase in the cellular cycle. Agents that are part of this class of duocarmycins typically have potency in the low picomolar range. Illustrative duocarmyhcins (e.g., duocarmycin analogues) that are used as payloads attached to the antibodies described herein include, but are not limited to duocarmycin A, duocarmycin B1, duocarmycin B2, duocarmycin C I, duocarmycin C2, duocarmycin D, duocarmycin SA, Cyclopropylbenzoindole duocarmycin (CC-1065), Centanamycin, Rachelmycin, Adozelesin, Bizelesin, Carzelesin, and the like.

In another illustrative, but non-limiting embodiment, the payload comprises a pyrrolobenzodiazepine. In certain embodiments the payload comprises a synthetic derivative of two pyrrolobenzodiazepmes linked by a flexible polymethylene tether. Pyrrolobenzodiazepmes (PBDs) and PBD dimers are described in U.S. Pat. No. 7,528,126 B2, which is incorporated herein by reference for the Pyrrolobenzodiazepmes and PBD dimers described therein. In certain embodiments the pyrrolobenzodiazepine is selected from the group consisting of: Anthramycin (and dimers thereof), Mazethramycin (and dimers thereof), Tomaymycin (and dimers thereof), Prothracarcin (and dimers thereof), Chicamycin (and dimers thereof), Neothramycin A (and dimers thereof), Neothramycin B (and dimers thereof), DC-81 (and dimers thereof), Sibiromycin (and dimers thereof), Porothramycin A (and dimers thereof), Porothramycin B (and dimers thereof), Sibanomycin (and dimers thereof), Abbeymycin (and dimers thereof), SG2000, and SG2285.

In some embodiments, the payload comprise a polymerase inhibitor, including, but not limited to polymerase II inhibitors such as a-amanitin, and poly(ADP-ribose) polymerase (PARP) inhibitors. Illustrative PARP inhibitors include, but are not limited to Iniparib (BSI 201), Talazoparib (BMN-673), Olaparib (AZD-2281), Olaparib, Rucaparib (AG014699, PF-01367338), Veliparib (ABT-888), CEP 9722, MK 4827, BGB-290, 3-aminobenzamide, and the like.

In some embodiments, the cytotoxic/cytostatic agent comprises a protein or peptide toxin or fragment thereof. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, a-sacrin, certain A leurites fordii proteins, certain Dianthin proteins, Phytolacca americana proteins (PAP, PAPII and PAP-S), Morodica charantia inhibitor, curcin, crotin, Saponaria officinalis inhibitor, gelonin, mitogillin, restrictocin, phenomycin, enomycin, and the tricothecenes, for example.

In some embodiments, the cytotoxins include, but are not limited to, *Pseudomonas* exotoxins, Diphtheria toxins, ricin, abrin and derivatives thereof. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain 1a (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain 1b (amino acids 365-399) remains undefined, although a large part of it, amino acids 365-380, can be deleted without loss of cytotoxicity. See Siegall et al. (1989) J. Biol. Chem. 264: 14256-14261.

In some instances, an anti-CD46 antibody is attached to a molecule in which domain 1a (amino acids 1 through 252) is deleted and amino acids 365 to 380 have been deleted from domain 1b. In certain embodiments all of domain 1b and a portion of domain II (amino acids 350 to 394) are deleted, particularly if the deleted sequences are replaced with a linking peptide.

In some cases, PE and other cytotoxic proteins are further modified using site-directed mutagenesis or other techniques known in the art, to alter the molecule for a particular desired application. For example, means to alter PE in a manner that does not substantially affect the functional advantages provided by PE described here are also used and such resulting molecules are intended to be covered herein.

Methods of cloning genes encoding PE fused to various ligands are well known to those of skill in the art (see, e.g., Siegall et al. (1989) FASEB J., 3: 2647-2652; and Chaudhary et al. (1987) Proc. Natl. Acad. Sci. USA, 84: 4538-4542).

In some embodiments, the payload comprises an immunomodulator. In such cases, an anti-CD46 antibody described herein are attached to an immunomodulatory and function to localize the immunomodulatory at the cancer cell/tumor site. Numerous immunomodulators that can activate an immune response are known to those of skill in the art. In one illustrative, but non-limiting embodiment the immunomodulatory comprise an anti-CD3 antibody. Anti-CD3 monoclonal antibodies induce the proliferation of human T-cells cells in vitro and activate specific and non-specific cytolysis by human T-cell clones and human peripheral blood lymphocytes. In vivo administration of anti-CD3 prevents tumor growth of a UV-induced mouse fibro sarcoma.

In certain embodiments, the immunomodulators comprise agents that blockade immune checkpoints. Immune checkpoints refer to a plethora of inhibitory pathways hardwired into the immune system that are crucial for maintaining self-tolerance and modulating the duration and amplitude of physiological immune responses in peripheral tissues in order to minimize collateral tissue damage. In some cases, tumors co-opt certain immune-checkpoint pathways as a mechanism of immune resistance, particularly against T cells that are specific for tumor antigens. Because many of the immune checkpoints are initiated by ligand-receptor interactions, they can be readily blocked by antibodies or modulated by recombinant forms of ligands or receptors.

Cytotoxic T-lymphocyte-associated antigen 4 (CTLA4) antibodies were the first of this class of immunotherapeutics to achieve US Food and Drug Administration (FDA) approval. The first such drug to receive approval, ipilimumab (Yervoy®), for the treatment of advanced melanoma, blocks the activity of a checkpoint protein known as CTLA4, which is expressed on the surface of activated immune cells called cytotoxic T lymphocytes. CTLA4 acts as a "switch" to inactivate these T cells, thereby reducing the strength of immune responses; ipilimumab binds to CTLA4 and prevents it from sending its inhibitory signal. Two other FDA-approved checkpoint inhibitors, nivolumab (Opdivo®) and pembrolizumab (Keytruda®), work in a similar way, but they target a different checkpoint protein on activated T cells known as PD-1. Nivolumab is approved to treat some patients with advanced melanoma or advanced lung cancer, and pembrolizumab is approved to treat some patients with advanced melanoma.

Accordingly in certain embodiments the immunomodulators comprise antibodies directed against CTLA4 (e.g., ipilimumab), and/or antibodies directed against PD-L1 (e.g., nivolumab, pembrolizumab), and/or antibodies directed against PD-L2.

Other examples of immune modulators that can be attached to the anti-CD46 antibody include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, xanthines, stem cell growth factors, lymphotoxins, hematopoietic factors, tumor necrosis factor (TNF) (e.g., TNFα), interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-alpha, interferon-beta, interferon-gamma), the stem cell growth factor designated "S1 factor," erythropoietin and thrombopoietin, or a combination thereof.

In some instances, a payload described herein comprises a cytokine. In some embodiments, the cytokine comprises one or more of IL-2, IL-2, IL-3, IL-6, IL-10, IL-12, IL-18, IL-21, interferon (e.g., IFNα, IFNβ), or TNFα.

Useful immunomodulatory agents also include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4(5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Illustrative immunosuppressive agents include, but are not limited to 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, cytokine or cytokine receptor antagonists (e.g., anti-interferon antibodies, anti-IL10 antibodies, anti-TNFα antibodies, anti-IL2 antibodies), streptokinase, TGFβ, rapamycin, T-cell receptor, T-cell receptor fragments, and T cell receptor antibodies.

In some embodiments, the payload comprises an imaging agent, which can facilitate tumor detection and/or localization. In some embodiments, the payload comprises a "radio-opaque" label, e.g. a label visualized using x-rays. Radio-opaque materials are well known to those of skill in the art. Exemplary radio-opaque materials include iodide, bromide or barium salts. Additional radiopaque materials include, but are not limited to, organic bismuth derivatives {see, e.g., U.S. Pat. No. 5,939,045), radio-opaque polyurethanes (see, e.g., U.S. Pat. No. 5,346,981), organobismuth composites (see, e.g., U.S. Pat. No. 5,256,334), radio-opaque barium polymer complexes (see, e.g., U.S. Pat. No. 4,866,132), and the like.

In some embodiments, the anti-CD46 antibodies described herein are coupled directly to the radio-opaque moiety or are attached to a "package" (e.g., a chelate, a liposome, a polymer microbead, a nanoparticle, etc.) carrying, containing, or comprising the radio-opaque material, e.g., as described below.

In addition to radio-opaque labels, other labels are also suitable for use. Detectable labels suitable for use in immunoconjugates include any composition detectable by spectroscopic, photochemical, biochemical, immunochemical, electrical, optical or chemical means. Useful labels in the include magnetic beads (e.g., DYNABEADS™) fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads, nanoparticles, quantum dots, and the like.

In certain embodiments, suitable radiolabels include, but are not limited to, $^{99}$Tc, $^{203}$P, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd $^{159}$Gd, $^{166}$Ho, $^{172}$Tm, $^{169}$Yb, $^{175}$Yb, $^{177}$Lu, $^{10}$5Rh, and $^{111}$Ag.

Means of detecting such labels are well known to those of skill in the art. Thus, for example, certain radiolabels are optionally detected using photographic film, scintillation detectors, PET imaging, MRI, and the like. In some cases, fluorescent markers are detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

In another embodiment, the payload comprises a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945, 439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

In certain embodiments, the payload comprises an alpha emitter, i.e. a radioactive isotope that emits alpha particles. Alpha-emitters have recently been shown to be effective in the treatment of cancer (see, e.g., McDevitt et al. (2001) Science 294: 1537-1540; Ballangrud et al. (2001) Cancer Res. 61: 2008-2014; Borchardt et al. (2003) Cancer Res. 63: 5084-50). Suitable alpha emitters include, but are not limited to Bi, $^{213}$Bi, $^{211}$At, and the like.

In some embodiments, the payload comprises a modified effector cell. In some embodiments, the modified effector cell comprises a CAR-T cell or a CAR-NK cell.

In some embodiments, the payload comprises a viral particle (e.g., a filamentous phage, an adeno-associated virus (AAV), a lentivirus, and the like). The antibody can be conjugated to the viral particle and/or can be expressed on the surface of the viral particle (e.g. a filamentous phage). The viral particle can additionally include a nucleic acid that is to be delivered to the target (e.g., prostate cancer) cell. The use of viral particles to deliver nucleic acids to cells is described in detail in WO 99/55720, U.S. Pat. Nos. 6,670, 188, 6,642,051, and 6,669,936.

Additional Therapeutic Agents

In some embodiments, one or more methods described herein further comprise administration of an additional therapeutic agent. Illustrative therapeutic agents include, but are not limited to, anti-cancer antibodies (e.g., HERCEPTIN®), antimetabolites, alkylating agents, topoisomerase inhibitors, microtubule targeting agents, kinase inhibitors, protein synthesis inhibitors, somatostatin analogs, glucocorticoids, aromatose inhibitors, mTOR inhibitors, protein Kinase B (PKB) inhibitors, phosphatidylinositol, 3-Kinase (PI3K) Inhibitors, cyclin dependent kinase inhibitors, anti-TRAIL molecules, MEK inhibitors, and the like. In certain embodiments the anti-cancer compounds include, but are not limited to flourouracil (5-FU), capecitabine/XELODA, 5-Trifluoromethyl-2'-deoxyuridine, methotrexate sodium, raltitrexed/Tomudex, pemetrexed/Alimta®, cytosine Arabinoside (Cytarabine, Ara-C)/Thioguanine, 6-mercaptopurine (Mercaptopurine, 6-MP), azathioprine/Azasan, 6-thioguanine (6-TG)/Purinethol (TEVA), pentostatin/Nipent, fludarabine phosphate/Fludara®, cladribine (2-CdA, 2-chlorodeoxyadenosine)/Leustatin, floxuridine (5-fluoro-2)/FUDR (Hospira, Inc.), ribonucleotide Reductase Inhibitor (RNR), cyclophosphamide/Cytoxan (BMS), neosar, ifosfamide/Mitoxana, thiotepa, BCNU-1,3-bis(2-chloroethyl)-1-nitosourea, 1,-(2-chloroethyl)-3-cyclohexyl-1nitrosourea, methyl CCNU, hexamethylmelamine, busulfan/Myleran, procarbazine HCL/Matulane, dacarbazine (DTIC), chlorambucil/Leukaran®, melphalan/Alkeran, cisplatin (Cisplatinum, CDDP)/Platinol, carboplatin/Paraplatin, oxaliplatin/Eloxitan, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin HCL/Doxil, daunorubicin citrate/Daunoxome®, mitoxantrone HCL/Novantrone, actinomycin D, etoposide/Vepesid, topotecan HCL/Hycamtin, teniposide (VM-26), irinotecan HCL(CPT-11), Camptosar®, camptothecin, Belotecan, rubitecan, vincristine, vinblastine sulfate, vinorelbine tartrate, vindesine sulphate, paclitaxel/Taxol, docetaxel/Taxotere, nanoparticle paclitaxel, abraxane, ixabepilone, larotaxel, ortataxel, tesetaxel, vinfiunine, and the like. In certain embodiments the anti-cancer drug(s) comprise one or more drugs selected from the group consisting of carboplatin(e.g., PARAPLATIN®), Cisplatin (e.g., PLATINOL®, PLATINOL-AQ®), Cyclophosphamide (e.g., CYTOXAN®, NEOSAPv®), Docetaxel (e.g., TAXOTERE®), Doxorubicin (e.g., ADRIAMYCIN®), Erlotinib (e.g., TARCEVA®), Etoposide (e.g., VEPESID®), Fluorouracil (e.g., 5-FU®), Gemcitabine (e.g., GEMZAR®), imatinib mesylate (e.g., GLEEVEC®), Irinotecan (e.g., CAMPTOSAR®), Methotrexate (e.g., FOLEX®, MEXATE®, AMETHOPTERIN®), Paclitaxel (e.g., TAXOL®, ABRAXANE®), Sorafmib (e.g., NEXAVAR®), Sunitinib (e.g., SUTENT®), Topotecan (e.g., HYCAMTIN®), Vinblastine (e.g., VELBAN®), Vincristine (e.g., ONCOVIN®, VINCASAR PFS®). In certain embodiments the anti-cancer drug comprises one or more drugs selected from the group consisting of retinoic acid, a retinoic acid derivative, doxorubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, zoledronic acid, vinblastine, etc.), an antisense molecule, an SiRNA, and the like.

In some embodiments, the additional therapeutic agent comprises an encapsulation system, such as a viral capsid, a liposome, or micelle that contains a therapeutic composition such as a drug, a nucleic acid (e.g. an antisense nucleic acid or another nucleic acid to be delivered to the cell), or another therapeutic moiety that is preferably shielded from direct exposure to the circulatory system. Means of preparing liposomes attached to antibodies are well known to those of skill in the art (see, e.g., U.S. Pat. No. 4,957,735, Connor et al. (1985) Pharm. Ther., 28: 341-365, and the like).

Methods of Antibody-Payload Conjugation

In some embodiments, an anti-CD46 antibody (e.g., an anti-CD46 antibody described herein) and a payload are attached by any of a number of means well known to those of skill in the art. In certain embodiments the payload is conjugated, either directly or through a linker (spacer), to the anti-CD46 antibody. However, in certain embodiments, where both the payload molecule is or comprises a polypeptide it is possible to recombinantly express the chimeric molecule as a single-chain fusion protein.

In certain embodiments, the CD46 specific antibody is chemically conjugated to a payload (e.g., a cytotoxin, a label, a ligand, a drug, a liposome, etc.). Means of chemically conjugating molecules are well known to those of skill.

In some instances, procedures for attaching a payload to an antibody vary according to the chemical structure of the payload and/or antibody. Polypeptides typically contain variety of functional groups; e.g., carboxylic acid (COOH) or free amine ($-NH_2$) groups, that are available for reaction with a suitable functional group on a payload to bind the payload thereto.

In certain embodiments, the antibody and/or the payload can be derivatized to expose or attach additional reactive functional groups. The derivatization can involve attachment of any of a number of linker molecules such as those available from Pierce Chemical Company, Rockford Illinois.

A "linker", as used herein, is a molecule that is used to join the targeting molecule to the payload molecule. The linker is capable of forming covalent bonds to both the targeting molecule and to the payload molecule. Suitable linkers are well known to those of skill in the art and include, but are not limited to, straight or branched-chain carbon linkers, heterocyclic carbon linkers, or peptide linkers. Where the targeting molecule and the payload molecule are polypeptides, the linkers may be joined to the constituent amino acids through their side groups (e.g., through a disulfide linkage to cysteine). However, in a preferred embodiment, the linkers will be joined to the alpha carbon amino or carboxyl groups of the terminal amino acids.

In some embodiments, antibody payload conjugates are generated using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an illustrative, but non-limiting, chelating agent for conjugation of, e.g., a radionucleotide to the antibody (see, e.g., WO 1994/011026 (PCT/US 1993/010953)).

In some embodiments, conjugation of payloads (e.g., drugs, liposomes, etc.). or linkers attached to the payloads, to an antibody takes place at solvent accessible reactive amino acids such as lysines or cysteines that can be derived from the reduction of inter-chain disulfide bonds in the antibody. In certain embodiments cysteine conjugation can occur after reduction of four inter-chain disulfide bonds.

In certain embodiments site-specific conjugation, in which a known number of linker-drugs are consistently conjugated to defined sites in the antibody can be performed to produce a highly homogenous construct. Drug-to-antibody ratio (DAR) can precisely controlled and can be tailored to various linker-drugs, producing, for example, either 2- or 4-DAPv site-specific ADCs.

A number of methods are known to achieve sites-specific conjugation. For example, the amino acid cysteine contains a reactive thiol group that serves essential roles in the structure and function of many proteins. Conjugation of thio-reactive probes to proteins through cysteine residues has long been a method for protein labeling, and it has also been applied to the generation of antibody drug conjugates (ADCs). In certain illustrative, but non-limiting embodiments, this process involves partial reduction of existing disulfide bonds (e.g., interchain disulfide bonds).

In certain embodiments to maintain disulfide bonds, cysteine residues are engineered into proteins. The success of using introduced cysteine residues for site-specific conjugation relies on the ability to select proper sites in which cysteine-substitution does not alter protein structure or function. To accomplish this, the Phage Elisa for Selection of Reactive Thiols (PHESELECTOR) was developed by introducing reactive cysteine residues into an antibody-Fab (trastuzumab-Fab 4D5) at various sites, displaying the Fab on phage, and screening to identify reactive cysteines that do not interfere with antigen binding (see, e.g., Junutula et al. (2008) J. Immunol. Meth. 332: 41-52).

The PHESELECTOR approach has been demonstrated to be efficient and specific, especially compared with conventional cysteine conjugation. It has been demonstrated that the optimal sites for cysteine found using, e.g., an antibody fragment (e.g., Fab) and the PHESELECTOR method can also be applied to full-length antibodies, and data indicate that these sites work well for site-specific conjugation to other mAbs (see, e.g., Boswell et al. (2011) Bioconjug. Chem. 22: 1994-2004; Boswell et al. (2012) Soc. Nuclear Med. 53: 1454-1461; Shen et al. (2012) Nat. Biotechnol. 30: 184-189).

Another illustrative, but non-limiting strategy for site-specific conjugation centers on the insertion of amino acids with bio-orthogonal reactive handles such as the amino acid selenocysteine and the unnatural amino acid, acetylphenylalanine (pAcPhe). Two methods have been developed to employ these amino acids and both utilize stop codons. However, one method incorporates selenocysteine (Sec) by pairing the opal stop codon, UGA, with a Sec insertion sequence and the other method incorporates acetylphenylalanine at the amber stop codon, UAG, using a tRNA/aminoacyltRNA synthetase pair. Selenocysteine, employed by the first method, is very similar to the amino acid, cysteine, but contains a selenium atom in place of the sulfur atom. The selenolate group is a more reactive nucleophile than the thiolate counterpart, rendering it amenable to conjugation with electrophilic compounds under conditions in which selenocysteine is selectively activated. There are approximately 25 known selenium-containing proteins in mammals, including proteins such as glutathione peroxidases and thioreductases (Kryukov et al. 92003) Science, 300: 1439-1443). Under normal conditions, UGA codes for transcriptional termination; however, in the presence of a Sec insertion sequence (SECIS) located in the 3' UTR of Sec containing proteins, termination is prevented by the formation of an mRNA secondary structure and Sec is inserted at the UGA codon (Caban and Copeland (2006) CellMol. Life Sci. 63: 73-81). Sec insertion can be engineered into non-Sec coding genes by insertion of the UGA codon and a SECIS at the 3' end of the gene. This technique has been used, inter alia, in the Sec labeling and subsequent site-specific conjugation of mAbs (see, e.g., Hofer et al. (2009) Biochem. 48: 12047-12057).

Still another illustrative method for site-specific conjugation utilizes the unnatural amino acid, p-acetylphenylalanine (pAcPhe). pAcPhe contains a keto group that can be selectively conjugated to a drug containing an alkoxy-amine through an oxime ligation. To incorporate pAcPhe into an antibody, the amber stop codon is substituted into the antibody at the desired location. The antibody cDNA is then co-expressed with an amber suppressor tRNA and the properly paired mutant tRNA sythetase. The tRNA sythetase loads pAcPhe onto the amber tRNA and thus pAcPhe is incorporated into the antibody at the amber site UAG (see, e.g., Liu et al. 92007) Nat. Meth. 4: 239-244; Wang et al. (2003) Proc. Natl. Acad. Sci. USA, 100: 56-61; Axup (2012) Proc. Natl. Acad. Sci. USA, 109: 16101-16116).

In addition to pAcPhe, other unnatural amino acids are exploited for use in site-specific conjugation using similar processes involving matching tRNA/aminoacyl-tRNA synthetase pairs (see, e.g., Young (2002) J. Mol. Biol. 395: 361-374; Kiick et al. (2002) Proc. Natl. Acad. Sci. USA, 99: 19-24).

In various embodiments the use of enzymes to catalyze bond formation can be exploited for use in site-specific conjugation. For example, the glycotransferase platform uses a mutant glycotransferase to attach a chemically active sugar moiety to a glycosylation site on an antibody. Molecules of choice can then be conjugated to the chemical handle on the sugar moiety. In another illustrative, but non-limiting approach transglutaminase is used to form a bond between an amine group on the linker/drug and an engineered glutamine residue on the antibody.

Glycotransferases are a large family of proteins involved in the synthesis of oligosaccharides and are responsible for the transfer of a sugar residue from an activated sugar nucleotide to a sugar acceptor or glycoprotein/lipid. The structures of several glycotransferases are known and reveal that sugar donor specificity is determined by a few amino acids in the catalytic pocket (Qasba et al. (2005) Trends Biochem. Sci. 30: 53-62), Using this knowledge, residues have been mutated in the pocket of the glycotransferase, e.g., B4Gal-Tl, to broaden donor specificity and allow the transfer of the chemically reactive sugar residue, 2-keto-Gal (see, e.g., Ramakrishnan et al. (2002) J. Biol. Chem. 277: 20833-20839). This technology allows for the ability to transfer a chemically reactive sugar to any lipid or protein containing a glycosylation site. Human IgG antibodies contain an N-glycosylation site at the conserved Asn-297 of the Fc fragment. The glycans attached to this site are generally complex, but can be degalactosylated down to GO, onto which a mutant glycotransferase is capable of transferring C2-keto-Gal with high efficiency (see, e.g., Boeggeman et al. (2009) Bioconjug. Chem. 20: 1228-1236). The active chemical handle of C2-keto Gal can then be coupled to biomolecules with an orthogonal reactive group. This approach has been used successfully for the site-specific conjugation of the anti-Her2 antibody, trastuzumab, with Alexa Fluor 488 aminooxyacetamide and is a viable technique for site-specific ADC generation (Id.).

The second platform utilizes transglutaminase to catalyze the formation of a covalent bond between a free amine group and a glutamine side chain. Transglutaminase from *Streptoverticillium mobaraense* (mTG) is commercially available and has been used extensively as a protein crosslinking agent (see, e.g., Yokoyama et al. (2004) Appl. Microbiol. Biotechnol. 64: 447-454). mTG does not recognize any of the natural occurring glutamine residues in the Fc region of glycosylated antibodies, but does recognize a "glutamine tag" that can be engineered into an antibody (see, e.g., Jeger et al. (2010) *Angew Chem. Int. Ed. Engl.* 49: 9995-9997). By way of illustration, the glutamine tag, LLQG, has been engineered into different sites in the constant domain of an antibody targeting the epidermal growth factor receptor. mTG was then used to conjugate these sites with fluorophores or monomethyl dolastatin 10 (MMAD) and several sites where found to have good biophysical properties and a high degree of conjugation. mTG was also able to conjugate to glutamine tags on anti-Her2 and anti-M1S1 antibodies. An antiM1S1-vc-MMAD conjugate displayed strong in vitro and in vivo activity, suggesting that conjugation using this method does not alter antibody binding or affinity and demonstrates the utility of this approach in the site-specific conjugation of ADCs (see, e.g., Strop et al. (2013) *Chem. Biol.* 20: 161-167).

In addition to glycotransferases and transglutaminases, other enzymes have been explored for use in protein labeling (Sunbul and Yin (2009) Org. Biomol. Chem. 7: 3361-3371). One such enzyme, formylglycine generating enzyme, recognizes the sequence CxPxR and oxidizes a cysteine residue to form formylglycine, thus generating a protein with an aldehyde tag. The aldehyde group can then be conjugated to molecule of choice through, e.g., hydrozino-Pictet-Spengler chemistry.

Many other procedures and linker molecules for attachment of various compounds including radionuclide metal chelates, toxins and drugs to proteins such as antibodies are known (see, e.g., European Patent Application No. 188,256; U.S. Pat. Nos. 4,671,958, 4,659,839, 4,414,148, 4,699,784; 4,680,338; 4,569,789; and 4,589,071; and Borlinghaus et al. (1987) *Cancer Res.* 47: 4071-4075). In particular, production of various immunotoxins is well-known within the art and can be found, for example in "*Monoclonal Antibody-Toxin Conjugates: Aiming the Magic Bullet*," Thorpe et al., *Monoclonal Antibodies in Clinical Medicine*, Academic Press, pp. 168-190 (1982), Waldmann (1991) *Science*, 252: 1657, U.S. Pat. Nos. 4,545,985 and 4,894,443.

In some circumstances, it is desirable to free the payload from the antibody when the immunoconjugate has reached its target site. Therefore, immunoconjugates comprising linkages that are cleavable in the vicinity of the target site may be used when the payload is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. Illustrative cleavable linkers include, but are not limited to, acid-labile linkers, protease cleavable linkers, disulfide linkers, and the like. Acid-labile linkers are designed to be stable at pH levels encountered in the blood, but become unstable and degrade when the low pH environment in lysosomes is encountered. Protease-cleavable linkers are also designed to be stable in blood/plasma, but rapidly release free drug inside lysosomes in cancer cells upon cleavage by lysosomal enzymes. They take advantage of the high levels of protease activity inside lysosomes and typically include a peptide sequence that is recognized and cleaved by these proteases, e.g., as occurs with a dipeptide Val-Cit linkage that is rapidly hydrolyzed by cathepsins.

Disulfide linkers exploit the high level of intracellular reduced glutathione to release free drug inside the cell.

Identification of Cancers Responsive to CD46-Targeted Therapy.

In certain embodiments methods are provided for determining whether a cancer in a subject is responsive to a CD46-targeted therapy. In some cases, the method(s) comprises (a) providing a biological sample from the subject comprising cancer cells; and (b) determining whether nucleic acid in the cancer cells show a modification at chromosome location 1q21; wherein a modification at chromosome location 1q21 indicates that the cancer is responsive to the CD46-targeted therapy. In some cases, the modification at 1q21 is copy number gain of 1q21. In some cases, the cancer cells further comprise an overexpression of CD46. In some embodiments, a modification at 1q21 is determined prior to initiation of a treatment. In some cases, a modification at 1q21 is determined as part of monitoring the progress of a treatment regimen. In some cases, the CD46-targeted therapy comprises an anti-CD46 antibody, an oncolytic virus that targets CD46, or an engineered effector cell. In some instances, the CD46-targeted therapy comprises an anti-CD46 antibody. In some instances, the CD46-targeted therapy comprises an oncolytic virus (e.g., an oncolytic measles virus) that targets CD46. In some cases, the CD46-targeted therapy comprises a modified effector cell (e.g., CAR-T or CAR-NK). In some cases, the CD46-targeted therapy comprises a pharmaceutical composition comprising an anti-CD46 antibody.

Methods of determining the copy number gain of a particular genomic region are well known in the art, and include, but are not limited to, hybridization and amplification based assays. In some cases, DNA copy number gains is identified using fluorescent in situ hybridization (FISH), comparative genomic hybridization (CGH) (including both dual channel hybridization profiling or single channel hybridization profiling (e.g. SNP-CGH)). Other suitable methods include PCR (including, but not limited to, RT-PCR, Q-PCR, and the like), nucleic acid sequencing, or Southern blot analysis. In some cases, the methods comprise fluorescent in-situ hybridization (FISH), gene chip hybridization, multiplexed gene expression analysis, hybridization based digital barcode quantification assays, or lysate based hybridization assays utilizing branched DNA signal amplification.

In some embodiments, the fluorescent in-situ hybridization (FISH) is used to determine the copy number gain of a particular genomic region. Fluorescence in situ hybridization (FISH) is known to those of skill in the art (see Angerer, 1987 Meth. Enzymol., 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments.

In a typical in situ hybridization assay, cells or tissue sections are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

In some embodiments, the DNA copy number gains are identified using CGH. In comparative genomic hybridization methods, a "test" collection of nucleic acids (e.g. from a tumor or cancerous cells) is labeled with a first label, while a second collection (e.g. from a normal cell or tissue) is labeled with a second label. The ratio of hybridization of the nucleic acids is determined by the ratio of the first and second labels binding to each fiber in an array. Differences in the ratio of the signals from the two labels, for example, due to gene amplification in the test collection, is detected and the ratio provides a measure of the gene copy number, corresponding to the specific probe used. A cytogenetic representation of DNA copy-number variation can be generated by CGH, which provides fluorescence ratios along the length of chromosomes from differentially labeled test and reference genomic DNAs.

In some embodiments, the DNA copy number gains are analyzed by microarray based CGH (array-CGH). Microarray technology offers high resolution. For example, the traditional CGH generally has a 20 Mb limited mapping resolution; whereas in microarray based CGH, the fluorescence ratios of the differentially labeled test and reference genomic DNAs provide a locus-by-locus measure of DNA copy-number variation, thereby achieving increased mapping resolution. Details of various microarray methods can be found in the literature. See, for example, U.S. Pat. No. 6,232,068; Pollack et al., Nat. Genet., 23(1):41-6, (1999), Pastinen (1997) Genome Res. 7: 606614; Jackson (1996) Nature Biotechnology 14:1685; Chee (1995) Science 274: 610; WO 96/17958, Pinkel et al. (1998) Nature Genetics 20: 207-211 and others. High resolution CGH arrays can be performed using the Agilent or Affymetrix platforms. The DNA used to prepare the CGH arrays is not critical. For example, the arrays can include genomic DNA, e.g., overlapping clones that provide a high resolution scan of the portion of the genome of interest.

In some cases, the sensitivity of the hybridization assays is enhanced through use of a nucleic acid amplification system that multiplies the target nucleic acid being detected. Examples of such systems include the polymerase chain reaction (PCR) system and the ligase chain reaction (LCR) system. Other suitable methods include are the nucleic acid sequence based amplification (NASBAO, Cangene, Mississauga, Ontario) and Q Beta Replicase systems. In one embodiment of the invention, the DNA copy number alterations in a genome are determined by single channel profiling, such as single nucleotide polymorphism (SNP)-CGH. Traditional CGH data consists of two channel intensity data corresponding to the two alleles. The comparison of normalized intensities between a reference and subject sample is the foundation of traditional array-CGH. Single channel profiling (such as SNP-CGH) is different in that a combination of two genotyping parameters are analyzed: normalized intensity measurement and allelic ratio. Collectively, these parameters provide a more sensitive and precise profile of chromosomal aberrations. SNP-CGH also provides genetic information (haplotypes) of the locus undergoing aberration.

In some embodiments, NanoString direct DNA and/or mRNA quantification is used to determine the copy number gain (Nat Biotechnol. 2008 March; 26(3):293-4). NanoString technology requires less DNA as compared to CGH-array, and allows precise measurement of copy number gain.

In some applications it is necessary to block the hybridization capacity of repetitive sequences. Thus, in some embodiments, tRNA, human genomic DNA, or Cot-1 DNA is used to block non-specific hybridization.

In certain embodiments, Southern blotting is used to determine the DNA copy number alterations in a genome. Methods for doing Southern blotting are known to those of skill in the art (see Current Protocols in Molecular Biology, Chapter 19, Ausubel, et al., Eds., Greene Publishing and Wiley-Interscience, New York, 1995, or Sambrook et al., Molecular Cloning: A Laboratory Manual, 2d Ed. vol. 1-3, Cold Spring Harbor Press, N Y, 1989). In such an assay, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., genomic DNA from the same or related cell, tissue, organ, etc.) provides an estimate of the relative copy number of the target nucleic acid.

In one embodiment, amplification-based assays, such as PCR, are used to determine the DNA copy number alterations in a genome. In such amplification-based assays, the genomic region where a copy number alteration occurred serves as a template in an amplification reaction. In a quantitative amplification, the amount of amplification product will be proportional to the amount of template in the original sample. Comparison to appropriate controls provides a measure of the copy number of the genomic region. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided, for example, in Innis et al. (1990) PCR Protocols, A Guide to Methods and Applications, Academic Press, Inc. N.Y.

Real time PCR can be used in the methods of the invention to determine DNA copy number alterations. (See, e.g., Gibson et al. (1996) *Genome Res.* 6:995-1001; Heid et al., (1996) *Genome Res.* 6: 986-994). Real-time PCR evaluates the level of PCR product accumulation during amplification. To measure DNA copy number, total genomic DNA is isolated from a sample. Real-time PCR can be performed, for example, using a Perkin Elmer/Applied Biosystems (Foster City, Calif) 7700 Prism instrument. Matching primers and fluorescent probes can be designed for genes of interest using, for example, the primer express program provided by Perkin Elmer/Applied Biosystems (Foster City, Calif). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif). To quantify the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-10⁶ copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR are provided, inter alia, for example, for RNA in: Gibson et al. (1996) *Genome Res.,* 10: 995-1001, and for DNA in Heid et al. (1996) *Genome Res.,* 10: 986-994.

A TaqMan-based assay also can be used to quantify a particular genomic region for DNA copy number alterations. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification.

Other suitable amplification methods include, but are not limited to ligase chain reaction (LCR) (see Wu and Wallace (1989) *Genomics* 4:560, Landegren et al. (1988) *Science* 241:1077, and Barringer et al. (1990) *Gene* 89:117), transcription amplification (Kwoh et al. (1989) *Proc. Natl. Acad. Sci. USA* 86:1173), self-sustained sequence replication (Guatelli et al. (1990) *Proc. Nat. Acad. Sci. USA* 87:1874), dot PCR, and linker adapter PCR, etc. In one embodiment, DNA sequencing is used to determine the DNA copy number alterations in a genome. Methods for DNA sequencing are known to those of skill in the art.

Pharmaceutical Compositions

In various embodiments pharmaceutical compositions comprising one or more anti-CD46 antibodies (e.g., the anti-CD46 antibodies described herein) are contemplated. In some embodiments, a pharmaceutical composition formulated for administration in a variety of unit dosage forms depending upon the route of administration. For example, unit dosage forms suitable for oral administration include powder, tablets, pills, capsules and lozenges. It is recognized that the antibodies described herein or pharmaceutical compositions comprising antibodies described herein, when administered orally, are preferably protected from digestion. This can be accomplished by a number of means known to those of skill in the art, e.g., by complexing the protein with a composition to render it resistant to acidic and enzymatic hydrolysis or by packaging the protein in an appropriately resistant carrier such as a liposome. Means of protecting proteins from digestion are well known in the art.

In various embodiments a composition, e.g., a pharmaceutical composition, containing one or a combination of anti-CD46 antibodies, or antigen-binding portion(s) thereof, or immunoconjugates thereof, formulated together with a pharmaceutically acceptable carrier are provided.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, may be coated in a material to protect the compound from the action of acids and other natural conditions that may inactivate the compound.

In certain embodiments the antibody and/or immunoconjugate can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience, and as described above.

By way of illustration, a pharmaceutically acceptable salt can be prepared for any of the antibodies and/or immunoconjugates described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent.

Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include, but are not limited to, alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate {i.e., break down into the individual entities of drug and counterion) in an aqueous environment. Preferably, the counterion is a pharmaceutically acceptable counterion.

Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the antibody and/or immunoconjugate. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

Pharmaceutical compositions comprising the antibodies described herein can be administered alone or in combination therapy, i.e., combined with other agents. For example, the combination therapy can include an antibody with at least one or more additional therapeutic agents, such as the anti-cancer agents described infra. The pharmaceutical compositions can also be administered in conjunction with radiation therapy and/or surgery.

A composition comprising the antibodies and/or immunoconjugates described herein can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see, e.g., Sustained and Controlled Release Drug Delivery Systems, J. R. Robinson, ed., Marcel Dekker, Inc., New York, 1978).

In certain embodiments administration of an anti-CD46 antibody or immunoconjugate may be facilitated by coating the antibody or immunoconjugate composition, or co-administering the antibody or immunoconjugate, a material to prevent its inactivation. For example, the compound may be administered to a subject in an appropriate carrier, for example, liposomes, or a diluent. Pharmaceutically acceptable diluents include, but are not limited to, saline and aqueous buffer solutions. Liposomes include, but are not limited to, water-in-oil-in-water CGF emulsions as well as conventional liposomes (Strejan et al. (1984) *J. Neuroimmunol*, 7: 27).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of is contemplated. Supplementary active compounds can also be incorporated into the compositions.

In various embodiments the therapeutic compositions are typically sterile and stable under the conditions of manufacture and storage. The composition(s) can be formulated as a solution, a microemulsion, in a lipid or liposome, or other ordered structure suitable to contain high drug concentration(s). In certain embodiments the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound (e.g., antibodies and/or immunoconjugates described herein) in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, illustrative methods of preparation include vacuum drying, and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, in certain embodiments, the antibodies and/or immunoconjugates described herein may be administered once or twice daily, or once or twice weekly, or once or twice monthly by subcutaneous injection.

In certain embodiments it is advantageous to formulate parenteral compositions in unit dosage form for ease of administration and uniformity of dosage. Unit dosage form as used herein refers to physically discrete units suited as unitary dosages for the subjects to be treated. Each unit contains a predetermined quantity of active compound calculated to produce the desired therapeutic effect in association with the required pharmaceutical carrier. The specifications for the unit dosage forms are dictated by and directly dependent on (a) the unique characteristics of the active compound and the particular therapeutic effect to be achieved, and (b) the limitations inherent in the art of compounding such an active compound for the treatment of individuals.

In certain embodiments the formulation comprises a pharmaceutically antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the antibodies and/or immunoconjugates described herein include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient that can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of antibodies and/or immunoconjugates described herein that are suitable for vaginal administration also include pessaries, tampons, creams, gels, pastes, foams or spray formulations containing such carriers as are known in the art to be appropriate. Dosage forms for the topical or transdermal administration of antibodies and/or immunoconjugates described herein include powders, sprays, ointments, pastes, creams, lotions, gels, solutions, patches and inhalants. In certain embodiments the active compound may be mixed under sterile conditions with a pharmaceutically acceptable carrier, and with any preservatives, buffers, or propellants that may be required.

The phrases "parenteral administration" and "administered parenterally" as used herein means modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion.

Examples of suitable aqueous and nonaqueous carriers that may be employed in the pharmaceutical compositions comprising antibodies and/or immunoconjugates described herein include, but are not limited to water, ethanol, polyols (such as glycerol, propylene glycol, polyethylene glycol, and the like), and suitable mixtures thereof, vegetable oils, such as olive oil, and injectable organic esters, such as ethyl oleate, and the like. Proper fluidity can be maintained, for example, by the use of coating materials, such as lecithin, by the maintenance of the required particle size in the case of dispersions, and by the use of surfactants.

In various embodiments these compositions may also contain adjuvants such as preservatives, wetting agents, emulsifying agents and dispersing agents. Particular examples of adjuvants that are well-known in the art include, for example, inorganic adjuvants (such as aluminum salts, e.g., aluminum phosphate and aluminum hydroxide), organic adjuvants (e.g., squalene), oil-based adjuvants, virosomes {e.g., virosomes that contain a membrane-bound hemagglutinin and neuraminidase derived from the influenza virus).

Prevention of presence of microorganisms in formulations may be ensured both by sterilization procedures, and/or by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In certain embodiments, when the antibodies and/or immunoconjugates described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the antibodies and/or immunoconjugates described herein, that may be used in a suitable hydrated form, and/or the pharmaceutical compositions, are formulated into pharmaceutically acceptable dosage forms by conventional methods known to those of skill in the art.

Actual dosage levels of the active ingredients (e.g., antibodies and/or immunoconjugates described herein) in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of antibodies and/or immunoconjugates described herein will be that amount of the compound which is the lowest dose effective to produce a therapeutic effect. Such an effective dose will generally depend upon the factors described above. In certain embodiments, it is preferred that administration be intravenous, intramuscular, intraperitoneal, or subcutaneous, preferably administered proximal to the site of the target. If desired, the effective daily dose of a therapeutic composition may be administered a single dosage, or as two, three, four, five, six or more sub-doses administered separately at appropriate intervals throughout the day, optionally, in unit dosage forms. While it is possible for antibodies and/or immunoconjugates described herein to be administered alone, it is typically preferable to administer the compound(s) as a pharmaceutical formulation.

In certain embodiments the therapeutic compositions can be administered with medical devices known in the art. For example, in a illustrative embodiment, antibodies and/or immunoconjugates described herein can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of useful well-known implants and modules are described for example in U.S. Pat. No. 4,487,603, which discloses an implantable micro-infusion pump for dispensing medication at a controlled rate, in U.S. Pat. No. 4,486,194, which discloses a therapeutic device for administering medications through the skin, in U.S. Pat. No. 4,447,233, which discloses a medication infusion pump for delivering medication at a precise infusion rate, in U.S. Pat. No. 4,447,224, which discloses a variable flow implantable infusion apparatus for continuous drug delivery, in U.S. Pat. No. 4,439,196, which discloses an osmotic drug delivery system having multi-chamber compartments, and in U.S. Pat. No. 4,475,196, which discloses an osmotic drug delivery system. Many other such implants, delivery systems, and modules are known to those skilled in the art.

In certain embodiments, the anti-CD46 antibodies and/or immunoconjugates described herein can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade (1989) J. Clin. Pharmacol. 29: 685). Illustrative targeting moieties include, but are not limited to folate or biotin (see, e.g., U.S. Pat. No. 5,416,016); mannosides (Umezawa et al, (1988) Biochem. Biophys. Res. Commun. 153: 1038); antibodies (Bloeman et al. (1995) FEB'S Lett. 357: 140; Owais et al. (1995) Antimicrob. Agents Chemother. 39: 180); surfactant protein A receptor (Briscoe et al. (1995) Am. J. Physiol. 1233: 134).

Kits/Article of Manufacture

In certain embodiments kits and articles of manufacture for use with one or more methods described herein are provided. In certain embodiments such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In various embodiments the articles of manufacture provided herein can contain packaging materials. Examples of pharmaceutical packaging materials include, but are not limited to, blister packs, bottles, tubes, bags, containers, bottles, and any packaging material suitable for a selected formulation and intended mode of administration and treatment.

For example, in certain embodiments kits provide container(s) containing anti-CD46 antibodies and/or reagents for use with the anti-CD46 antibody as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In certain embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Certain Terminologies

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the disclosure.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error. In certain embodiments the term "about" means±5%, or ±4%, or ±3%, or ±2%, or ±1%, or 0.5%, or 10% of recited value.

The section headings used herein are for organizational purposes only and are not to be construed as limiting the subject matter described.

As used herein, a modification in chromosome 1q at location 21 (1q21) can comprise an amplification. In some cases, the modification at chromosome location 1q21 comprises a copy number gain. In some cases, the modification at chromosome location 1q21 comprises gains of two or more copy numbers, e.g., gains of 2, 3, 4 or more copy numbers.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" refer to at least two nucleotides covalently linked together. A nucleic acid described herein is preferably single-stranded or double stranded and generally contain phosphodiester bonds, although in some cases, as outlined below, nucleic acid analogs are included that optionally have alternate backbones, comprising, for example, phosphoramide (Beaucage et al. (1993) *Tetrahedron* 49(10):1925) and references therein; Letsinger (1970) *J Org. Chem.* 35:3800; Sprinzl et al. (1977) *Eur. J Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta.* 26: 1419), phosphorothioate (Mag et al. (1991) *Nucleic Acids Res.* 19: 1437; and U.S. Pat. No. 5,644,048), phosphorodithioate (Briu et al. (1989) *J. Am. Chem. Soc.* 111:2321, O-methylphophoroamidite linkages (see Eckstein, Oligonucleotides and Analogues: A Practical Approach, Oxford University Press), and peptide nucleic acid backbones and linkages (see Egholm (1992) *J. Am. Chem. Soc.* 114: 1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988)*J Am. Chem. Soc.* 110:4470; Letsinger et al. (1994) *Nucleoside & Nucleotide* 13: 1597; Chapters 2 and 3, ASC Symposium Series 580, "Carbohydrate Modifications in Antisense Research", Ed. Y. S. Sanghui and P. Dan Cook; Mesmaeker et al. (1994), *Bioorg. Med. Chem. Lett.* 4: 395; Jeffs et al. (1994) *J Biomol. NMR,* 34: 17; *Tetrahedron Lett.* 37:743 (1996)) and non-ribose backbones, including, but not limited to, those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids {see Jenkins et al. (1995), *Chem. Soc. Rev.* pp 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "residue" as used herein refers to a natural, synthetic, or modified amino acid.

As used herein, an "antibody" refers to a protein consisting of one or more polypeptides substantially encoded by immunoglobulin genes or fragments of immunoglobulin genes, or a polypeptide derived therefrom. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_H$1 by a disulfide bond. The F(ab)'2 may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) Proc. Nat. Acad. Sci. USA, 85: 5879-5883. While the $V_H$ and $V_L$ are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p {see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art {see e.g., U.S. Pat. Nos. 5,091,513, 5,132,405, and 4,956,778). Particularly preferred antibodies should include all that have been displayed on phage {e.g., scFv, Fv, Fab and disulfide linked Fv (Reiter et al. (1995) Protein Eng. 8: 1323-1331).

In some instances, a minibody is a chimeric molecule comprising a single chain variable domain (e.g., comprising a single chain VH and VL) fused to the hinge region and the CH3 domain of an immunoglobulin molecule.

In some embodiments, a nanobody is a single-domain antibody (sdAb) developed by Ablynx. The antibody fragment comprises of a single monomeric variable antibody domain, and in some cases comprises about 12-15 kDa. In some instances, an sdAb engineered from a heavy-chain antibody found in camelid is referred to as a $V_HH$ fragment. In other cases, an sdAb derived from an IgNAR is referred to as a $V_{NAR}$ fragment.

The term "specifically binds", as used herein, when referring to a biomolecule (e.g., protein, nucleic acid, antibody, etc.), refers to a binding reaction that is determinative of the presence biomolecule in heterogeneous population of molecules (e.g., proteins and other biology). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The phrase "inhibition of proliferation of a cell expressing CD46" as used herein, refers to the ability of an anti-CD46 antibody or immunoconjugate described herein to decrease, preferably to statistically significantly decrease proliferation of a cell expressing CD46 relative to the proliferation in the absence of the antibody or immunoconjugate. In an illustrative, but non-limiting, embodiment, the proliferation of a cell expressing CD46 (e.g., a cancer cell) is decreased by at least 10%, or at least 20%, or at least 30%, or at least 40%, or at least 50%, or at least 60%, or at least 70%, or at least 80%, or at least 90%, or 100% when the cells are contacted with the antibody or antigen binding portion thereof or an immunoconjugate described herein, relative to the proliferation measured in the absence of the antibody or antigen binding portion thereof or immunoconjugate (control). Cellular proliferation can be assayed using art recognized techniques which measure rate of cell division, the fraction of cells within a cell population undergoing cell division, and/or rate of cell loss from a cell population due to terminal differentiation or cell death (e.g., using a cell titer glow assay or thymidine incorporation).

The phrase "inhibition of the migration of cells expressing CD46" as used herein, refers to the ability of an anti-CD46 antibody or an antigen-binding portion thereof or an immunoconjugate described herein to decrease, preferably to statistically significantly decrease the migration of a cell expressing CD46 relative to the migration of the cell in the absence of the antibody. In one illustrative but non-limiting embodiment, the migration of a cell expressing CD46 (e.g., a cancer cell) may be decreased by at least 10%, or at least 20%, or at least 30%, or at least 40%), or at least 50%, or at least 60%, or at least 70%, or at least 80%, or at least 90%, or 100% when the cells are contacted with the antibody or antigen binding portion thereof or immunoconjugate thereof, relative to cell migration measured in the absence of the antibody or antigen binding portion thereof or immunoconjugate thereof (control). Cell migration can be assayed using art recognized techniques. In various embodiments, it is contemplated that the antibodies and/or the immunoconjugates thereof described herein can inhibit the migration of cells (e.g., cancer cells as described herein) expressing or overexpressing CD46.

The term "antigen-binding portion" of an antibody (or simply "antibody portion"), as used herein, refers to one or more fragments of an antibody that retain the ability to specifically bind to an antigen (e.g., CD46 domain 1 and/or domain 2). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CHI domains; (ii) a F(ab')$_2$ fragment, a bivalent fragment comprising two Fab fragments linked by a disulfide bridge at the hinge region; (iii) a Fd fragment consisting of the $V_H$ and CHI domains; (iv) a Fv fragment consisting of the $V_L$ and $V_H$ domains of a single arm of an antibody, (v) a dAb including VH and VL domains; (vi) a dAb fragment (see, e.g., Ward et al. (1989) Nature 341: 544-546), which consists of a $V_H$ domain; (vii) a dAb which consists of a $V_H$ or a $V_L$ domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, can be coded for by separate genes, they can be joined, using recombinant methods, by a synthetic linker that enables them to be made as a single protein chain in which the $V_L$ and V-regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al. (1975) Nature, 256: 495, a transgenic animal, as described by, for example, (see e.g., Lonberg, et al. (1994) Nature 368(6474): 856-859), recombinant DNA methods (see, e.g., U.S. Pat. No. 4,816,567), or using phage antibody libraries using the techniques described in, for example, Clackson et al. (1991) Nature, 352: 624-628, and Marks et al. (1991) J. Mol. Biol, 222: 581-597. Monoclonal antibodies include chimeric antibodies, human antibodies and humanized antibodies and may occur naturally or be recombinantly produced.

The term "recombinant antibody" refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and VL regions of the recombinant antibodies are sequences that, while derived from and related to human germline $V_H$ and VL sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody", as used herein, is intended to include antibodies having variable regions in which both the framework and CDR regions are derived from human germline immunoglobulin sequences as described, for example, by Kabat et al. (See Kabat, et al. (1991) Sequences of proteins of Immunological Interest, Fifth Edition, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue which is not encoded by the human germline immunoglobulin sequence. Typically, the human antibody can have up to twenty positions replaced with amino acid residues which are not part of the human germline immunoglobulin sequence. In a particular embodiment, these replacements are within the CDR regions as described in detail below.

In some instances, "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

As used herein, a "heterologous antibody" is defined in relation to the transgenic non-human organism or plant producing such an antibody.

In some embodiments, an "isolated antibody" refers to an antibody that is substantially free of other antibodies having different antigenic specificities (e.g., an isolated antibody that specifically binds to CD46 is substantially free of antibodies that specifically bind antigens other than CD46). In addition, an isolated antibody is typically substantially free of other cellular material and/or chemicals. In one embodiment, a combination of "isolated" monoclonal antibodies having different CD46 binding specificities are combined in a well-defined composition.

As used herein, "isotype" refers to the antibody class (e.g., IgM or IgG1) that is encoded by heavy chain constant region genes. In one embodiment, an antibody or antigen binding portion thereof is of an isotype selected from an IgG1, an IgG2, an IgG3, an IgG4, an IgM, an IgA1, an IgA2, an IgAsec, an IgD, or an IgE antibody isotype. In some embodiments, a monoclonal antibody of the invention is of the IgG1 isotype. In other embodiments, a monoclonal antibody of the invention is of the IgG2 isotype.

An "antigen" is an entity (e.g., a proteinaceous entity or peptide) to which an antibody or antigen-binding portion thereof binds. In various embodiments of the present invention, an antigen is CD46, e.g., as presented on a cell (e.g., a CD46 positive cancer cell).

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

Also contemplated herein are antibodies that bind the same or an overlapping epitope as one or more of the YS5, YS5F, YS5vlD, SBIHGNY, YS12, 3G7RY (aka 3G8), YS6, YS1, YS3, YS4, YS8, YS7, YS9, YS10, YS1 1, 3G7HY, 3G7NY, 3G7, SB2, 2C8, and/or UA8kappa antibodies described herein. Antibodies that recognize the same epitope can be identified using routine techniques such as an immunoassay, for example, by showing the ability of one antibody to block the binding of another antibody to a target antigen, i.e., a competitive binding assay. Competitive binding is determined in an assay in which the immunoglobulin under test inhibits specific binding of a reference antibody to a common antigen, such as CD46 domain 1 and/or domain 2. Numerous types of competitive binding assays are known, for example: solid phase direct or indirect radioimmunoassay (RIA), solid phase direct or indirect enzyme immunoassay (EIA), sandwich competition assay (see, e.g., Stahli et al. (1983)*Meth. Enzymol,* 9: 242); solid phase direct biotin-avidin EIA (see Kirkland et al, (1986) *J Immunol.* 137: 3614); solid phase direct labeled assay, solid phase direct labeled sandwich assay (see, e.g., Harlow and Lane (1988) Antibodies: A Laboratory Manual, Cold Spring Harbor Press); solid phase direct label RIA using, e.g., $^{125}$I label (see, e.g., Morel et al, (1988) *Mol. Immunol.* 25(1): 7); solid phase direct biotin-avidin EIA (Cheung et al. (1990) *Virology* 176: 546); and direct labeled RIA. (Moldenhauer et al. (1990) *Scand J. Immunol.* 32: 77). Typically, such an assay involves the use of purified antigen (e.g., CD46 domain 1 and/or domain 2) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

As used herein, the terms "specific binding," "specifically binds," "selective binding," and "selectively binds," mean that an antibody or antigen-binding portion thereof, exhibits appreciable affinity for a particular antigen or epitope and, generally, does not exhibit significant cross-reactivity with other antigens and epitopes. "Appreciable" or preferred binding includes binding with an affinity of at least (KD equal to or less than) $10^{-6}$ M, $10^{-7}$ M, $10^{-8}$ M, $10^{-9}$ M, $10^{-10}$ M, or $10^{-11}$ M. Affinities greater than 10-9 M, preferably greater than $10^{-10}$ M are more preferred. Values intermediate of those set forth herein are also intended to be within the scope of the present invention and a preferred binding affinity can be indicated as a range of affinities, for example, $10^{-6}$ M to $10^{-11}$ M, preferably $10^{-7}$ M or $10^{-8}$ M to $10^{-10}$ M. In some instances, an antibody that does not exhibit significant cross-reactivity is one that will not appreciably bind to an undesirable entity (e.g., an undesirable proteinaceous entity). For example, in one embodiment, an antibody or antigen-binding portion thereof that specifically binds to CD46 (e.g., domain 1 and/or domain 2) protein but will not significantly react with other molecules and non-CD46 proteins or peptides. Specific or selective binding can be determined according to any art-recognized means for determining such binding, including, for example, according to Scatchard analysis and/or competitive binding assays.

The term "$K_D$" refers to the dissociation equilibrium constant of a particular antibody-antigen interaction or the affinity of an antibody for an antigen. In one embodiment, the antibody or antigen binding portion thereof according to the present invention binds an antigen (e.g., CD46 domain 1 and/or domain 2) with an affinity ($K_D$) of 5 nM or better (i.e., or less) (e.g., 40 nM or 30 nM or 20 nM or 10 nM or less), as measured using a surface plasmon resonance assay or a cell binding assay. In a particular embodiment, an antibody or antigen binding portion thereof according to the present invention binds CD46 with an affinity ($K_D$) of 5 nM or better (e.g., 4 nM, 2 nM, 1.5 nM, 1.4 nM, 1.3 nM, 1 nM, or less), as measured by a surface plasmon resonance assay or a cell binding assay. In other embodiments, an antibody or antigen binding portion thereof binds an antigen (e.g., CD46) with an affinity ($K_D$) of approximately less than $10^{-10}$ M, or $100 \times 10^{-11}$ M, or $10 \times 10^{-11}$ M, or even lower using live prostate tumor cells by FACS.

$K_{off}$ refers to the off rate constant for the dissociation of an antibody from the antibody/antigen complex.

$EC_{50}$ refers to the concentration of an antibody or an antigen-binding portion thereof or an immunoconjugate described herein, that induces a response, either in an in vitro or an in vivo assay, which is 50% of the maximal response, i.e., halfway between the maximal response and the baseline.

The term "naturally-occurring" as used herein as applied to, e.g., an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

In some cases, the term "modifying" or "modification" refer to changing one or more amino acids in the antibodies or antigen-binding portions thereof. The change can be produced by adding, substituting or deleting an amino acid at one or more positions. The change can be produced using known techniques, such as PCR mutagenesis. For example, in some embodiments, an antibody or an antigen-binding portion thereof identified using the methods of the invention can be modified, to thereby modify the binding affinity of the antibody or antigen-binding portion thereof to CD46.

In certain embodiments, "conservative amino acid substitutions" in the sequences of the anti-CD46 antibodies described herein, i.e., nucleotide and amino acid sequence modifications that do not abrogate the binding of the antibody encoded by the nucleotide sequence or containing the amino acid sequence, to the antigen, e.g., CD46 are contemplated. Conservative amino acid substitutions include the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gin, Glu); Class IV (His, Arg, Lys); Class V (He, Leu, Val, Met); and Class VI (Phe, Tyr, Trp). For example, substitution of an Asp for another class III residue such as Asn, Gin, or Glu, is a conservative substitution. Thus, a predicted nonessential amino acid residue in an anti-CD46 antibody is preferably replaced with another amino acid residue from the same class. Methods of identifying nucleotide and amino acid conservative substitutions that do not eliminate antigen binding are well-known in the art (see, e.g., Brummell et al. (1993) *Biochem.* 32: 1180-1187; Kobayashi et al. (1999) *Protein Eng.* 12(10): 879-884; and Burks et al. (1997) *Proc. Natl. Acad. Sci. USA* 94: 412-417).

The term "non-conservative amino acid substitution" refers to the substitution of an amino acid in one class with an amino acid from another class; for example, substitution of an Ala, a class II residue, with a class III residue such as Asp, Asn, Glu, or Gln.

In another embodiment, mutations (conservative or non-conservative) can be introduced randomly along all or part of an anti-CD46 antibody coding sequence, such as by saturation mutagenesis, and the resulting modified antibodies can be screened for binding activity.

A "consensus sequence" is a sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

Similarly, the consensus sequence for the CDRs of can be derived by optimal alignment of the CDR amino acid sequences of anti-CD46 antibodies described herein.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software, using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of Meyers and Miller (1989) CABIOS, 4: 11-17, which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48: 444-453 algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid compositions described herein (e.g., nucleic acids encoding all or a portion of an anti-CD46 antibody or immunoconjugate) while often in a native sequence (except for modified restriction sites and the like), from either cDNA, genomic or mixtures thereof may be mutated, in accordance with standard techniques to provide variant sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms, "plasmid" and "vector" may be used interchangeably. However, the invention is intended to include such other forms of expression vectors, such as viral vectors (e.g., replication defective retroviruses, adenoviruses and adeno-associated viruses), that serve equivalent functions.

The term "recombinant host cell" (or simply "host cell"), as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject (e.g., a subject in need thereof), an anti-CD46 antibody or antigen binding portion or an immunoconjugate comprising such an antibody or antigen binding portion described herein. In certain embodiments the subject is a subject diagnosed with and/or under treatment for a CD46 positive cancer (e.g., prostate cancer) in order to prevent, cure, delay, reduce the severity of, or ameliorate one or more symptoms of the disease or disorder or recurring disease or disorder, or in order to prolong the survival of a subject beyond that expected in the absence of such treatment.

The terms "cancer" and "cancerous" refer to or describe the physiological condition in mammals that is typically characterized by unregulated cell growth. A CD46 positive cancer refers to a cancer characterized by cells that express or overexpress CD46. Illustrative CD46 cancers include, but are not limited to, ovarian cancer, breast cancer, lung cancer, prostate cancer, colon cancer, kidney cancer, and pancreatic cancer.

The term "effective amount," as used herein, refers to that amount of an anti-CD46 antibody or an antigen binding portion thereof and/or an immunoconjugate thereof, that is sufficient to effect treatment, prognosis or diagnosis of a disease associated with the growth and/or proliferation of CD46 positive cells (e.g., a CD46 positive cancer), as described herein, when administered to a subject. A therapeutically effective amount will vary depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 µg to about 3,500 mg, about 5 µg to about 3,000 mg, about 10 µg to about 2,600 mg, about 20 µg to about 2,575 mg, about 30 µg to about 2,550 mg, about 40 µg to about 2,500 mg, about 50 µg to about 2,475 mg, about 100 µg to about 2,450 mg, about 200 µg to about 2,425 mg, about 300 µg to about 2,000, about 400 µg to about 1,175 mg, about 500 µg to about 1,150 mg, about 0.5 mg to about 1, 125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an anti-CD46 antibody described herein and/or antigen binding portion thereof, and/or immunoconjugate thereof as described herein. Dosage regiments may be adjusted to provide the optimum therapeutic response. An effective amount is also one in which any toxic or detrimental effects (i.e., side effects) of an antibody or antigen binding portion thereof are minimized and/or outweighed by the beneficial effects.

The term "patient" includes human and other mammalian subjects that receive either prophylactic or therapeutic treatment.

As used herein, the term "subject" includes any human or non-human animal. For example, the methods and compositions of the present invention can be used to treat a subject having cancer. In a particular embodiment, the subject is a human. The term "non-human animal" includes all vertebrates, e.g., mammals and non-mammals, such as non-human primates, sheep, dog, cow, chickens, amphibians, reptiles, etc.

The phrase "inhibiting the growth and/or proliferation", e.g. of cancer cells includes inter alia inducing cellular apoptosis or other cell killing mechanisms, reducing the invasiveness of the cells, stalling the cells at a point in the cell cycle, and the like.

The term "immunoconjugate" refers to an antibody attached to one or more payloads or to a plurality of antibodies attached to one or more payloads. The term "immunoconjugate" is intended to include payloads chemically conjugated to the antibodies as well as antibodies expresses as a fusion protein where the antibody (or a portion thereof) is directly attached or attached through a linker to a peptide payload or to a payload comprising a peptide.

EXAMPLES

The following examples are offered to illustrate, but not to limit the claimed invention.

Example 1

The treatment of multiple myeloma (MM) has improved in recent years with FDA approval of agents in the immunomodulatory drug (IMiD) and proteasome inhibitor drug classes. Nevertheless, myeloma in some cases remains incurable and patients inevitably develop treatment-refractory disease. In addition, high-risk cytogenetic subgroups, including those with deletion of chromosome 17p or gain of chromosome 1q21, progress more rapidly through approved agents and have shortened overall survival.

In some instances, a correlation is observed between CD46 overexpression and amplification at chromosome location 1q21. In such cases, 1q21 can be used as a marker for translation of CD46-targeting agents in treatment of cancers such as multiple myeloma.

MM Patient and Normal Donor Samples

Bone marrow (BM) samples from multiple myeloma (MM) patient samples #1-10 were separated into two fractions based on selection for CD138 expression with EasySep magnetic bead columns (Stem Cell Technologies). Primary cells were cultured in RPMI1640 media with 100 units/ml penicillin, 100 µg/ml streptomycin, 10% fetal bovine serum and 2 ng/ml IL-6. BM and PB controls from normal donors were purchased from AllCells.

Antibody Generation

A combined phage and yeast antibody display library selection approach was used to identify anti-CD46 human antibodies. Briefly, the human CD46 gene fragment containing domains 1 and 2 was cloned into the pFUSE-Fc vector (Invivogen) to create a recombinant Fc fusion molecule that was produced in HEK293a cells, and purified by protein A affinity chromatography. A nonimmune phage antibody display library containing one billion members was incubated with CD46-Fc fusion coated on polystyrene beads in PBS/2% dry milk at room temperature for 1 hour, followed by wash 3× with PBS/2% dry milk, elution with 100 mM triethylamine, and neutralization with 1M Tris-HCl, pH 6.8. Following three rounds of selection, binding phage were screened by FACS on Du145 cells and sequenced. Unique phage antibodies were re-tested on recombinant CD46-Fc fusion coated microtiter plates to confirm binding specificity. In parallel, an alternative strategy was employed by selecting the phage antibody library on live tumor cells, followed by transferring the output into a yeast surface display vector, and then FACS-based selection using low concentration ligands to enrich high affinity binders to the recombinant CD46-Fc fusion protein. A panel of novel anti-CD46 antibodies was identified and further studied for internalization and macropinocytosing activities and the YS5 antibody was chosen for ADC development. Full-length human YS5 IgG1 was constructed from phage antibody sequence, produced in HEK293a and purified by protein A chromatography. Affinity of YS5 IgG1 to recombinant CD46-Fc (domains 1 and 2) was measured by the label free BLItz system (ForteBio) with the biosensor coated with the YS5 antibody. Affinity to living myeloma cells was measured by FACS on RPMI8226 and MM1.S cell lines with MFI values curve-fit using one-site specific binding model (GraphPad). A control IgG1 (YSC10) was created from a phage antibody picked randomly from the nonselected library, which does not bind to any cell surface antigen and hence is designated as a non-binding antibody herewith.

MM Cell Lines

MM cell lines bearing the firefly luciferase reporter gene were a kindly provided by Dr. Constantine Mitsiades, Dana-Farber Cancer Institute, Boston, Massachusetts. RPMI8226, MM1.S and MM1.R were purchased from American Type Culture Collection (ATCC). All MM cell lines were maintained in RPMI1640 with 100 units/ml penicillin, 100 µg/ml streptomycin and 10% fetal bovine serum. INA-6 was supplemented with IL-6 (2 ng/ml). Patient stromal culture, BM61, was derived from CD138-negative MNC fractions derived from BM aspirate.

FACS Analysis of Cell Surface CD46 Expression

To determine CD46 expression on MM cells, FACS was performed using biotin labeled human anti-CD46 IgG1 followed by detection with Alexa Fluor 647-conjugated streptavidin (Life Technologies). All samples were analyzed using Accuri C6 with a 96-well auto-sampler. Nonspecific Fc receptor binding was minimized by pre-incubation with Clear Back reagent (MBL). To determine CD46 expression on patient samples, multi-color analysis was performed using Fluorescein isothiocyanate (FITC)-conjugated anti-CD38 antibody (clone AT1, Stem Cell Technologies) to identify MM cells in CD138-selected samples. For FACS of CD46 on various BM and PB cell populations, an extended antibody panel was used with anti-CD38 (clone HIT2) PerCP-Cy5.5, anti-CD138 (clone MI15) BV421, anti-CD45 (clone H130) BV510, anti-CD19 (clone HIB19) BB515, anti-CD4 (clone RPA-T4) PerCP-Cy5.5, anti-CD8 (clone RPA-T8) Pacific Blue, anti-CD3 (clone HIT3a) FITC, anti-Lineage FITC, anti-CD34 (clone 581) PE, anti-CD61 (clone VI-PL2) PE, anti-CD33 (clone HIM3-4) FITC, anti-CD14 (clone Hop9) PerCP-Cy5.5 (BD Biosciences) and Live/Dead-Near IR (Life Technologies/Thermal Fisher) on a FACSCanto II (Becton, Dickinson) flow cytometer.

Cell Surface Antigen Density Determination

Quantitative flow cytometry was performed to determine CD46 antigen density. Anti-CD46 and anti-CD38 antibodies were labeled with Alexa Fluor 647 (Molecular Probes/Life Technologies) according to manufacturer's recommendations. MFI conversion to MESF was done by generating a standard curve with Quantum™ beads (Bangs Labs). The fluorophore-to antibody ratio of the labeled antibodies was determined using Simply Cellular® anti-Human (for CD46) or anti-mouse (for CD38) IgG beads (Bangs Labs). Finally, conversion of MESF to cell surface antigen density was done by division of the fluorophore-to-antibody ratio.

Antigen Shedding

To assay for CD46 antigen shed into cell culture media, $4 \times 10^5$ RPM18226 cells were seeded in a 6-well plate (Falcon) and cultured in a CO2 incubator at 37° C. overnight. Next, 5 ml serum-free culture medium containing 10 µg/ml anti-CD46 antibody or nonbinding control antibody were added for additional 24 hour-incubation. The cells were separated by centrifuged at 1,500 rpm for 10 minutes, and lysed with cell lysis buffer (20 mM Tris-HCl, pH 7.4, 0.3 M NaCl, 1% Nonidet P-40) supplemented with complete protease inhibitor cocktail (Roche). The supernatants were concentrated 50× by centrifuging in a Centricon filter unit (Millipore) at 4,000 rpm for 30 minutes at 4° C. Samples were boiled in SDS sample buffer and analyzed by SDS-PAGE gel electrophoresis. After semi-dry transfer to Immobilon-P membrane (Millipore), Western blotting was performed using anti-CD46 antibody H-294 (sc-9098, Santa Cruz Biotechnology) followed by anti-rabbit HRP (Jackson ImmunoResearch Laboratories) and detected by chemiluminescence with Pierce ECL Western Blotting Substrate (Pierce/Thermo Fisher Scientific) according to manufacturer's instructions. Images were captured using a C-DiGit blot scanner (LI-COR Biosciences).

Antibody Internalization by Confocal Microscopy

Alexa Fluor 647-labeled anti-CD46 antibody was incubated with MM cell lines for 4 or 18 hours, washed with PBS, fixed with 4% PFA, permeabilized with PBS with 0.1% Triton X-100 and 1% Bovine serum albumin, and analyzed by confocal microscopy (Olympus FluoView). Nonbinding isotype antibody was studied in parallel as a control. For internalization by patient cells ex vivo, CD138-positive and CD138-negative (control) cells were incubated with Alexa Fluor 647-labeled anti-CD46 or nonbinding isotype control antibodies for 18 hours, processed and analyzed as described above. Subcellular localization to lysosomes was assessed by co-staining with LAMP1 antibody (clone D2D11, Cell Signaling Technology).

ADC Generation and Characterization

MMAF was conjugated to anti-CD46 IgG1 via a mcvcpab linker. To create the mcvcpab linker, N-ε-maleimidocaproyloxysuccinimide ester (Pierce) was dissolved in anhydrous dimethylformamide (DMF) (final 0.14 mM). This solution was then added to valine-citrullinepaminobenzylalcohol (Concortis Biosystems) (final 0.14 mM). After briefly agitating to dissolve all components, diisopropylethylamine (DIPEA) was added (final 0.41 mmol), incubated at room temperature for 1 hour, and precipitated with cold ethyl acetate (EtOAc) to form mcvcpab. Bisnitrophenyl carbonate (0.41 mmol) was added along with DIPEA (0.41 mmol) to mcvcpab dissolved in DMF and incubated at room temperature for 4 hours followed by EtOAc precipitation as before to yield maleimidocaproyl-valine-citrulline-p-aminobenzyl-alcohol pnitrophenol carbonate (mcvcpab-PNP). MMAF hydrochloride salt (Concortis Biosystems), Nhydroxysuccinimide, and DIPEA were added to DMF-dissolved mcvcpab-PNP and incubated at room temperature for 16 hours to form mcvcpabMMAF. CD46 IgG1 was reduced by tris(2-carboxyethyl)phosphine (TCEP) at 37° C. for 2h, purified by Zeba spin column (Pierce/Fisher), buffer-exchanged into PBS with 5 mM EDTA and incubated with linker-conjugated MMAF (mcvcpabMMAF) at room temperature for 1 hour. Conjugation products were purified by running twice though the spin column to remove free MMAF and analyzed by HPLC using HIC with Infinity 1220 LC System (Agilent). The drug to antibody ratio is estimated from area integration using the OpenLab CDS software (Agilent).

Apoptosis Assay

Induction of apoptosis and cell death in myeloma cell lines was evaluated using an Annexin VFITC Early Apoptosis Detection Kit (Cell Signaling). Cell lines were seeded into 96-well plates at $4 \times 10^4$ cells/well, incubated with varying concentrations of CD46-ADC or nonbinding control ADC at 37° C. for 48 hours. Apoptosis and cell death were assessed in triplicate by FACS for Annexin V-FITC and PI. For primary samples, induction of apoptosis and cell death was also studied using the above approach, with the following modifications. Magnetic bead column separated CD138-positive and -negative cell fractions were each plated at $4 \times 10^4$ cells/well and incubated with CD46-ADC or nonbinding ADC at 37° C. After 48 hours, cells were analyzed by FACS using Annexin V-FITC, PI and CD38 (AT1, Santa Cruz). Annexin-V and PI staining were gated separately for the CD138-positive, CD38-positive MM cells and the CD138-negative, CD38-negative NPCs.

Cell Proliferation Assays

The firefly luciferase reporter-expressing lines were used to determine ADC potency in vitro. Cells were plated into 96-well plates at 2,000/well and incubated for 96 hours with CD46-ADC. Following administration of luciferin, firefly luciferase activity was measured as an indicator of viability using a BioTek Synergy 2. The data were normalized against untreated control wells and EC50 estimated using GraphPad Prism v6.0c. For assessment of patient cell sensitivity to ADC, unselected MNC samples were plated at $4\times10^4$ cells/well in 96-well plates and treated with CD46-ADC or nonbinding ADC at 37° C. for 48 hours. Cells were harvested post-treatment, washed and stained with phycoerythrin-conjugated anti-CD138 (BD Biosciences) and FITC-conjugated anti-CD38 antibodies. The number of CD138-positive, CD38-positive MM cells and CD138-negative, CD38-negative NPC were gated and counted, with the curve constructed following normalization to the cell numbers in untreated wells. Treatments were performed in triplicate and plotted with SEM.

Bone Marrow Stromal Cell Co-Culture and Conditioned Media

BM co-culture experiments evaluating ADC activity in MM1.S cells were performed using Compartment-Specific Bioluminescence. Following ACK lysis, CD138-positive cells were isolated from MNCs using the EasySep Human Whole Blood and BM CD138 Positive Selection Kit (Stem Cell Technologies). HS5 and HS27A were purchased from ATCC. BM61 cells were generated from culture of CD138-negative BM MNCs from a myeloma patient sample. HS5, HS27A, or BM61 were grown in RPMI1640 supported cultures for later use in mono-culture or co-culture assays. Co-culture assays were initiated using a 2:1 ratio of BMSC to MM cells.

CD46 gene expression of MM cells in co-culture were evaluated as follows: MM1.S cells were seeded in monoculture at a density of $5\times10^5$ cells/mL, or, for co-culture, seeded at the same density over 70% confluent stromal cells. After 24 hours, cells were collected and treated with trypsin-free dissociation solution (Accumax) and CD138+ magnetic bead separation (Miltenyi) was used to isolate MM1.S cells. FACS for mCherry expression verified <5% contamination by stromal cells (that do not carry the mCherry gene). mRNA-seq was performed on MM1.S cells as previously described (57), and sequenced on an Illumina HiSeq 2500. Normalized sequencing reads, in Fragments Per Kilobase per Million mapped reads (FPKM), mapping to CD46 canonical transcript sequence were measured.

BM stromal cell conditioned media was collected from HS5 cells cultured under serum free conditions for 48 hours. MM1.S and MM1.R cell CD46 and CD38 antigen density was measured with or without the addition of conditioned media for 72 hours.

CD46 Knockdown

CD46 was targeted for knockdown with shRNA oligo with sequence 5-ATTGGAGAGAGCACGATTTAT-3 (SEQ ID NO:76). The shRNA sequence was cloned into pLKO.1-GFP vector, containing a U6 promoter to drive shRNA expression and an IRES-GFP. Lentivirus particles were produced in HEK293T cells by co-transfecting shRNA constructs with pPax2 and pMD2.G. H929 MM cell lines were incubated with lentivirus and assessed for infection by GFP expression and CD46 knockdown by FACS 7 days post-infection.

In Vivo Animal Study

For in vivo efficacy assessment of CD46-ADC, $5\times10^5$ RPIM8226-Luc or MM1.S-Luc cells were injected intravenously (i.v.) into NSG mice (4-6 weeks of age, male and female) (Jackson Laboratory) to create orthometastatic MM xenograft models. Bioluminescence imaging (BLI) was used to monitor graft status (typically injected tumor cells established themselves in the bone marrow and joint in 10 days). Four mouse groups were treated with CD46-ADC, control ADC (MMAF-conjugated to a non-binding human IgG1), naked anti-CD46 antibody, or vehicle control (PBS). Tumor status was assessed by BLI and results analyzed by Living Image (PerkinElmer). Following treatment, mice were continuously monitored for survival endpoints over a period >200 days. HR was determined by log-rank method and significance by Wilcoxon test. For tolerability assessment, transgenic mice expressing human CD46 under its native promoter were used (created in strain C57BL 6, backcrossed into C57BL 6 background for over eight generations).

The following primers were used for genetic screening: hMCPTg1 (5' ATTGTTGCGTCCCATATCT 3', SEQ ID NO:77) and hMCPTg2 (5' CGGAGAAGGAGTACAGC 3', SEQ ID NO:78). Eight weeks old male mice were used in the study. Both the CD46-ADC and the YSC10 non-binding control ADC were tested. Animals were injected i.v. bolus of the testing agent at 6 mg/kg (n=3) and monitored for body weight loss and other overt signs of stress for 14 days. At the end of the experiment, major organs were harvested, formalin-fixed, frozen in liquid nitrogen, cryosectioned by Cryostat (Leica Biosystems), and stained with hematoxylin and eosin (ScyTek laboratories). To assess the status of CD20-positive region in the spleen, the spleen sections were stained with goat anti-mouse CD20 antibody (clone M-20, Santa Cruz Biotechnologies), and measured diameters of the CD20 positive regions following treatment (n=74 for CD46-ADC treated and 81 for control ADC-treated regions, respectively). P value was calculated by two tailed Student's t test.

Data Mining:

CD46 mRNA expression and copy number data was mined from three published datasets (Zhan F et al. Global gene expression profiling of multiple myeloma, monoclonal gammopathy of undetermined significance, and normal bone marrow plasma cells. *Blood* 2002; 99(5):1745-1757; Zhan F et al. Gene-expression signature of benign monoclonal gammopathy evident in multiple myeloma is linked to good prognosis. *Blood* 2007; 109(4):1692-1700; and Agnelli L et al. A SNP microarray and FISH-based procedure to detect allelic imbalances in multiple myeloma: an integrated genomics approach reveals a wide gene dosage effect. *Genes. Chromosomes Cancer* 2009; 48(7):603-614). mRNA expression data was downloaded as Log 2 median intensities and Log 2 copy number from public Oncomine microarray datasets (https://www.oncomine.org) and analyzed for fold increase using GraphPad Prism v6.0c. Mean intensities and copy number for cohorts in each dataset were analyzed for significance by two-tailed Student's t test or by one-way ANOVA analyses with Bonferroni's multiple comparisons test.

Data from the CoMMpass StudySM (Interim Analysis 6) were kindly provided by the Multiple Myeloma Research Foundation. Normalized copy number data for 322 patients' tumor DNA was annotated as being amplified where the log 2 ratio of tumor/normal segmented copy number exceeded 0.3. Copy number values were summarized in FIG. 14A by dividing chromosome one into 1,000 equally-sized windows and reporting the maximum segmented copy number call within that window. Pearson's correlation was reported. Fractional frequency of co-amplification with MCL1-containing window was calculated for windows along chromosome 1 for each sample.

Correlations between log 2 copy number values for CD46, MCL1, CKS1B, and CCND1 were conducted using GraphPad Prism v6.0c, with log 2 values of >0.3 denoting copy gain for all loci analyzed. Linear regressions and 95% confidence intervals were also plotted. CD46 expression was analyzed for a subset of 260 patient samples for which both RNA-seq and Array-CGH data were available. CD46 expression is quantified as FPKM. Mean CD46 FPKM values ±95% CI were plotted and analyzed for the whole population (260 patients), as well as for cohorts defined as CD46 or MCL1 copy number gain (log 2 copy number greater than 0.3 for each loci) or no gain (log 2 copy number less than 0.3 for each loci). CD46 FPKM values for each cohort were compared for significance by one-way ANOVA, using Tukey's multiple comparison correction using GraphPad Prism v6.0c.

Statistics

All data were presented as mean and SEM unless noted. Significance was determined using Graphpad Prism v6.0c. Two-tailed Student's t-test was used when comparing 2 means. When comparing multiple groups, ANOVA was used with multiple comparison correction. Levels of significance are categorized as $*p<0.05$, $p<0.01$, $*p<0.001$ and $****p<0.0001$. Mouse model sample sizes were determined by preliminary in vivo experience with CD46-ADC and other ADCs published in the literature, rather than power calculation, and statistically significant results were observed.

Study Approval

BM samples from MM patients were obtained from the University of California, San Francisco and University of Colorado Anschutz Medical Campus hematologic malignancies tissue banks with approval from the UCSF and Western Institutional Review Boards, respectively. Informed consent was obtained from all who donated samples. Identifying patient information was replaced with sequentially assigned numbers, in accordance with HIPAA (Health Insurance Portability and Accountability Act) guidelines. Mouse studies were approved by the UCSF Animal Care and Use Committee (AN092211-01) and Washington University in St. Louis Animal Studies Committee (20100272A1).

CD46 Antigen is Highly Expressed in Myeloma Cell Lines

Figure 1:
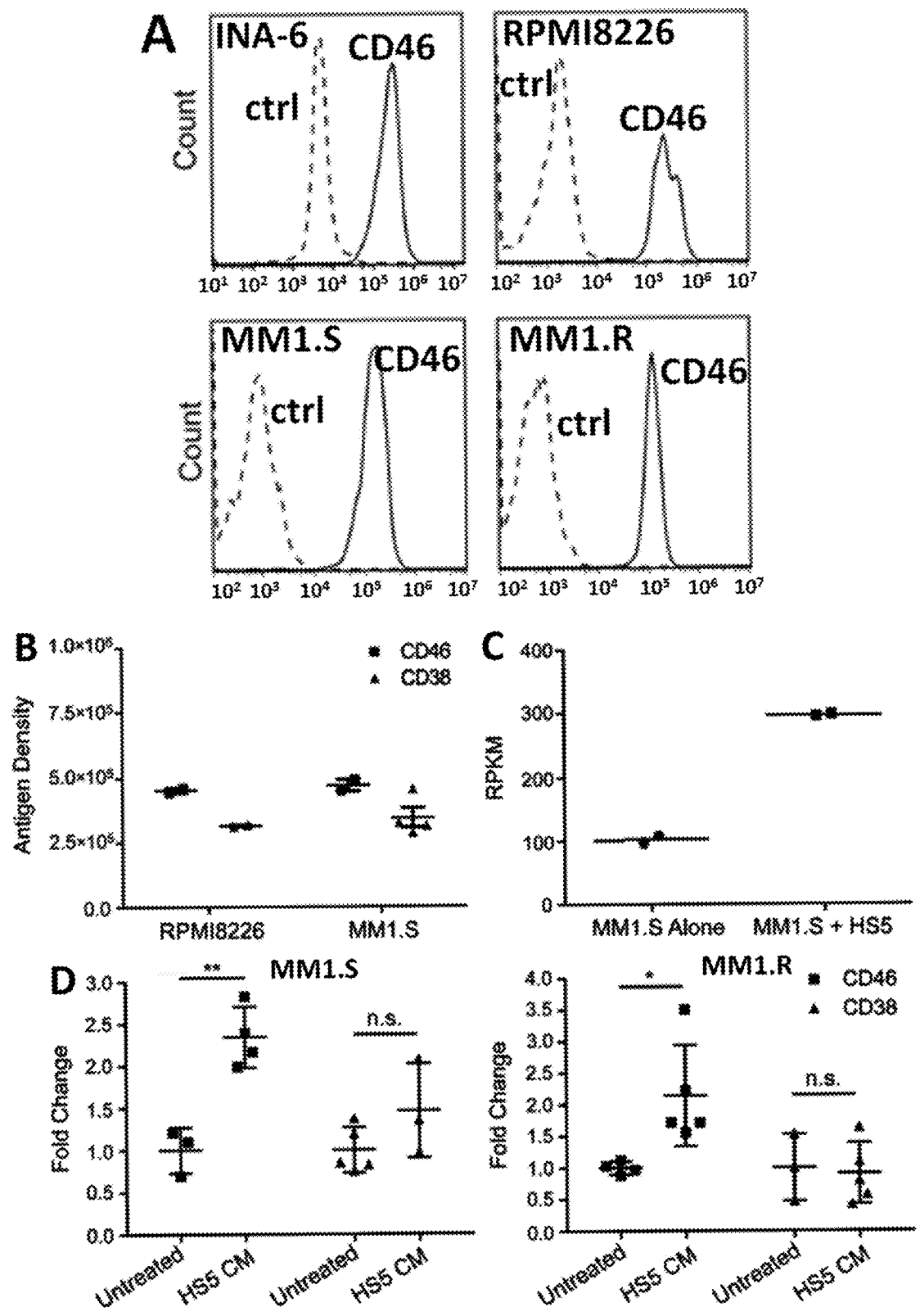
FIG. 1, panels A-D, shows CD46 as highly expressed on MM cells and further increased in the setting of BM microenvironment. Panel A) CD46 expression in INA-6, RPMI8226, MM1.S and MM1.R measured by FACS (solid lines), compared to nonbinding control (Ctrl=dashed lines, representative data, n=3). Panel B) CD46 antigen density estimation compared to CD38 on RPM18226 and MM1.S (data represent mean+/− SEM, n=3). Panel C) Co-culture of MM1.S with HS5 BM stromal cells increases the expression of CD46 mRNA (n=2). Panel D) CD46 and CD38 antigen densities in RPMI8226 and MM1.S, incubated with or without HS5 conditioned media (CM) for 3 days (data represent mean+/− SEM, n=3-5). Two-tailed Student's t test, *p<0.05, **p<0.01.
Figure 2:
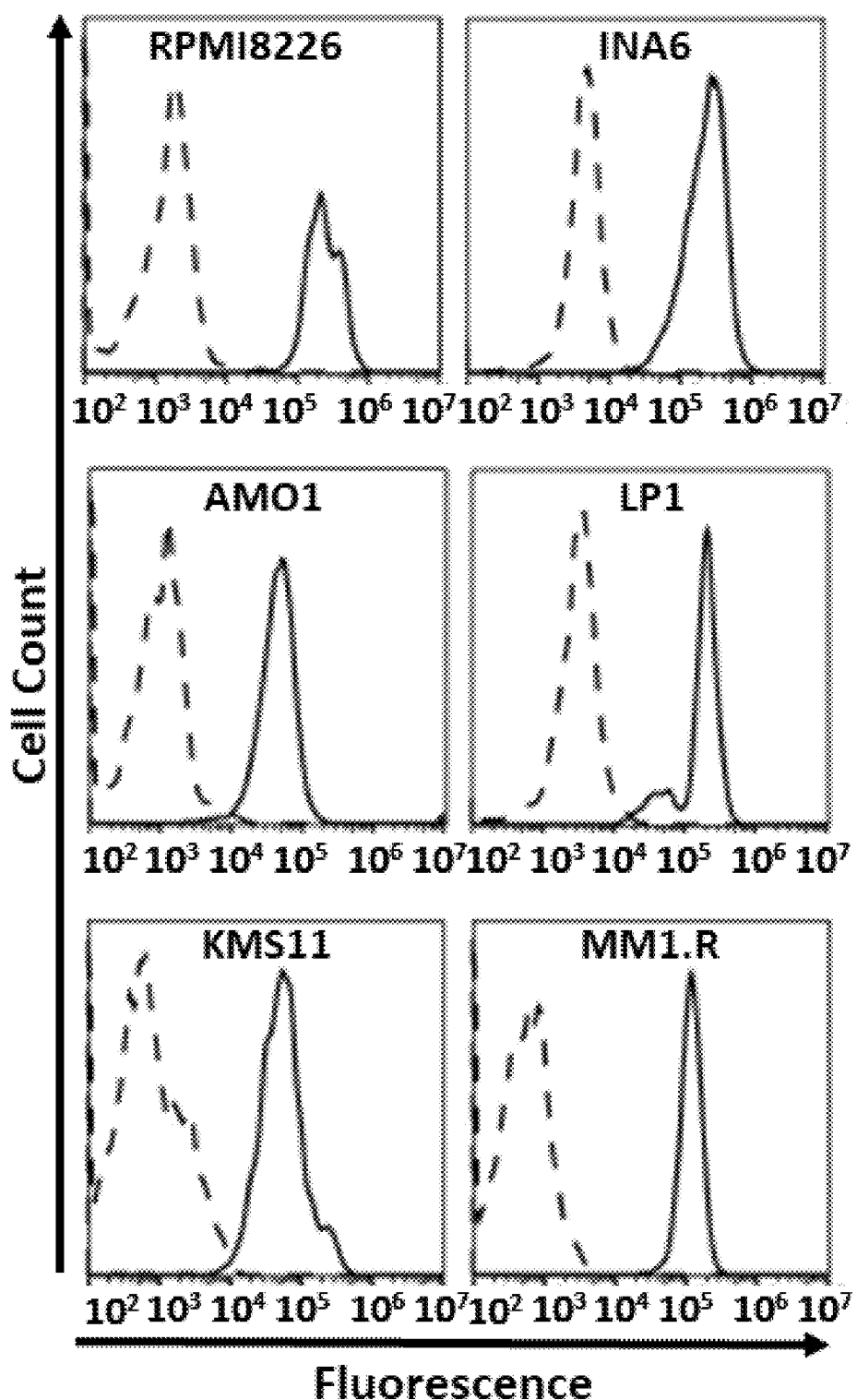
FIG. 2 shows FACS analysis of cell surface expression of CD46 on myeloma cell line panel.
Figure 3:
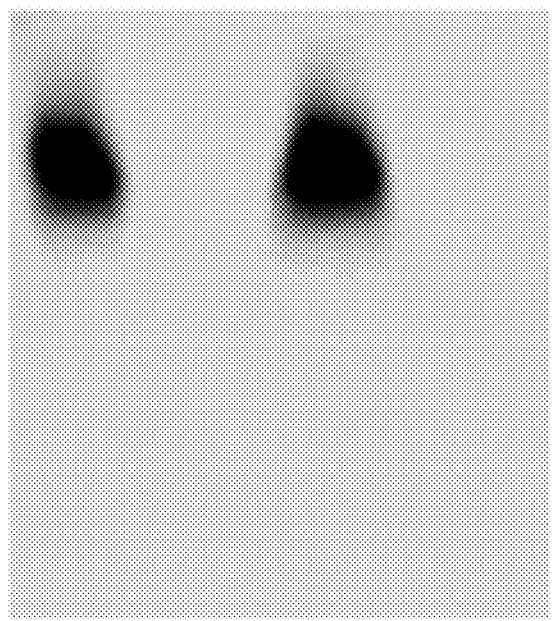
FIG. 3, panels A and B, shows that extracellular CD46 antigen does not have appreciable shedding from cell surface and no antibody-stimulated shedding was observed.
Figure 3:
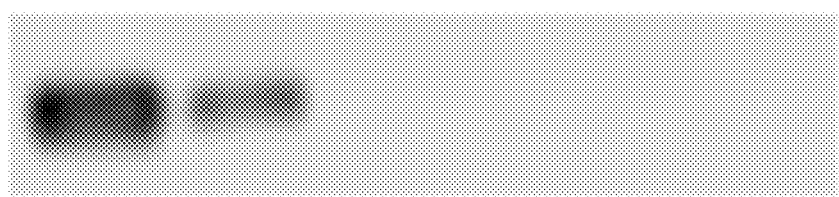

To evaluate whether CD46 was overexpressed in MM, cell surface expression of different cell lines was studied by fluorescence-activated cell sorting (FACS). CD46 was overexpressed on the cell surface of all MM cell lines tested (FIG. 1A and FIG. 2). The number of CD46 antigen number per cell (referred to henceforth as antigen density) was further quantified. The mean antigen density on MM cell lines RPMI8226 and MM1.S ranged from 454,668-470,991 for CD46, compared to 314,953-344,865 for CD38, a commonly used marker for MM (FIG. 1B). It has previously been reported that extracellular CD46 antigen is shed from the cell surface of solid tumor cell lines. To assess if MM cells shed CD46 antigen, western blotting of cell lysates was conducted and supernatants was obtained from RPM18226 cells. Either in the presence or absence of CD46 antibody-stimulation, shedding of CD46 antigen was not found from MM cells into the culture supernatant (FIG. 3).

CD46 is Upregulated in the Context of the Bone Marrow Microenvironment

Myeloma is a disease in which the BM microenvironment promotes MM cell survival and chemotherapy resistance. The majority of MM patients have disease that is primarily localized to the BM. To assess whether the CD46 expression level in MM cells is impacted by this microenvironment, MM1.S cells were co-cultured with the BM stromal cell line HS5. Analysis of mRNA expression by RNA-seq showed the CD46 mRNA level increased in MM1.S when co-cultured with HS5, compared to mono-cultures (FIG. 1C). To assess whether this observation could be generalized to other MM cell lines and co-culture conditions, MM1.S and MM1.R were incubated with HS5 conditioned media and analyzed by FACS for CD46. For comparison, CD38 was also studied in parallel. MM1.S and MM1.R cells showed upregulation of CD46 when cultured with HS5 conditioned media (P=0.0031 and 0.02, respectively), suggesting that a factor from BM stromal cells may increase CD46 expression by MM cells (FIG. 1D). In contrast, CD38 showed a variable response upon incubation of MM1.S and MM1.R cells with stromal cell conditioned media (P=0.15 and 0.8, respectively) (FIG. 1D).

Generation of Anti-CD46 Antibody and Internalization By Myeloma Cells

Figure 4:
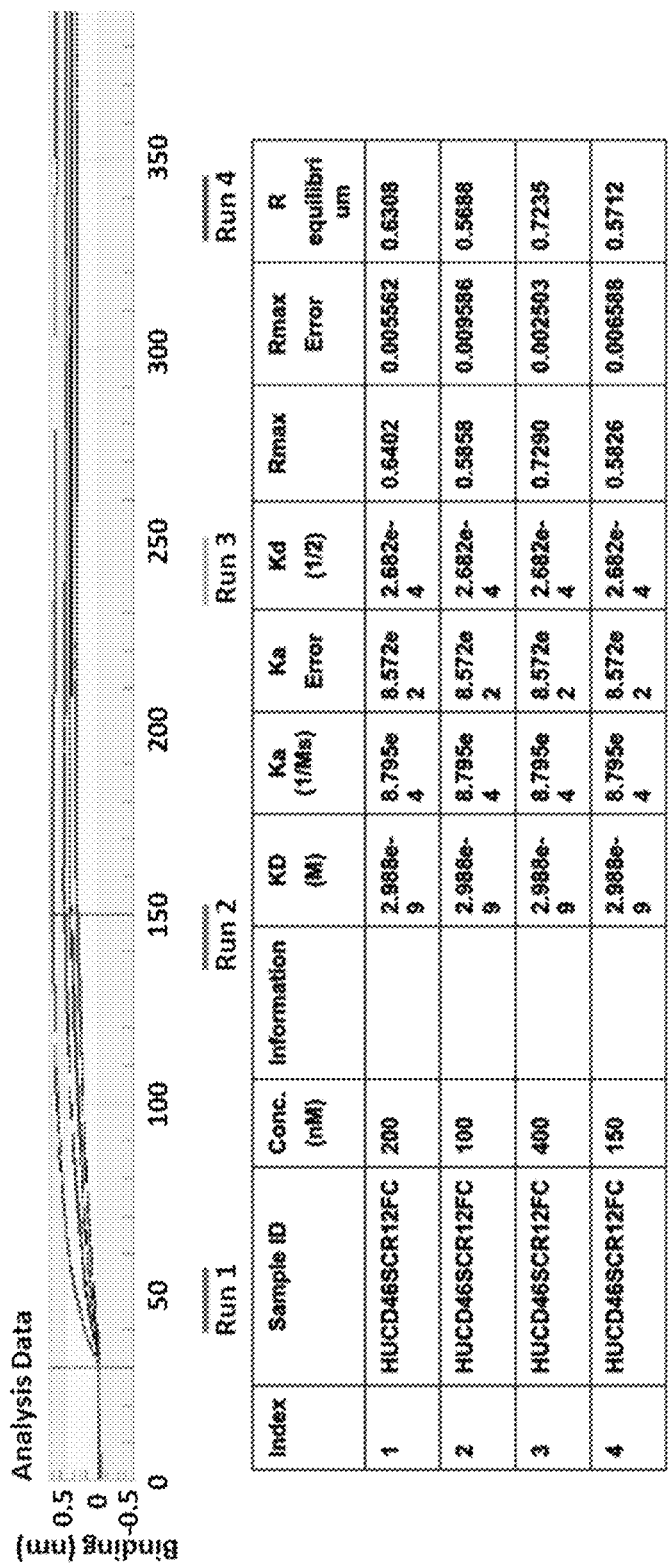
FIG. 4 shows antibody affinity for recombinant human CD46.
Figure 5:
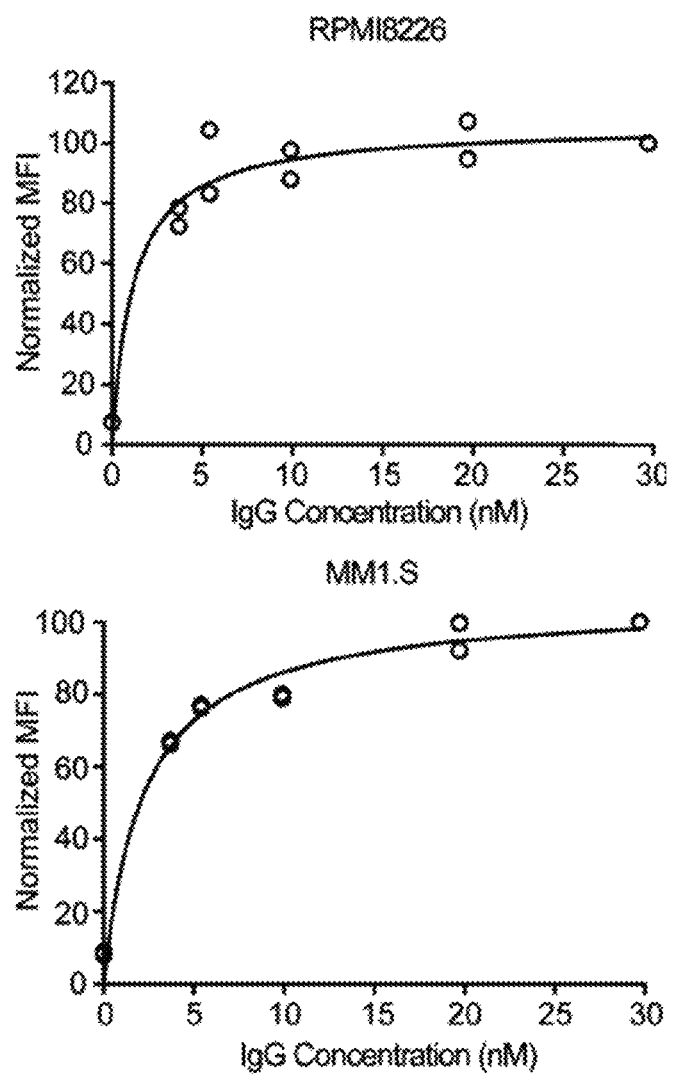
FIG. 5 illustrates antibody affinity for living multiple myeloma cells.

A panel of human monoclonal antibodies binding to domain 1 and 2 of human CD46 by phage and yeast antibody display was generated and an antibody YS5 that binds to the target antigen specifically with high affinity was identified. The equilibrium dissociation constant ($K_D$) of the antibody on a recombinant human CD46 protein fragment was 2.99 nM on the BLItz system (FIG. 4). Measured on living multiple myeloma cells, YS5 $K_D$ values were 1.19 nM for RPMI8226 and 2.24 nM for MM1.S, respectively (FIG. 5). To determine if the anti-CD46 antibody (YS5) is internalized by MM cells, the antibody was incubated with MM1.R, analyzed internalization using confocal microscopy, and studied co-localization with lysosomal-associated membrane protein 1 (LAMP1). CD46 antibody was internalized and co-localized with LAMP1 (FIG. 6A), indicating subcellular localization.

Anti-CD46-ADC has Potent and Selective Cytotoxicity Against Myeloma Cell Lines

To provide an initial assessment of CD46 as a suitable ADC target, the anti-CD46 antibody was conjugated to a membrane impermeant plant toxin (saporin) to form an immunotoxin and evaluated its effect on RPMI8226 cells. The immunotoxin showed inhibition of cell proliferation with EC50 in the picomolar range, with no effect observed from toxin alone (FIG. 7). In a second experiment, MMAF was also conjugated to the anti-CD46 antibody via a lysosomal protease sensitive valine-citrulline linker. High Performance Liquid Chromatography (HPLC) analysis with hydrophobic interaction chromatography (HIC) of the final conjugate showed an average drug per antibody of 3.3 (FIG. 8). The CD46-ADC was tested on the RMPI8226 cell line and found that it also killed MM cells with EC50 in the picomolar range (FIG. 6B).

Figure 6:
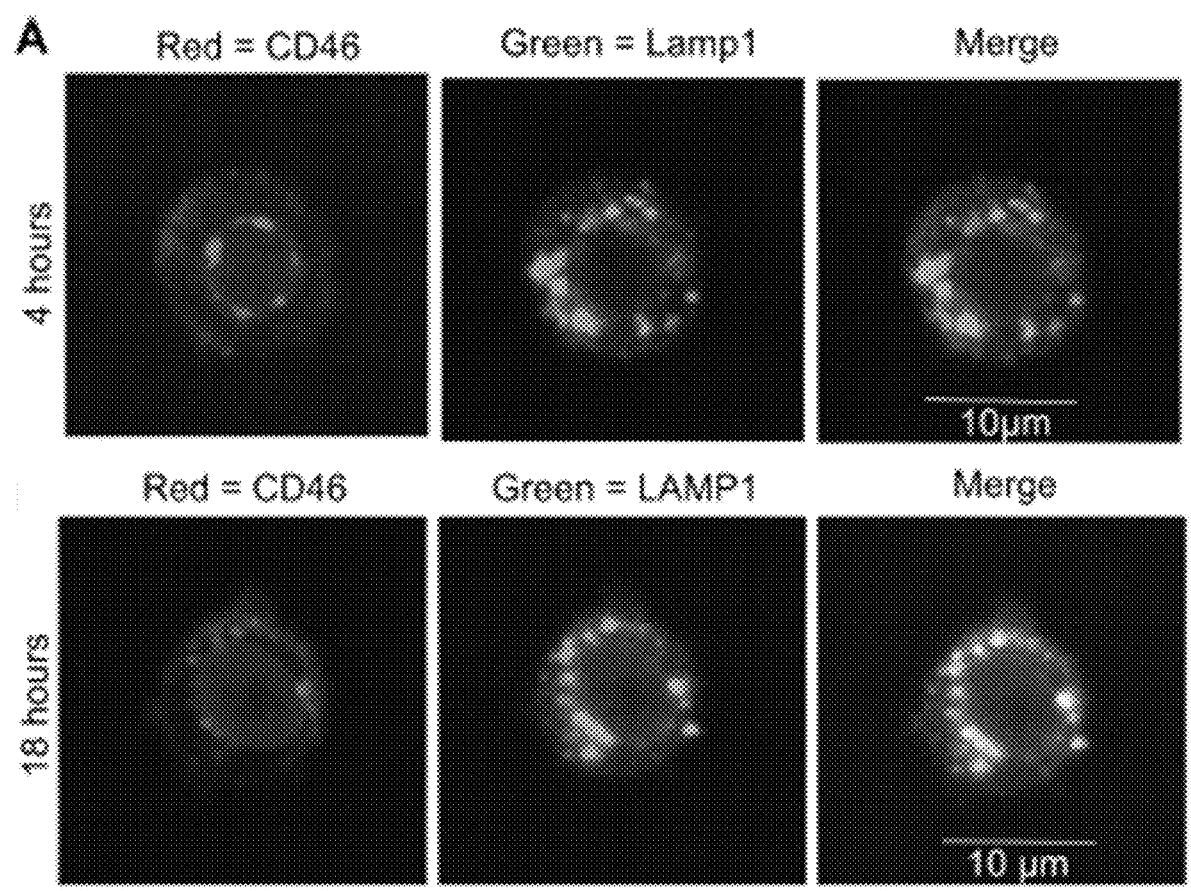
FIG. 6, panels A-E, shows potent and selective activity of CD46-ADC on MM cells compared to BM stromal cells, with potentiation of ADC effect in the context of MM-stromal interactions. Panel A) Confocal immunocytochemistry of MM1.R after 4 (left) and 18 (right) hours incubation with anti-CD46 antibody (red). Late lysosomes shown with anti-LAMP1 antibody (green), and partial colocalization shown in merged panel (yellow). Scale bars indicate 10 μM.

On the panel of MM cell lines, CD46-ADC showed EC50 range of 150 μM-5 nM (FIG. 6B). On BM stromal cells, CD46-ADC had EC50>100 nM for patient-derived BM61 (generated via culture of CD138-negative BM MNCs) cells and no effect on HS5 cells across all concentrations tested (up to 150 nM, no EC50 estimated) (FIG. 6B). Isotype control ADC constructed with a non-binding antibody showed little to no effect on MM cell line proliferation at concentrations up to 67 nM (FIG. 6C). The level of both CD46 transcript and cell surface expression measured by FACS correlated inversely with the EC50 of CD46-ADC (FIG. 9A-B) suggesting that surface expression is a reasonable surrogate for potency. The induction of apoptosis and death was detectable in MM cells tested for annexin V and propidium iodide (PI) after 48 hours of ADC treatment (FIG. 6D). Next, the effect of BM microenvironment interactions on the efficacy of CD46-ADC was examined. Co-cultures of MM1.S cells with BM61, HS5 or HS27A BM stromal cells enhanced the potency of CD46-ADC (FIG. 6E), consistent with the observations of increased CD46 expression in co-culture and correlation of potency to CD46 levels described above.

CD46-ADC cytotoxicity is dependent on binding to CD46 for specific tumor cell killing was also validated. First, competitive cell binding of the anti-CD46 antibody was measured and detected in the presence of increasing amounts of the recombinant CD46-Fc fusion protein (FIG. 10A). In addition, the CD46-Fc blocked the cytotoxic effect of CD46-ADC (FIG. 10B).

Next, the effect of CD46 knockdown on myeloma cell cytotoxicity of CD46-ADC was tested. The MM cell line H929 was infected with lentivirus coexpressing Green Fluorescent Protein (GFP) and shRNA against CD46. By quantitative FACS analysis, CD46 antigen density was knocked down by 82% from 146,647 in uninfected (GFP-negative) cells to 25,847 in GFP+ cells (FIG. 10C). The knockdown of CD46 reduced the induction of cell death by CD46-ADC compared to scrambled shRNA control (FIG. 10D), providing additional evidence that cytotoxicity of CD46-ADC is dependent on CD46 expression.

Anti-CD46-ADC Potently Eliminates MM Cell Line Xenografts In Vivo

RPMI8226 cells expressing firefly luciferase (RPMI8226-Luc) were used to establish an orthometastatic xenograft model in NOD.Cg-PrkdcscidIl2rgtm1Wjl/SzJ (NSG) mice. A total of 4 injections of CD46-ADC at 5 mg/kg were given once every 3-4 days. CD46-ADC resulted in near complete elimination of myeloma cell bioluminescent signal, whereas controls (vehicle, nonbinding ADC, naked antibody) did not (FIG. 11A-B). A comparison group was treated with bortezomib, which delayed increase in the bioluminescence activity but failed to reverse growth (FIG. 11B). It should be noted that this bortezomib schedule was chosen for comparison to the ADC, not to simulate clinical use, which would be continuous. The survival of mice treated with CD46-ADC was significantly improved over control groups (Hazard Ratio, HR=0.151 between control-ADC and CD46-ADC; p=0.004), with most of the treated animals living until study was discontinued at day 200 (FIG. 11C).

A luciferase reporter-bearing MM1.S cell line was used in a second xenograft model of orthometastatic MM. Two different ADC doses and a single dose regimen were investigated (FIG. 12). Mice were treated once every 3-4 days at either 4 mg/kg or 0.8 mg/kg for total 4 injections. A third group was treated with a single dose of 4 mg/kg. Tumor burden continually increased in the control groups treated with vehicle and control ADC (FIG. 12A). Naked CD46 antibody delayed increase in bioluminescence, but mice succumbed by day 53. The single dose showed elimination of bioluminescence by day 36, but all mice relapsed and succumbed by day 139 (FIG. 12C). The 0.8 mg/kg (4-dose) regimen eliminated bioluminescence through day 43, but all succumbed by day 173. The 4 mg/kg (4 dose) eliminated bioluminescent activity throughout the duration of the study, and all mice survived to study discontinuation at day 212. Together, these studies showed potent in vivo activity of CD46-ADC. This effect is dose dependent, with significant activity at a very low dose (0.8 mg/kg) (HR=0.215 compared to control-ADC; p=0.004) and apparent curative potential at a moderate dose of 4 mg/kg.

Establishing a Clinical Biomarker for CD46 Expression in Multiple Myeloma

The CD46 gene is located on 1q32, in proximity to a clinically used FISH probe at 1q21. In some instances, patients with amp1q21 also amplifies 1q32 and therefore carry increased CD46 expression. Datasets from previous gene expression analyses in MM were mined. By Affymetrix array, CD46 transcript increased 3-fold in MM cells compared to normal plasma cells (p=6.375×10-5) and was also increased in a sequential manner between MGUS (monoclonal gammopathy of unclear significance) and smoldering myeloma (asymptomatic proliferative plasma cell states) (FIG. 13A-C). Furthermore, data annotated by 1q21 FISH status demonstrated co-amplification of CD46 by array CGH (comparative genomic hybridization) (FIG. 13D) and a concomitant 2.8-fold increase in CD46 transcript expression (p=0.002) compared to MM samples that were 1q21 normal by FISH (FIG. 13E). Analysis of additional data derived from the CoMMpass StudySM (interim analysis 6) also confirm that ~30% of newly-diagnosed patients demonstrate focal amplification of the Myeloid Cell Leukemia-1 (MCL1) gene located at 1q21 (FIG. 14A). In addition to 1q21, the entirety of the 1q arm is amplified for a similar fraction of patients (FIG. 14A—grey track). Furthermore, co-amplification analysis for individual samples demonstrates that 85.4% of patients carrying MCL1 amplification also amplified CD46, and the majority of the 1q arm (purple line). In such cases, there is co-amplification between a negative prognostic factor (amp1q2l) and the gene for the CD46-ADC target. Additionally, comparison of the correlations of MCL1 with CD46 copy number and MCL1 with CKS1B (another gene located at 1q21) demonstrated that the 1q21 and 1q32 loci correlate similarly (FIG. 14B and FIG. 15A-B). Lack of correlation between CCND1 (chromosome 11) copy number with CD46 or MCL1 indicates that co-amplification is unique to genes on the 1q arm (FIG. 15C-D). Samples with copy gain on either CD46 or MCL1 also demonstrate increased CD46 transcript expression, compared to samples not demonstrating copy gain at these loci and to the overall population (FIG. 14C).

Cell Surface CD46 is Increased in Myeloma Samples with FISH Gain 1q21

To validate 1q21 FISH as a clinical biomarker, CD46 cell surface expression was measured in a cohort of patients at diagnosis or at relapse with a pure monoclonal population of MM cells (Table 3). An initial cohort of 10 MM patient samples was evaluated, 7 of which had amp1q2l and 3 without (Table 3, samples #1-10). CD46 co-expressed on the MM cell surface with known myeloma antigens CD38 and CD138 (FIG. 15A), but expressed at low levels on non-plasma cells (NPCs) that have negative/low CD38 and CD138 expression and represent a heterogeneous mixture of normal mononuclear cells (MNCs) (FIGS. 16A and B). The average MFI (anti-CD46) of CD138-positive/CD38-positive cells by FACS was 152,049 (Standard error of the mean, SEM 22,767) with amp1q21, significantly higher compared to 37,113 (SEM 9,926) in patients with normal 1q21 (p=0.014, two-tailed t-test, FIG. 16C). In such cases, CD46 was overexpressed on MM cells from all patients and further amplified in patients with amp1q21, with low expression on nonmalignant NPCs.

Table 3 illustrates clinical characteristics of MM patients tested for CD46 expression.

| Pt # | Age/Sex | Disease State | BM MM cell % | FISH | 1q21 copy number | Prior Tx |
|---|---|---|---|---|---|---|
| 1 | 57 m | Relapse | 15-20 | Normal | 2 | 1 |
| 2 | 73 m | Relapse | 50 | 1q+, Trisomy 13 | 3-4 | 2 |
| 3 | 65 m | Relapse | 4 | Normal | 2 | 6 |
| 4 | 63 f | New Dx | 70 | del17p, 1q+, 13q− | 3 | 0 |
| 5 | 48 m | New Dx PCL | >90 | 1q−, 9q+, t(14; 16), del17p | 1 | 0 |
| 6 | 57 f | Relapse | 50 | 1q+ | 4 | 7 |
| 7 | 51 m | New Dx | 70-80 | 1q+, 13q− | 3 | 0 |
| 8 | 42 f | Relapse | 70 | 1q+, del17p, 13q− | 3-6 | 2 |
| 9 | 68 f | Smoldering | 50-60 | 1q+, t(4; 14), 13q− | 4+ | 0 |
| 10 | 63 f | New Dx | 70-80 | 1q+, hyperdiploid, 13q− | 3 | 0 |
| 11 | 56 f | New Dx | 40 | 1q+, 11q+, 17+ | 3 | 0 |
| 12 | 65 f | New Dx | 70 | Normal | 2 | 0 |
| 13 | 57 m | Relapse | 20 | 1q+, 11q+ | 3 | 1 |
| 14 | 57 m | Relapse | 40-50 | 1q+, del17p | 4 | 9 |
| 15 | 58 m | New Dx | 60-75 | t(11; 14) | 2 | 0 |
| 16 | 59 f | New Dx | 90 | Normal | 2 | 0 |
| 17 | 70 m | Relapse | 40 | t(11; 14) | 2 | 4 |
| 18 | 36 f | New Dx | 80 | 1q+, 13q− | 4 | 0 |
| 19 | 69 f | Relapse | 40-50 | 1q+ | 3 | 1 |
| 20 | 61 m | Relapse | 60 | Normal | 2 | 10 |
| 21 | 42 f | New Dx | 70-80 | t(11; 14) | 2 | 0 |
| 22 | 45 f | New Dx | 40-50 | Hyperdiploid | 2 | 0 |
| 23 | 59 f | Relapse | 5-10 | 13q−, 1q+, del17p, 11q+ | 4 | 2 |
| 24 | 63 m | MGUS | 0 | N/A | N/A | 0 |
| 25 | 75 m | Remission | 0 | t(11; 14) | 1 | 2 |
| 26 | 51 m | New Dx | 10-25 | 1q+ | 4 | 0 |
| 27 | 55 m | Relapse | 10 | 1q+, 11q+ | 3 | 1 |

Samples (Pt) #1-10 were used for FACS in FIG. 17B, samples #11-20 were used for cell surface antigen density determination in FIG. 17C and samples #21-27 were used for normal cell population antigen density in FIG. 17D and Tables 4, 5 and 6. Dx—diagnosis, Pt—patient, m—male, f—female, Prior Tx—each prior line of treatment consisting of contiguous plan of therapy, separated by progression or toxicity, 1q+—gain of chromosome 1q21, del17p—deletion of chromosome 17p, t—translocation, MGUS—monoclonal gammopathy of undetermined significance.

Cell surface antigen density was measured by FACS to quantify the expression difference between amp1q21 and normal 1q21 patients. Samples were analyzed for CD46 cell surface expression on MM cells and matching NPCs from patients with and without amp1q2l. In a second cohort of 10 patients unselected MNCs were analyzed (Table 3, samples #11-20). In 5 patients with amp1q21 the mean CD46 antigen density on MM cells was 313,190 (SEM 68,849), while on NPCs was 26,214 (SEM 6,329) (FIG. 17B, two-tailed t-test, p=0.0032). In 5 patients with normal 1q21 the mean CD46 antigen density on MM cells was 121,316 (SEM 28,352), while on NPCs was 23,388 (SEM 3,729) (FIG. 17C, two-tailed t-test, p=0.009). CD46 antigen density was significantly higher on amp1q21 MM samples compared to MM with normal 1q (FIG. 17D, two-tailed t-test, p=0.032), supporting the hypothesis that CD46 cell surface expression variability in MM is due to selective genomic amplification in patients with amp1q2l.

Potential differentiation of the levels of CD46 on various non-tumorigenic or normal hematopoietic cell populations was further studied. CD46 antigen density was measured on hematopoietic stem cells (HSCs), progenitors, B-cells, T-cells, granulocytes, monocytes, megakaryocytes and platelets (FIG. 18). In BM from seven subsequent patients with MM, granulocytes had the highest CD46 antigen density (mean 39,248, SEM 6,492), but other non-tumor cell populations all had low CD46 expression (antigen density range 11,593-23,764) (FIG. 17E, Table 4). In BM from normal donors, monocytes (mean 58,320, SEM 6,874) and granulocytes (mean 54,439, SEM 10,688) had the highest CD46 antigen density, whereas others again were relatively low (range 8,443-23,772) (FIG. 17F, Table 5). Similar results were obtained from peripheral blood (PB) samples from normal donors, showing that CD46 antigen density is highest on monocytes (mean 56,237, SEM 11,649) and granulocytes (mean 40,523, SEM 8,165), but otherwise low (range 3,698-8,256) (FIG. 17G, Table 6).

Table 4 illustrates CD 46 antigen density quantitation for bone marrow cell populations from myeloma patients.

| | Patient # | | | | | | | Mean |
|---|---|---|---|---|---|---|---|---|
| | 21 | 22 | 23 | 24 | 25 | 26 | 27 | (SEM) |
| 1q Status | Nml | Nml | 1q+ | Nml | Nml | 1q+ | 1q+ | |
| MM cells | 92,278 | 63,564 | 132,820 | N/A | N/A | 378,436 | 155,464 | 164,512 (55,793) |
| HSCs | 19,554 | 31,068 | 18,954 | 16,027 | 23,168 | 31,068 | 26,511 | 23,764 (2,264) |

-continued

|  | Patient # | | | | | | | Mean |
|---|---|---|---|---|---|---|---|---|
|  | 21 | 22 | 23 | 24 | 25 | 26 | 27 | (SEM) |
| Progenitors | 47,943 | 23,981 | 8,642 | 19,311 | 14,674 | *N/A | 26,593 | 20,163 (5,768) |
| B-cells | 21,641 | 10,489 | 10,435 | 4,568 | 6,259 | 8,245 | 19,516 | 11,593 (2,465) |
| CD8+ T-cells | 16,528 | 27,438 | 18,450 | 12,996 | 17,031 | 38,795 | 35,407 | 23,806 (3,832) |
| CD4+ T-cells | 17,478 | 21,828 | 18,114 | 11,603 | 2,477 | 13,862 | 36,628 | 17,427 (3,960) |
| Granulocytes | N/A | N/A | 50,659 | 37,078 | 47,943 | 14,925 | 45,636 | 39,248 (2,254) |
| Monocytes | N/A | N/A | N/A | N/A | N/A | N/A | N/A | N/A |
| MKS | 29,461 | 16 | 9,018 | 11,369 | N/A | 36,055 | 36,312 | 20,372 (6,342) |

N/A: data not available, either not tested for normal populations or not detectable for MM cells in samples from patients in remission.
*Negative MFI values after background subtraction were not convertible to an antigen density number, so is also listed here as N/A. HSCs: hematopoietic stem cells. MKs: megakaryocytes. 1q+: gain of chromosome 1q by FISH.

table 5 illustrates CD46 antigen density quantitation for bone marrow cell populations from normal donors

| Cells | Markers | Nml 1 | Nml 2 | Nml 3 | Mean | SEM |
|---|---|---|---|---|---|---|
| Plasma Cells | CD38+ CD138+ | 16,565 | 32,132 | 18,728 | 22,475 | 4,869 |
| HSCs | CD34+ CD38− Lin− CD45+ | 15,920 | 16,465 | 22,559 | 18,315 | 2,128 |
| Progenitors | CD34+ CD38+ Lin− CD45+ | 13,609 | 15,765 | 16,999 | 15,458 | 991 |
| B-Cells | CD19+ CD45+ | 9,057 | 9,491 | 6,782 | 8,443 | 840 |
| CD8+ T-cell | CD3+ CD8+ CD4− CD45+ | 10,794 | 11,394 | 10,979 | 11,056 | 177 |
| CD4+ T-cell | CD3+ CD4+ CD8− CD45+ | 8,023 | 13,103 | 9,382 | 10,169 | 1,518 |
| Granulocytes | CD33+ CD45+ | 41,438 | 46,246 | 75,634 | 54,439 | 10,688 |
| Monocytes | CD14+ CD45+ | 44,579 | 64,823 | 65,558 | 58,320 | 6,874 |
| MKS | CD61+ CD45+ | 23,339 | 24,300 | 23,677 | 23,772 | 281 |

HSCs—hematopoietic stem cells. MKs—megakaryocytes.

Table 6 illustrates CD46 antigen density quantitation for peripheral blook cell populations from normal donors.

| Cells | Markers | Nml 4 | Nml 5 | Nml 6 | Mean | SEM |
|---|---|---|---|---|---|---|
| B-Cells | CD19+ CD45+ | 6,056 | 7,106 | 9,327 | 7,496 | 964 |
| CD8+ T-cell | CD3+ CD8+ CD4− CD45+ | 2,087 | 3,474 | 5,532 | 3,698 | 1,001 |
| CD4+ T-cell | CD3+ CD4+ CD8− CD45+ | 7,209 | 7,927 | 9,631 | 8,256 | 718 |
| Granulocytes | CD33+ CD45+ | 39,102 | 33,162 | 49,305 | 40,523 | 4,714 |
| Monocytes | CD14+ CD45+ | 51,399 | 38,920 | 78,393 | 56,237 | 11,649 |
| Platelets | CD61+ CD45− | 4,940 | 8,002 | 1,148 | 4,697 | 1,982 |

In some instances, CD46 expression was high on MM cells from 100% patients (n=25, cumulatively) relative to normal cells and further amplified in patients with amp1q21. The overall CD46 expression on normal hematopoietic cells is low. Monocytes and granulocytes expressed relatively higher levels of CD46 compared to other normal cell populations. Benign plasma cells from normal donors also had low CD46 antigen density of CD46 (mean 22,475, SEM 4,869, FIG. 17F, Table 5), suggesting that in some instances, high CD46 on MM cells occurs with malignant transition. Anti-CD46-ADC Potently and Selectively Induces Primary MM Cell Apoptosis and Death Internalization of the anti-CD46 antibodies by primary MM cells was studied. As shown in FIG. 19A (left panel), the anti-CD46 antibody was internalized and partially co-localized with LAMP1. In contrast, no internalization into CD138-negative MNCs was observed (FIG. 19A, right). The study further evaluated whether CD46-ADC was specifically cytotoxic to primary MM cells ex vivo. BM MNCs were treated with 0-100 nM in triplicate for each condition and evaluated by FACS after 48 hours. CD46-ADC treatment consistently reduced the number of MM cells, with no effect from nonbinding ADC control (FIG. 19B). CD46-ADC had no effect on the number of NPC in all patients tested (FIG. 19C). Furthermore, the MM cells with gain of chromosome 1q21 showed higher sensitivity to CD46-ADC (lower EC50) compared to patients with normal 1q21 (FIG. 19B). In some instances, a weak correlation with known 1q21 copy number and CD46-ADC potency was found in a select number of myeloma cell lines (FIG. 9C).

ADC induction of apoptosis was evaluated and death of CD138-positive and CD138-negative fractions by FACS.

Gating specifically on CD38-positive, CD138-selected cells, FACS for Annexin V and PI was performed after 48-hour treatment of MM patient cells ex vivo with graded concentrations CD46-ADC. Gating for viable Annexin V-negative/PI-negative cells, MM cell killing at 48 hours was consistent with cell line proliferation assays at 96 hours, with EC50<10 nM (FIG. 20). No toxic effect on nonmalignant CD138-negative cells was observed up to 100 nM (FIG. 20).

Tolerability Evaluation of CD46-ADC in Human CD46 Expressing Transgenic Mice

Tolerability of CD46-ADC in vivo was studied using a relevant animal model. Following a single i.v. bolus injection of 6 mg/kg CD46-ADC, animals were monitored for body weight loss and sign of overt toxicity for 14 days. No significant body weight loss or overt sign of toxicity was observed (FIG. 21A). At study discontinuation on day 14, necropsy study was performed. All organs appeared to be morphologically normal except for a slight increase in spleen size in CD46-ADC treated animals. Histologic analysis of major organs showed no notable tissue damage (FIG. 21B at 20× and FIG. 22 at 40× magnification). To assess if CD46-ADC caused any notable effect on B cells in the spleen, spleen sections were stained with anti-mouse CD20 (FIG. 21C). The diameters of CD20 positive regions in CD46-ADC were measured and control ADC treated groups, and found no statistically significant difference (FIG. 21D). In such cases, CD46-ADC is tolerated in vivo.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method comprising:
   a) determining whether nucleic acid in cancer cells of a subject show a modification at chromosome location 1q21;
   wherein a modification at chromosome location 1q21 indicates that the cancer cells are responsive to a CD46-targeted therapy; and
   b) administering a therapeutically effective amount of the CD46-targeted therapy, wherein the CD46-targeted therapy is a pharmaceutical composition comprising
      (i) an anti-CD46 antibody comprising
         a heavy chain variable region comprising a variable heavy (VH) CDR1 that comprises an amino acid sequence of SEQ ID NO: 3, a VH CDR2 that comprises an amino acid sequence of SEQ ID NO: 4, and a VH CDR3 that comprises an amino acid sequence of SEQ ID NO: 5; and
         a light chain variable region comprising a variable light (VL) CDR 1 that comprises an amino acid sequence of SEQ ID NO: 6, a VL CDR 2 that comprises an amino acid sequence of SEQ ID NO: 7, and a VL CDR 3 that comprises an amino acid sequence of SEQ ID NO: 8; attached to
      (ii) at least one payload wherein the at least one payload comprises an auristatin;
   wherein the modification at chromosome location 1q21 is a copy number gain of 1q21.

2. The method of claim 1, wherein the cancer cells further comprise an overexpression of CD46.

3. The method of claim 1, wherein the determining comprises a presence or absence of a copy number gain at 1q21.

4. The method of claim 1, wherein the determining comprises using a method selected from the group consisting of fluorescent in-situ hybridization (FISH), gene chip hybridization, multiplexed gene expression analysis, hybridization based digital barcode quantification assays, and lysate based hybridization assays utilizing branched DNA signal amplification.

5. The method of claim 1, wherein the determining comprises using fluorescent in-situ hybridization (FISH).

6. The method of claim 1, wherein the pharmaceutical composition is formulated for parenteral administration.

7. The method of claim 1, wherein the pharmaceutical composition is administered to the subject as an injection or as an infusion.

8. The method of claim 1, wherein the subject is a human.

9. The method of claim 1, wherein the auristatin is selected from the group consisting of Monomethylauristatin F (MMAF), Auristatin E (AE), and Monomethylauristatin E (MMAE).

10. The method of claim 1, wherein the auristatin is MMAE.

* * * * *